US012559502B2

(12) United States Patent
Xu et al.

(10) Patent No.: US 12,559,502 B2
(45) **Date of Patent: *Feb. 24, 2026**

(54) THIENO PYRIMIDINES AS FERROPORTIN INHIBITORS

(71) Applicant: Global Blood Therapeutics, Inc., South San Francisco, CA (US)

(72) Inventors: Qing Xu, South San Francisco, CA (US); Zhe Li, South San Francisco, CA (US); Shahul Nilar, South San Francisco, CA (US)

(73) Assignee: Global Blood Therapeutics, Inc, South San Francisco, CA (US)

( * ) Notice: Subject to any disclaimer, the term of this patent is extended or adjusted under 35 U.S.C. 154(b) by 694 days.

This patent is subject to a terminal disclaimer.

(21) Appl. No.: 17/921,905

(22) PCT Filed: Apr. 28, 2021

(86) PCT No.: PCT/US2021/029564
§ 371 (c)(1),
(2) Date: Oct. 27, 2022

(87) PCT Pub. No.: WO2021/222359
PCT Pub. Date: Nov. 4, 2021

(65) Prior Publication Data

US 2023/0159553 A1 May 25, 2023

Related U.S. Application Data

(60) Provisional application No. 63/016,737, filed on Apr. 28, 2020.

(51) Int. Cl.

| | |
|---|---|
| ***C07D 495/04*** | (2006.01) |
| ***A61K 31/519*** | (2006.01) |
| ***C07D 519/00*** | (2006.01) |

(52) U.S. Cl.
CPC ......... *C07D 495/04* (2013.01); *C07D 519/00* (2013.01)

(58) Field of Classification Search
CPC ........ C07D 495/04; A61K 31/519; A61P 7/00
USPC ........................................ 544/253; 514/258.1
See application file for complete search history.

(56) References Cited

FOREIGN PATENT DOCUMENTS

| | | |
|---|---|---|
| WO | WO 2011/026835 | 3/2011 |
| WO | WO 2020/123850 | 6/2020 |

OTHER PUBLICATIONS

Bourguignon, J. et al., "Syntheses de Thieno[2,3-d]pyrimidines substituees en 2 et 4 II," Bulletin De La Societe Chimique De France, 2 Partie, No. 11/12, 2483-2487, (Nov. 1, 1975).
Bourguignon, J. et al., "Syntheses de Thieno[2,3-d]pyrimidines substituees en 2 et 4," Bulletin De La Societe Chimique De France, 2 Partie, No. 3/4, 815-819, (Mar. 1, 1975).
WIPO Application No. PCT/US2021/029564, PCT International Preliminary Report on Patentability mailed Nov. 10, 2022.
WIPO Application No. PCT/US2021/029564, PCT International Search Report and Written Opinion of the International Searching Authority mailed Aug. 4, 2021.

*Primary Examiner* — Charanjit Aulakh
(74) *Attorney, Agent, or Firm* — John A. Wichtowski

(57) ABSTRACT

The subject matter described herein is directed to ferroportin inhibitor compounds of Formula I and pharmaceutical salts thereof, methods of preparing the compounds, pharmaceutical compositions comprising the compounds, and methods of administering the compounds for prophylaxis and/or treatment of diseases caused by a lack of hepcidin or iron metabolism disorders, particularly iron overload states, such as thalassemia, sickle cell disease and hemochromatosis, and also kidney injuries.

38 Claims, No Drawings

THIENO PYRIMIDINES AS FERROPORTIN INHIBITORS

CROSS-REFERENCE TO RELATED APPLICATIONS

This application is a 35 U.S.C. § 371 national stage of International Application No. PCT/US2021/029564, filed Apr. 28, 2021, which claims the benefit of and priority to U.S. Provisional Application No. 63/016,737, filed on Apr. 28, 2020, the contents of each are hereby incorporated by reference in their entirety.

FIELD

The subject matter described herein is directed to ferroportin inhibitor compounds, methods of making the compounds, their pharmaceutical compositions and their use in the prophylaxis and/or treatment of diseases caused by a lack of hepcidin or iron metabolism disorders, particularly iron overload states, such as thalassemia, sickle cell disease and hemochromatosis, and also kidney injuries.

BACKGROUND

In nearly all organisms, iron is an essential trace element. In humans, iron is a critical component for oxygen transport, oxygen uptake, cell functions such as mitochondrial electron transport, cognitive functions, and energy metabolism. Iron is present in enzymes, hemoglobin and myoglobin, as well as in depots in the form of ferritin and hemosiderin. With respect to hemoglobin, approximately half of all iron is present as heme iron, bound in the hemoglobin of the erythrocytes. The human body contains on average approximately 4 to 5 g iron. The iron requirement of a human adult is between 0.5 to 1.5 mg per day, whereas infants and women during pregnancy require 2 to 5 mg of iron per day.

In a healthy human adult, the normal daily loss of iron of about 1 mg is usually replaced via food intake. Iron balance is primarily regulated by recycling and iron recovery from hemoglobin of aging erythrocytes and the duodenal absorption of dietary iron in the form of divalent as well as trivalent iron ions.

Absorption is regulated by the organism depending on the iron requirement and the size of the iron depot. Usually, Fe(III) compounds are dissolved in the stomach at a sufficiently acidic pH value and thus made available for absorption. The absorption of the iron is carried out in the upper small intestine by mucosal cells. Trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or released into the blood by the transport protein ferroportin. The divalent iron transported into the blood by ferroportin is converted into trivalent iron by oxidases (ceruloplasmin, hephaestin). The trivalent iron is then transported to its destination in the organism by transferrin. ("Balancing acts: molecular control of mammalian iron metabolism," M. W. Hentze, Cell, 1:17, 2004, 285-297). Hepcidin plays a central role in this process because it is the essential regulating factor of iron absorption. The hepcidin-ferroportin system directly regulates iron metabolism.

Iron uptake and storage is regulated by hepcidin. Hepcidin Antimicrobial Peptide (HAMP; also known as LEAP-1; further referred to as Hepcidin) is a 25 amino acid peptide (Krause et al., FEBS Lett. 480, 147-150, 2000). Hepcidin has a hairpin structure with 8 cysteines that form 4 disulfide bridges (Jordan et al., J Biol Chem. 284, 24155-24167, 2009). The N-terminus appears to be important for the iron-regulatory function since deletion of the first 5 amino acids resulted in complete loss of bioactivity (Nemeth et al., Blood, 107, 328-333, 2006). Hepcidin is produced in the liver and functions as the master iron regulatory hormone controlling intestinal iron uptake, and also regulates iron storage in other organs (Ganz, Hematol. Am. Soc. Hematol. Educ. Program, 29-35, 507 2006; Hunter et al., J. Biol. Chem. 277, 37597-37603, 2002; Park et al., J. Biol. Chem. 276, 7806-7810, 2001). Hepcidin limits iron-uptake by binding to the iron transport molecule ferroportin and causing its degradation (Sebastiani et al., Front. Pharmacol. 7, 160, 2016).

The formation of hepcidin is regulated in direct correlation to the organism's iron level, i.e., if the organism is supplied with sufficient iron and oxygen, more hepcidin is formed; if iron and oxygen levels are low, or in case of increased erythropoiesis, less hepcidin is formed. In the small intestinal mucosal cells and in the macrophages hepcidin binds with the transport protein ferroportin, which conventionally transports the phagocytotically recycled iron from the interior of the cell into the blood.

Ferroportin is an iron transporter that plays a key role in regulating iron uptake and distribution in the body and thus in controlling iron levels in the blood. The transport protein ferroportin is a transmembrane protein consisting of 571 amino acids which is formed in the liver, spleen, kidneys, heart, intestine and placenta. In particular, ferroportin is localized in the basolateral membrane of intestinal epithelial cells. Ferroportin bound in this way thus acts to export the iron into the blood. In this case, it is most probable that ferroportin transports iron as $Fe^{2+}$. If hepcidin binds to ferroportin, ferroportin is transported into the interior of the cell, where its breakdown takes place so that the release of the phagocytotically recycled iron from the cells is then almost completely blocked. If the ferroportin is inactivated, for example by hepcidin, so that it is unable to export the iron which is stored in the mucosal cells, the stored iron is lost with the natural shedding of cells via the stools. The absorption of iron in the intestine is therefore reduced, when ferroportin is inactivated or inhibited, for example by hepcidin.

A decrease of hepcidin results in an increase of active ferroportin, thus allowing an enhanced release of stored iron and an enhanced iron uptake, e.g., from the food, resulting in an increase in serum iron levels, i.e., iron overload. Iron overload causes many diseases and undesired medical conditions. Iron overload can be treated by removal of the iron from the body. This treatment includes regularly scheduled phlebotomies (bloodletting). For patients unable to tolerate routine blood draws, there are chelating agents available for use. A disadvantage in the treatment of iron overload by chelation therapy is the removal of the chelated iron from the body when the iron overload has already occurred instead of preventing the occurrence of the disorder.

What is therefore needed and not effectively addressed by the art are compounds that act as ferroportin inhibitors that have desired efficacy and therapeutic potential. This problem as well as others stemming from iron imbalance are addressed by the subject matter described herein.

BRIEF SUMMARY

In certain embodiments, the subject matter described herein is directed to a compound of Formula I or a pharmaceutically acceptable salt thereof.

In certain embodiments, the subject matter described herein is directed to a pharmaceutical composition comprising a compound of Formula I or a pharmaceutically acceptable salt thereof.

In certain embodiments, the subject matter described herein is directed to methods of inhibiting iron transport mediated by ferroportin in a subject, comprising administering to the subject an effective amount of a compound of Formula I, a pharmaceutically acceptable salt thereof, or a pharmaceutical composition comprising a compound of Formula I In certain embodiments, the subject matter described herein is directed to methods of preparing compounds of Formula I.

Other embodiments are also described.

DETAILED DESCRIPTION

Described herein are ferroportin inhibitor compounds of Formula I, methods of making the compounds, pharmaceutical compositions comprising the compounds and their use in the prophylaxis and/or treatment of diseases caused by a lack of hepcidin or iron metabolism disorders, particularly iron overload states, such as thalassemia, sickle cell disease and hemochromatosis. Ferroportin is the iron transport protein responsible for the uptake of the released iron via the intestine and its transfer into the blood circulation, where ultimately the iron is delivered to the appropriate tissues and organs. Inactivation or inhibition of the ferroportin reduces or prevents the export of the iron, thereby reducing the absorption of iron in the intestine and ultimately the amount of iron in the body. These compounds, compositions and methods can be used for an effective therapy for the prophylaxis and treatment of iron metabolism disorders which are associated with increased iron levels. It is desirable to provide compounds, compositions and methods that exhibit few side effects, have very low toxicity and good bioavailability and compatibility.

Iron overload has been associated with a variety of diseases (Blanchette et al., Expert Rev. Hematol. 9, 169-186, 2016). Hereditary hemochromatosis is the most common inherited disease in Europe and is caused by lack of, or insensitivity to, hepcidin (Powell et al., The Lancet 388, 706-716, 2016). The clinical manifestation of hemochromatosis are hepatic cirrhosis, diabetes, and skin pigmentation (Powell et al., The Lancet 388, 706-716, 2016). While this disease can be managed by phlebotomy, this approach may be cumbersome and does not treat the cause of the disease.

Iron-loading anemias such as beta-thalassemia are also associated with reduced hepcidin levels (Origa et al., Haematologica 92, 583-588, 2007). Treatment of this disease with hepcidin mimetics may not only address the iron overload, but has also been shown to improve the ineffective erythropoiesis that occurs in this disease (Casu et al., Blood 128, 265-276, 2016). This may be of major benefit for thalassemia patients who may be less dependent on blood transfusions, which can contribute to the iron overload in these patients.

Myelofibrosis, myelodysplastic syndrome, and sickle cell disease are diseases that are also characterized by ineffective erythropoiesis and that may require frequent blood transfusions (Carreau et al., Blood Rev. 30, 349-356, 2016; Temraz et al., Crit. Rev. Oncol. Hematol. 91, 64-73, 2014; Walter et al., Acta Haematol. 122, 174-183, 2009). Reduced hepcidin levels have been described in some of these patients (Cui et al., Leuk. Res. 38, 545-550, 2014; Santini et al., PLoS ONE 6, e23109, 2011). Hepcidin mimetics may also be beneficial in these patients.

Polycythemia vera is a disease characterized by increased erythropoiesis. It has been shown in animal models that high doses of hepcidin mimetics can ameliorate this disease by diminishing erythropoiesis (Casu et al., Blood 128, 265-276, 2016).

Reduction of iron uptake and thereby serum iron levels may even be beneficial in diseases where iron load is normal, such as kidney diseases (Walker and Agarwal, Nephrol. 36, 62-70, 2016), infections with iron-dependent bacteria (Arezes et al., Cell Host Microbe 17, 47-57, 2015), and polymicrobial sepsis (Zeng et al., Anesthesiology, 122, 374-386, 2015).

Hepcidin itself is limited in its use as a drug because of its complex structure which requires a complicated manufacturing, and also its limited in vivo duration of action. Continuous efforts have been made to search for hepcidin mimetics and chemical compounds that could be used to increase hepcidin levels.

A common approach relates to small hepcidin-derived or hepcidin-like peptides, which can be produced affordably, and can be used to treat hepcidin-related diseases and disorders such as those described herein. Such so-called mini-hepcidins are rationally designed small peptides that mimic hepcidin activity and may be useful for the treatment of iron overload, and also iron overload related disease symptoms.

Such mini-hepcidin peptides are described for example in WO 2010/065815 A2 and WO 2013/086143 A1. WO 2015/157283 A1 and the corresponding U.S. Pat. No. 9,315,545 B2 describe hepcidin mimetic peptides and the use thereof in hepcidin-related disorders, such as iron overload, beta-thalassemia, hemochromatosis etc. and cover a development compound M012 of the company Merganser Biotech, having been under evaluation in a Phase 1 clinical program as a potentially transformative therapy for a number of hematological diseases including beta-thalassemia, low risk myelodysplasia and polycythemia vera.

WO 2014/145561 A2 and WO 2015/200916 A2 describe further small hepcidin peptide analogues and the use thereof in the treatment or prevention of a variety of hepcidin-related diseases, including iron overload diseases and iron-loading anemias, and further related disorders. Further, WO2015/042515 A1 relates to hepcidin and its peptide fragments, which are particularly intended for treating renal ischemia reperfusion injury or acute kidney injury. Further, mini-hepcidin analogs are described for example by Preza et al., J. Clin. Invest., 121 (12), 4880-4888, 2011 or in CN 104 011 066 and in WO 2016/109363 A1.

Ferroportin inhibitors as well as compounds that have hepcidin-like activity are needed that also possess additional beneficial properties such as improved solubility, stability, and/or potency. An advantage of the ferroportin inhibitor compounds of Formula I described herein is their preparation in sufficient yields by the synthetic routes disclosed herein.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literature, patents, and similar materials differs from or contradicts this application, including but not limited to defined terms, term usage, described techniques, or the like, this application controls.

I. Definitions

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, $—C(O)NH_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±50%. In certain other embodiments, the term "about" includes the indicated amount±20%. In certain other embodiments, the term "about" includes the indicated amount±10%. In other embodiments, the term "about" includes the indicated amount±5%. In certain other embodiments, the term "about" includes the indicated amount±1%. In certain other embodiments, the term "about" includes the indicated amount±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_1$-$C_{20}$ alkyl), 1 to 12 carbon atoms (i.e., $C_1$-$C_{12}$ alkyl), 1 to 8 carbon atoms (i.e., $C_1$-$C_8$ alkyl), 1 to 6 carbon atoms (i.e., $C_1$-$C_6$ alkyl), 1 to 4 carbon atoms (i.e., $C_1$-$C_4$ alkyl), or 1 to 3 carbon atoms (i.e., $C_1$-$C_3$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and "propyl" includes n-propyl (i.e., $—(CH_2)_2CH_3$) and isopropyl (i.e., $—CH(CH_3)_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl) or 2 to 4 carbon atoms (i.e., $C_2$-$C_4$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_2$-$C_{20}$ alkynyl), 2 to 8 carbon atoms (i.e., $C_2$-$C_8$ alkynyl), 2 to 6 carbon atoms (i.e., $C_2$-$C_6$ alkynyl) or 2 to 4 carbon atoms (i.e., $C_2$-$C_4$ alkynyl). The term "alkynyl" also includes those groups having one triple bond and one double bond.

The term "alkylene" by itself or as part of another substituent means a divalent radical derived from an alkane, such as, methylene $—CH_2—$, ethylene $CH_2CH_2—$, and the like. As an example, a "hydroxy-methylene" refers to $HO—CH_2—$*, where * is the attachment point to the molecule.

"Alkoxy" refers to the group "alkyl-O—" (e.g., $C_1$-$C_3$ alkoxy or $C_1$-$C_6$ alkoxy). Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-$S(O)_2$—". "Alkylsulfonylalkyl" refers to -alkyl-$S(O)_2$-alkyl.

"Acyl" refers to a group $—C(O)R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to the group $—C(O)NR^yR^z$ and an "N-amido" group which refers to the group $—NR^yC(O)R^z$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to the group $-NR^yR^z$ wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to $-C(NR^y)(NR^z_2)$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclyl, the resulting ring system is heterocyclyl regardless of the point of attachment.

"Arylalkyl" or "Aralkyl" refers to the group "aryl-alkyl-", such as benzyl.

"Carbamoyl" refers to both an "O-carbamoyl" group which refers to the group $-O-C(O)NR^yR^z$ and an "N-carbamoyl" group which refers to the group $-NR^yC(O)OR^z$, wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both $-OC(O)R^x$ and $-C(O)OR^x$, wherein $R^x$ is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), 3 to 7 ring carbon atoms (i.e., $C_3$-$C_7$ cycloalkyl), or 3 to 6 ring carbon atoms (i.e., $C_3$-$C_6$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-".

"Guanidino" refers to $-NR^yC(=NR^z)(NR^yR^z)$, wherein each $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Hydrazino" refers to $-NHNH_2$.

"Imino" refers to a group $-C(NR^y)R^z$, wherein $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

"Imido" refers to a group $-C(O)NR^yC(O)R^z$, wherein $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" refers to atoms occupying group VIIA of the periodic table, such as fluoro (fluorine), chloro (chlorine), bromo (bromine) or iodo (iodine).

"Haloalkyl" refers to an unbranched or branched alkyl group as defined above, wherein one or more (e.g., 1 to 6, or 1 to 3) hydrogen atoms are replaced by a halogen. For example, halo-$C_1$-$C_3$ alkyl refers to an alkyl group of 1 to 3 carbons wherein at least one hydrogen atom is replaced by a halogen. Where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, or 1 to 3) hydrogen atoms are replaced by a halogen.

"Hydroxyalkyl" refers to an alkyl group as defined above, wherein one or more (e.g., 1 to 6, or 1 to 3) hydrogen atoms are replaced by a hydroxy group. The term "hydroxy-$C_1$-$C_3$ alkyl" refers to a one to three carbon alkyl chain where one or more hydrogens on any carbon is replaced by a hydroxy group, in particular, one hydrogen on one carbon of the chain is replaced by a hydroxy group. Non-limiting examples of hydroxyalkyl include $-CH_2OH$, $-CH_2CH_2OH$, and $-C(CH_3)_2CH_2OH$.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. In certain embodiments, the heteroalkyl can have 1 to 3 carbon atoms (i.e., $C_1$-$C_3$ heteroalkyl) or 1 to 6 carbon atoms (i.e., $C_1$-$C_6$ heteroalkyl), and one or more (e.g., 1, 2, or 3) heteroatoms or heteroatomic groups. The term "heteroalkyl" includes unbranched or branched saturated chain having carbon and heteroatoms. By way of example, 1, 2 or 3 carbon atoms of the alkyl group in the "heteroalkyl" may be independently replaced with the same or different heteroatomic group. Heteroatomic groups include, but are not limited to, $-NR^y-$, $-O-$, $-S-$, $-S(O)-$, $-S(O)_2-$, and the like, wherein R is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., $-CH_2OCH_3$, $-CH(CH_3)OCH_3$, $-CH_2CH_2OCH_3$, $-CH_2CH_2OCH_2CH_2OCH_3$, etc.), thioethers (e.g., $-CH_2SCH_3$, $-CH(CH_3)SCH_3$, $-CH_2CH_2SCH_3$, $-CH_2CH_2SCH_2CH_2SCH_3$, etc.), sulfones (e.g., $-CH_2S(O)_2CH_3$, $-CH(CH_3)S(O)_2CH_3$, $-CH_2CH_2S(O)_2CH_3$, $-CH_2CH_2S(O)_2C\ H_2CH_2OCH_3$, etc.) and amines (e.g., $-CH_2NR^yCH_3$, $-CH(CH_3)NR^yCH_3$, $-CH_2CH_2NR^yCH_3$, $-CH_2CH_2NR^yCH_2CH_2NR^yCH_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Hydroxyalkoxy" refers to the group "-alkoxy-hydroxy," (e.g., hydroxy-$C_1$-$C_3$ alkoxy, hydroxy-$C_1$-$C_{10}$ alkoxy). The term "hydroxy-$C_1$-$C_3$ alkoxy" refers to an alkoxy group containing a one to three carbon alkyl moiety wherein one or more hydrogens on any carbon is replaced by a hydroxy group, in particular, one hydrogen on one carbon of the chain is replaced by a hydroxy group. The term "hydroxy-$C_1$-$C_{10}$ alkoxy" refers to an alkoxy group containing a one to ten carbon alkyl chain wherein one or more hydrogens on any carbon is replaced by a hydroxy group, in particular, one hydrogen on one carbon of the chain is replaced by a hydroxy group. Non-limiting examples of hydroxyalkoxy include $—O—CH_2CH_2OH$, $—OCH_2C(CH_3)_{20}H$, $—OCH_2CH(CH_3)OH$, $—OCH(CH_3)CH_2OH$, $—O—CH_2CH(CH(CH_3)_2)OH$, and $—OCH_2CH(CH_2CH_3)OH$.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_1$-$C_{20}$ heteroaryl), 3 to 12 ring carbon atoms (i.e., $C_3$-$C_{12}$ heteroaryl), or 3 to 8 carbon ring atoms (i.e., $C_3$-$C_5$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems (i.e., 9-10 membered heteroaryl), 5-10 membered ring systems (i.e., 5-10 membered heteroaryl), 5-7 membered ring systems (i.e., 5-7 membered heteroaryl), 5-6 membered ring systems (i.e., 5-6 membered heteroaryl), or 4-6 membered ring systems (i.e., 4-6 membered heteroaryl), each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_2$-$C_{20}$ heterocyclyl), 2 to 12 ring carbon atoms (i.e., $C_2$-$C_{12}$ heterocyclyl), 2 to 10 ring carbon atoms (i.e., $C_2$-$C_{10}$ heterocyclyl), 2 to 8 ring carbon atoms (i.e., $C_2$-$C_8$ heterocyclyl), 3 to 12 ring carbon atoms (i.e., $C_3$-$C_{12}$ heterocyclyl), 3 to 8 ring carbon atoms (i.e., $C_3$-$C_8$ heterocyclyl), or 3 to 6 ring carbon atoms (i.e., $C_3$-$C_6$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. When the heterocyclyl ring contains 4- to 6-ring atoms, it is also referred to herein as a 4- to 6-membered heterocyclyl. When the heterocyclyl ring contains 5- to 7-ring atoms, it is also referred to herein as a 5- to 7-membered heterocyclyl. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-."

"Oxime" refers to the group $—CR^y(=NOH)$ wherein $R^y$ is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group $—S(O)_2R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)$R^y$, where $R^y$ is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, 1 to 4, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5, 1 to 4, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —$NHNH_2$, =$NNH_2$, imino, imido, hydroxy, oxo, oxime, nitro, sulfonyl, sulfinyl, alkylsulfonyl, alkylsulfinyl, thiocyanate, —S(O)OH, —$S(O)_2OH$, sulfonamido, thiol, thioxo, N-oxide or —$Si(R^y)_3$, wherein each $R^y$ is independently hydrogen, alkyl, alkenyl, alkynyl, heteroalkyl, cycloalkyl, aryl, heteroaryl or heterocyclyl.

In certain embodiments, "substituted" includes any of the above alkyl, alkenyl, alkynyl, cycloalkyl, heterocyclyl, aryl or heteroaryl groups in which one or more (e.g., 1 to 5, 1 to 4, or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, —$OC(=O)NR^gR^h$, —$OR^g$, —SR, —$S(=O)R^g$, —$S(=O)_2R^g$, —$OS(=O)_{1-2}R^g$, —$S(=O)_{1-2}OR^g$, —$NR^gS(=O)_{1-2}NR^gR^h$, =$NSO_2R$, =$NOR^g$, —$S(=O)_{1-2}NR^gR^h$, —$SF_5$, —$SCF_3$ or —$OCF_3$. In certain embodiments, "substituted" also means any of the above groups in which one or more (e.g., 1 to 5, 1 to 4, or 1 to 3) hydrogen atoms are replaced with —$C(=O)R^g$, —$C(=O)OR^g$, —$C(=O)NR^gR^h$, —$CH_2SO_2R^9$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5, 1 to 4, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^L$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to four. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$ $^{18}F$, $^{36}Cl$, $^{123}$ and $^{125}I$, respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$ (substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) may be reduced in vivo to a —$CH_2OH$ moiety.

Use of the word "inhibitor," "inhibit" or "inhibition," herein refers to activity of a compound of Formula I or a pharmaceutically acceptable salt on ferroportin, unless specified otherwise. By "inhibit" herein is meant to decrease the activity of ferroportin, as compared to the activity of ferroportin in the absence of the compound. In some embodiments, the term "inhibit" means a decrease in ferroportin activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in ferroportin activity of about 5% to about 25%, about 25% to about 50%, about 50% to about 75%, or about 75% to 100%. In some embodiments, inhibit means a decrease in ferroportin activity of about 95% to 100%, e.g., a decrease in activity of 95%, 96%, 97%, 98%, 99%, or 100%. Such decreases can be measured using a variety of techniques that would be recognizable by one of skill in the art, including in vitro assays.

As used herein, the term "ferroportin inhibitor" and the like refers to a compound that reduces, inhibits, or otherwise diminishes one or more of the biological activities of ferroportin, for instance by inducing internalization of ferroportin. The activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of ferroportin compared to an appropriate control.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one of ordinary skill in the art.

Additional definitions may also be provided below as appropriate.

II. Compounds

In certain embodiments, the subject matter described herein is directed to a compound of Formula I.

(I)

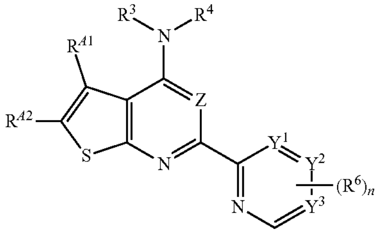

or a pharmaceutically acceptable salt thereof, wherein, $R^{A1}$ and $R^{A2}$ are each independently selected from the group consisting of hydrogen, $C_1$-$C_3$ alkyl, halogen, and 5- or 6-membered heteroaryl;

Z is N or CH;

$R^6$, in each instance, is selected from the group consisting of halogen, hydroxy, $C_1$-$C_3$ alkoxy, $C_1$-$C_3$ alkyl, and $C_3$-$C_6$ cycloalkyl;

n is 0, 1, 2, or 3;

$Y_1$, $Y_2$, and $Y_3$ are each independently selected from the group consisting of N, CH, and C (when $R^6$ is attached thereto);

$R^3$ is selected from the group consisting of hydrogen, $C_1$-$C_3$ alkyl, and hydroxy-$C_1$-$C_3$ alkyl;

$R^4$ is selected from the group consisting of

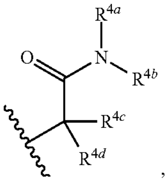,
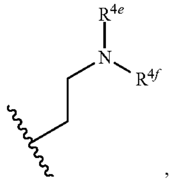, and
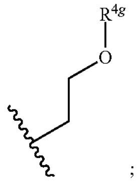;

wherein, $R^{4a}$ is hydrogen or $C_1$-$C_6$ alkyl;

$R^{4b}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl; or $R^{4a}$ and $R^{4b}$ taken together with the atom to which each is attached form a 5- to 7-membered heterocyclyl;

$R^{4c}$ is selected from the group consisting of hydrogen, $C_1$-$C_3$ alkyl, $C_3$-$C_6$ cycloalkyl, and hydroxy-$C_1$-$C_3$ alkyl;

$R^{4d}$ is hydrogen or $C_1$-$C_3$ alkyl; or $R^{4c}$ and $R^{4d}$ taken together with the atom to which each is attached form a $C_3$-$C_6$ cycloalkyl or 5- to 7-membered heterocyclyl;

$R^{4e}$ is selected from the group consisting of hydrogen, $C_1$-$C_3$ alkyl, $C_5$-$C_{10}$ cycloalkyl, 5- to 7-membered heterocyclyl, and $C_6$-$C_{10}$ aryl;

$R^{4f}$ is hydrogen or $C_1$-$C_3$ alkyl; or $R^{4e}$ and $R^{4f}$ taken together with the atom to which each is attached form a 5- to 7-membered heterocyclyl;

$R^{4g}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl;

wherein the cycloalkyl, heterocyclyl, aryl, or heteroaryl of $R^{4b}$, $R^{4c}$, $R^{4e}$, and $R^{4g}$ is optionally substituted with one or two substituents, each independently selected from the group consisting of $C_1$-$C_6$ alkyl, hydroxy, and $C_1$-$C_3$ alkoxy;

and, wherein the compound of Formula (I) is not:

N-(2-methoxyethyl)-5,6-dimethyl-2-(pyridin-2-yl)thieno[2,3-d]pyrimidin-4-amine;

or, a salt thereof.

In certain embodiments, the subject matter described herein is directed to a compound of Formula I:

(I)

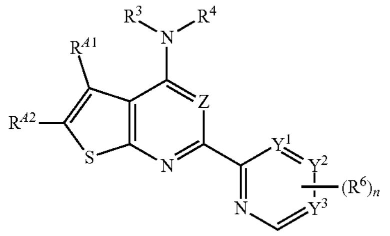

or a pharmaceutically acceptable salt thereof, wherein, $R^{A1}$ and $R^{A2}$ are each independently selected from the group consisting of hydrogen, $C_1$-$C_3$ alkyl, halogen, and 5- or 6-membered heteroaryl;

Z is N or CH;

$R^6$, in each instance, is selected from the group consisting of halogen, hydroxy, $C_1$-$C_3$ alkoxy, $C_1$-$C_3$ alkyl, and $C_3$-$C_6$ cycloalkyl;

n is 0, 1, 2, or 3;

$Y_1$, $Y_2$, and $Y_3$ are each independently selected from the group consisting of N, CH, and C (when $R^6$ is attached thereto);

$R^3$ is selected from the group consisting of hydrogen, $C_1$-$C_3$ alkyl, and hydroxy-$C_1$-$C_3$ alkyl;

$R^4$ is selected from the group consisting of

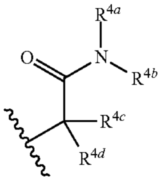,
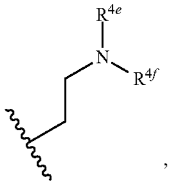, and
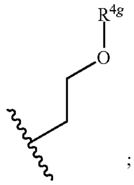;

wherein, $R^{4a}$ is hydrogen or $C_1$-$C_6$ alkyl;

$R^{4b}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl; or $R^{4a}$ and $R^{4b}$ taken together with the atom to which each is attached form a 5- to 7-membered heterocyclyl;

$R^{4c}$ is selected from the group consisting of hydrogen, $C_1$-$C_3$ alkyl, $C_3$-$C_6$ cycloalkyl, and hydroxy-$C_1$-$C_3$ alkyl;

$R^{4d}$ is hydrogen or $C_1$-$C_3$ alkyl; or $R^{4c}$ and $R^{4d}$ taken together with the atom to which each is attached form a $C_3$-$C_6$ cycloalkyl or 5- to 7-membered heterocyclyl;

$R^{4e}$ is selected from the group consisting of hydrogen, $C_1$-$C_3$ alkyl, $C_5$-$C_{10}$ cycloalkyl, 5- to 7-membered heterocyclyl, and $C_6$-$C_{10}$ aryl;

$R^{4f}$ is hydrogen or $C_1$-$C_3$ alkyl; or $R^{4e}$ and $R^{4f}$ taken together with the atom to which each is attached form a 5- to 7-membered heterocyclyl;

$R^{4g}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl;

wherein the cycloalkyl, heterocyclyl, aryl, or heteroaryl of $R^{4b}$, $R^{4c}$, $R^{4e}$, and $R^{4g}$ is optionally substituted with one or two substituents, each independently selected from the group consisting of $C_1$-$C_6$ alkyl, hydroxy, and $C_1$-$C_3$ alkoxy;

provided that when $R^3$ is methyl, $R^{A1}$ and $R^{A2}$ are each methyl, n is 0, $Y^1$, $Y^2$, and $Y^3$ are each CH, and $R^4$ is

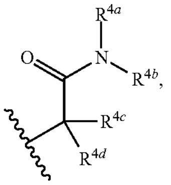

wherein $R^{4c}$ and $R^{4d}$ are each hydrogen, $R^{4a}$ is hydrogen, and $R^{4b}$ is phenyl, said phenyl is optionally substituted with one or two substituents, each independently selected from the group consisting of $C_1$-$C_6$ alkyl and hydroxy; or, said phenyl is optionally substituted twice with $C_1$-$C_3$ alkoxy; and, wherein the compound of Formula (I) is not:

N-(2-methoxyethyl)-5,6-dimethyl-2-(pyridin-2-yl)thieno[2,3-d]pyrimidin-4-amine; or, a salt thereof.

In certain embodiments, the subject matter described herein is directed to a compound of Formula I:

(I)

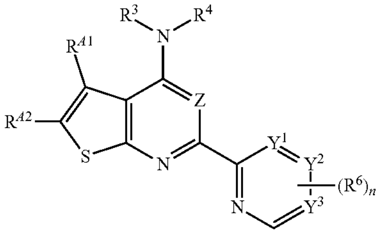

or a pharmaceutically acceptable salt thereof, wherein, $R^{A1}$ and $R^{A2}$ are each independently selected from the group consisting of hydrogen, $C_1$-$C_3$ alkyl, halogen, and 5- or 6-membered heteroaryl;

Z is N or CH;

$R^6$, in each instance, is selected from the group consisting of halogen, hydroxy, $C_1$-$C_3$ alkoxy, $C_1$-$C_3$ alkyl, and $C_3$-$C_6$ cycloalkyl;

n is 0, 1, 2, or 3;

$Y_1$, $Y_2$, and $Y_3$ are each independently selected from the group consisting of N, CH, and C (when $R^6$ is attached thereto);

$R^3$ is selected from the group consisting of hydrogen, $C_1$-$C_3$ alkyl, and hydroxy-$C_1$-$C_3$ alkyl;

$R^4$ is selected from the group consisting of

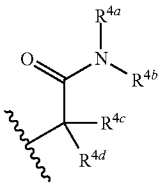 , 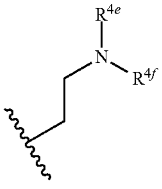 , and 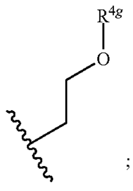 ;

wherein, $R^{4a}$ is hydrogen or $C_1$-$C_6$ alkyl;

$R^{4b}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl; or $R^{4a}$ and $R^{4b}$ taken together with the atom to which each is attached form a 5- to 7-membered heterocyclyl;

$R^{4c}$ is selected from the group consisting of hydrogen, $C_1$-$C_3$ alkyl, $C_3$-$C_6$ cycloalkyl, and hydroxy-$C_1$-$C_3$ alkyl;

$R^{4d}$ is hydrogen or $C_1$-$C_3$ alkyl; or $R^{4c}$ and $R^{4d}$ taken together with the atom to which each is attached form a $C_3$-$C_6$ cycloalkyl or 5- to 7-membered heterocyclyl;

$R^{4e}$ is selected from the group consisting of hydrogen, $C_1$-$C_3$ alkyl, $C_5$-$C_{10}$ cycloalkyl, 5- to 7-membered heterocyclyl, and $C_6$-$C_{10}$ aryl;

$R^{4f}$ is hydrogen or $C_1$-$C_3$ alkyl; or $R^{4e}$ and $R^{4f}$ taken together with the atom to which each is attached form a 5- to 7-membered heterocyclyl;

$R^{4g}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl;

wherein the cycloalkyl, heterocyclyl, aryl, or heteroaryl of $R^{4b}$, $R^{4c}$, $R^{4e}$, and $R^{4g}$ is optionally substituted with one or two substituents, each independently selected from the group consisting of $C_1$-$C_6$ alkyl, hydroxy, and $C_1$-$C_3$ alkoxy;

and, wherein the compound of Formula (I) is not:

N-(2-methoxyethyl)-5,6-dimethyl-2-(pyridin-2-yl)thieno[2,3-d]pyrimidin-4-amine; or 2-{[5,6-dimethyl-2-(pyridin-2-yl)thieno[2,3-d]pyrimidin-4-yl](methyl)amino}-N-(4-methoxyphenyl)acetamide; or, a salt thereof.

In certain embodiments, the subject matter described herein is directed to a compound of Formula I:

(I)

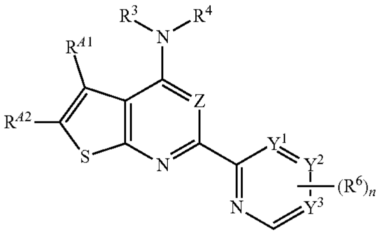

or a pharmaceutically acceptable salt thereof, wherein, $R^{A1}$ and $R^{A2}$ are each independently selected from the group consisting of hydrogen, $C_1$-$C_3$ alkyl, halogen, and 5- or 6-membered heteroaryl;

Z is N or CH;

$R^6$, in each instance, is selected from the group consisting of halogen, hydroxy, $C_1$-$C_3$ alkoxy, hydroxy-$C_1$-$C_{10}$ alkoxy, —O—($C_1$-$C_6$ alkyl)$_y$-$R^{bb}$, $C_1$-$C_3$ alkyl, and $C_3$-$C_6$ cycloalkyl;

$R^{bb}$ is 4- to 7-membered monocyclic or bridged heterocyclyl, 5- or 6-membered monocyclic heteroaryl or —$NR^GR^H$; wherein, said heterocyclyl and heteroaryl is optionally substituted with one or two substituents, each independently selected from the group consisting of hydroxy, halogen, halo-$C_1$-$C_3$ alkyl, $C_1$-$C_3$ alkoxy, and $C_1$-$C_3$ alkyl, and $R^G$ and $R^H$ are each independently hydrogen or $C_1$-$C_3$ alkyl;

y is 0 or 1;

n is 0, 1, 2, or 3;

$Y^1$ is absent or present, $Y^1$, if present, and $Y_2$, and $Y_3$ are each independently selected from the group consisting of N, CH, and C (when $R^6$ is attached thereto);

$R^3$ is selected from the group consisting of hydrogen, $C_1$-$C_3$ alkyl, and hydroxy-$C_1$-$C_3$ alkyl;

$R^4$ is selected from the group consisting of

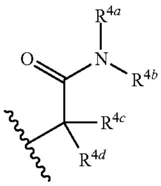
,
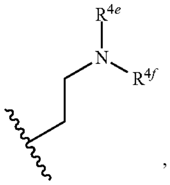
, and
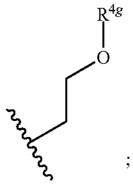
;

wherein, $R^{4a}$ is hydrogen or $C_1$-$C_6$ alkyl;

$R^{4b}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl; or $R^{4a}$ and $R^{4b}$ taken together with the atom to which each is attached form a 5- to 7-membered heterocyclyl;

$R^{4c}$ is selected from the group consisting of hydrogen, $C_1$-$C_3$ alkyl, $C_3$-$C_6$ cycloalkyl, and hydroxy-$C_1$-$C_3$ alkyl;

$R^{4d}$ is hydrogen or $C_1$-$C_3$ alkyl; or $R^{4c}$ and $R^{4d}$ taken together with the atom to which each is attached form a $C_3$-$C_6$ cycloalkyl or 5- to 7-membered heterocyclyl;

$R^{4e}$ is selected from the group consisting of hydrogen, $C_1$-$C_3$ alkyl, $C_5$-$C_{10}$ cycloalkyl, 5- to 7-membered heterocyclyl, and $C_6$-$C_{10}$ aryl;

$R^{4f}$ is hydrogen or $C_1$-$C_3$ alkyl; or $R^{4e}$ and $R^{4f}$ taken together with the atom to which each is attached form a 5- to 7-membered heterocyclyl;

$R^{4g}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl;

wherein the cycloalkyl, heterocyclyl, aryl, or heteroaryl of $R^{4b}$, $R^{4c}$, $R^{4e}$, and $R^{4g}$ is optionally substituted with one or two substituents, each independently selected from the group consisting of halogen, $C_1$-$C_6$ alkyl, halo $C_1$-$C_6$ alkyl, hydroxy, and $C_1$-$C_3$ alkoxy;

and, wherein the compound of Formula (I) is not:

N-(2-methoxyethyl)-5,6-dimethyl-2-(pyridin-2-yl)thieno[2,3-d]pyrimidin-4-amine;

or, a salt thereof.

In certain embodiments, $Y^1$ is absent or present.

In certain embodiments, y is 0.

In certain embodiments, y is 1.

In certain embodiments, Z is N.

In certain embodiments, $R^3$ is $C_1$-$C_3$ alkyl.

In certain embodiments, $R^3$ is methyl.

In certain embodiments, $Y^1$, $Y^2$, and $Y^3$ are each CH.

In certain embodiments, n is 0.

In certain embodiments, $R^{A1}$ and $R^{A2}$ are each independently $C_1$-$C_3$ alkyl.

In certain embodiments, $R^{A1}$ and $R^{A2}$ are each methyl.

In certain embodiments, $R^4$ is

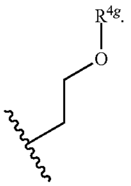

In certain embodiments, $R^{4g}$ is hydrogen or $C_1$-$C_3$ alkyl.

In certain embodiments, $R^{4g}$ is methyl.

In certain embodiments, $R^4$ is

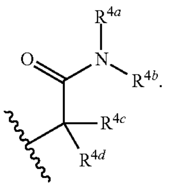

In certain embodiments, $R^{4a}$ is hydrogen or $C_1$-$C_3$ alkyl.

In certain embodiments, $R^{4a}$ is hydrogen.

In certain embodiments, $R^{4a}$ is methyl.

In certain embodiments, $R^{4b}$ is $C_1$-$C_3$ alkyl.

In certain embodiments, $R^{4b}$ is methyl.

In certain embodiments, $R^{4b}$ is phenyl or 5 or 6-membered heteroaryl, optionally substituted with one or two substituents each independently selected from the group consisting of $C_1$-$C_6$ alkyl, hydroxy, and $C_1$-$C_3$ alkoxy.

In certain embodiments, $R^{4b}$ is phenyl, optionally substituted with $C_1$-$C_3$ alkoxy.

In certain embodiments, $R^{4b}$ is phenyl, substituted once with methoxy.

In certain embodiments, $R^{4b}$ is 5- or 6-membered heteroaryl.

In certain embodiments, $R^{4'}$ and $R^{4d}$ are each hydrogen.

In certain embodiments, $R^{4b}$ is pyridinyl.

In certain embodiments, $R^4$ is

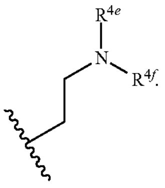

In certain embodiments, $R^{4e}$ and $R^{4f}$ taken together with the atom to which each is attached form a 5- to 7-membered heterocyclyl, optionally substituted with one or two substituents each independently selected from the group consisting of $C_1$-$C_6$ alkyl, hydroxy, and $C_1$-$C_3$ alkoxy.

In certain embodiments, $R^{4e}$ and $R^{4f}$ taken together with the atom to which each is attached form a pyrrolidonyl.

In certain embodiments, where $R^4$ is

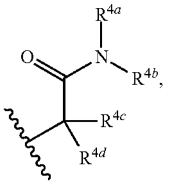

$R^6$ is —O—$CH_2CH_2$—OH. In some compounds of these embodiments, $R^{4a}$, $R^{4c}$, and $R^{4d}$ are each hydrogen; and, $R^{4b}$ is selected from the group consisting of pyridinyl, phenyl, cyclopropyl and $C_1$-$C_6$ alkyl, wherein the pyridinyl, phenyl or cyclopropyl of $R^{4b}$ is optionally substituted with one or two substitutents selected from the group consisting of fluoro, methyl, —$CF_3$ and methoxy.

In certain embodiments, where $R^4$ is

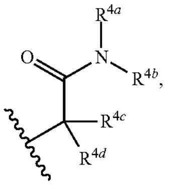

$R^6$ is —O—$CH_2CH_2$—Rb. In some compounds of these embodiments, $R^{4a}$, $R^{4c}$, and $R^{4d}$ are each hydrogen; and, $R^{4b}$ is selected from the group consisting of pyridinyl, phenyl, cyclopropyl and $C_1$-$C_6$ alkyl, wherein the pyridinyl, phenyl or cyclopropyl of $R^{4b}$ is optionally substituted with one or two substitutents selected from the group consisting of fluoro, methyl, —$CF_3$ and methoxy. In some compounds of these embodiments, $R^{bb}$ is selected from the group consisting of —N$(CH_3)_2$, morpholinyl, piperazinyl, tetrahydropyrrolyl, imidazolyl, and

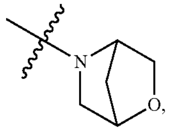

wherein, the morpholinyl, piperazinyl, imidazolyl or tetrahydropyrrolyl of $R^{bb}$ is optionally substituted with one or two substitutents selected from the group consisting of halogen, $C_1$-$C_6$ alkyl, halo $C_1$-$C_6$ alkyl and $C_1$-$C_6$ alkoxy.

In certain embodiments, $Y^1$ is absent. In some compounds of these embodiments, the compounds have a structure of Formula Ia:

Ia

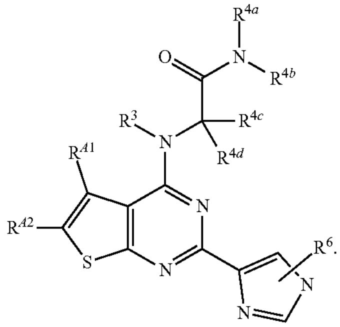

The subject matter described herein includes the following compounds in Table 1, or pharmaceutically acceptable salts thereof:

TABLE 1

| Compound No. | Structure | IUPAC Name | Mass Found (M + 1) |
|---|---|---|---|
| 1 | 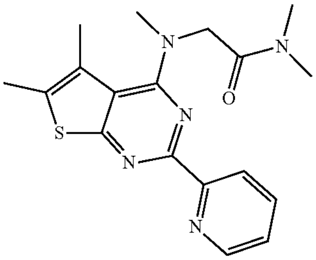 | 2-{[5,6-dimethyl-2-(pyridin-2-yl)thieno[2,3-d]pyrimidin-4-yl](methyl)amino}-N,N-dimethylacetamide | 356.3 |
| 2 | 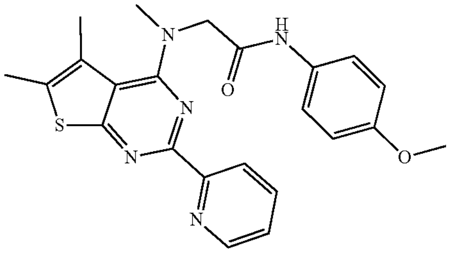 | 2-{[5,6-dimethyl-2-(pyridin-2-yl)thieno[2,3-d]pyrimidin-4-yl](methyl)amino}-N-(4-methoxyphenyl)acetamide | 434 |

TABLE 1-continued

| Compound No. | Structure | IUPAC Name | Mass Found (M + 1) |
|---|---|---|---|
| 3 | 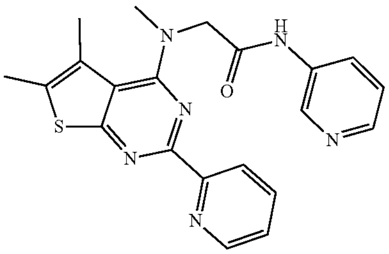 [SMILES: Cc1sc2nc(-c3ccccn3)nc(N(C)CC(=O)Nc3cccnc3)c2c1C] | 2-{[5,6-dimethyl-2-(pyridin-2-yl)thieno[2,3-d]pyrimidin-4-yl](methyl)amino}-N-(pyridin-3-yl)acetamide | 405.1 |
| 4 | 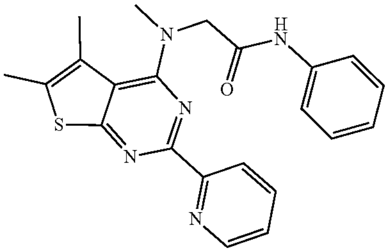 [SMILES: Cc1sc2nc(-c3ccccn3)nc(N(C)CC(=O)Nc3ccccc3)c2c1C] | 2-{[5,6-dimethyl-2-(pyridin-2-yl)thieno[2,3-d]pyrimidin-4-yl](methyl)amino}-N-phenylacetamide | 404.2 |
| 5 | 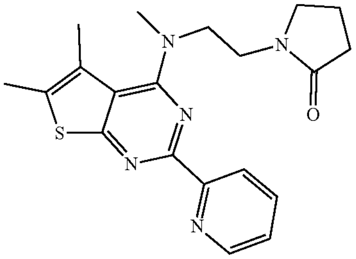 [SMILES: Cc1sc2nc(-c3ccccn3)nc(N(C)CCN3CCCC3=O)c2c1C] | 1-(2-{[5,6-dimethyl-2-(pyridin-2-yl)thieno[2,3-d]pyrimidin-4-yl](methyl)amino}ethyl)pyrrolidin-2-one | 382.9 |
| 6 | 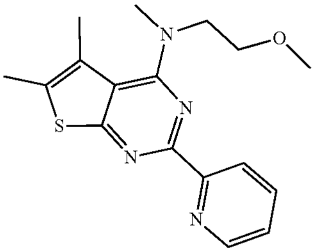 | N-(2-methoxyethyl)-N-5,6-trimethyl-2-(pyridin-2-yl)thieno[2,3-d]pyrimidin-4-amine | 328.6 |
| 7 | 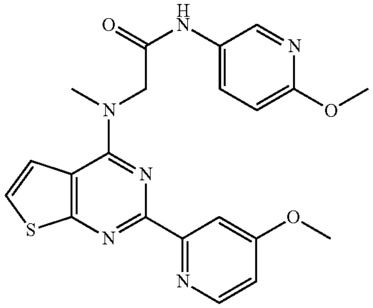 [SMILES: COc1ccnc(-c2nc(N(C)CC(=O)Nc3ccc(OC)nc3)c3ccsc3n2)c1] | 2-{[2-(4-methoxypyridin-2-yl)thieno[2,3-d]pyrimidin-4-yl](methyl)amino}-N-(6-methoxypyridin-3-yl)acetamide | 437.2 |

TABLE 1-continued

| Compound No. | Structure | IUPAC Name | Mass Found (M + 1) |
|---|---|---|---|
| 8 | 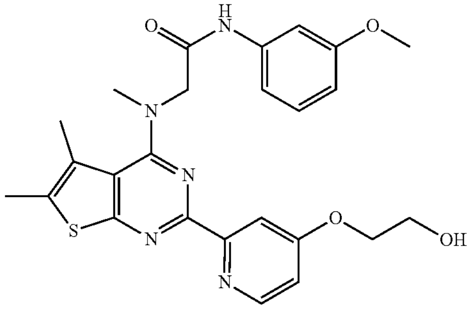 [SMILES: COc1cccc(NC(=O)CN(C)c2nc(-c3cc(OCCO)ccn3)nc3sc(C)c(C)c23)c1] | 2-({2-[4-(2-hydroxyethoxy)pyridin-2-yl]-5,6-dimethylthieno[2,3-d]pyrimidin-4-yl}(methyl)amino)-N-(3-methoxyphenyl)acetamide | 494.2 |
| 9 | 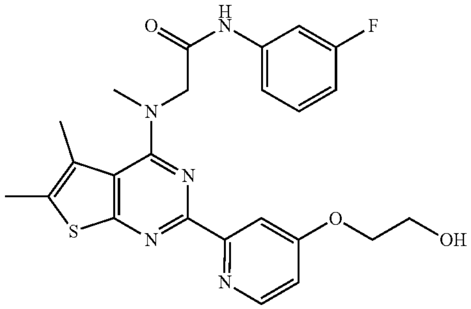 [SMILES: Cc1sc2nc(-c3cc(OCCO)ccn3)nc(N(C)CC(=O)Nc3cccc(F)c3)c2c1C] | N-(3-fluorophenyl)-2-({2-[4-(2-hydroxyethoxy)pyridin-2-yl]-5,6-dimethylthieno[2,3-d]pyrimidin-4-yl}(methyl)amino)acetamide | 482.2 |
| 10 | 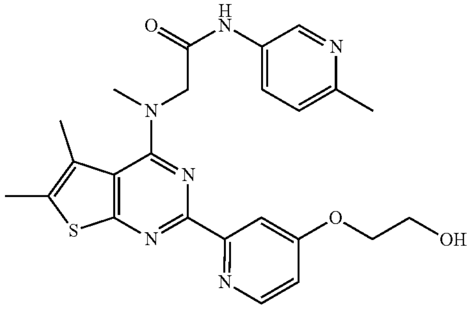 [SMILES: Cc1ccc(NC(=O)CN(C)c2nc(-c3cc(OCCO)ccn3)nc3sc(C)c(C)c23)cn1] | 2-({2-[4-(2-hydroxyethoxy)pyridin-2-yl]-5,6-dimethylthieno[2,3-d]pyrimidin-4-yl}(methyl)amino)-N-(6-methylpyridin-3-yl)acetamide | 479.2 |
| 11 | 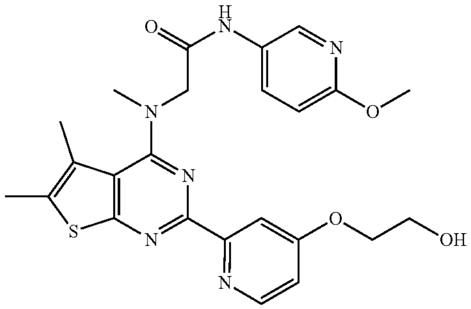 [SMILES: COc1ccc(NC(=O)CN(C)c2nc(-c3cc(OCCO)ccn3)nc3sc(C)c(C)c23)cn1] | 2-({2-[4-(2-hydroxyethoxy)pyridin-2-yl]-5,6-dimethylthieno[2,3-d]pyrimidin-4-yl}(methyl)amino)-N-(6-methylpyridin-3-yl)acetamide | 422.2 |
| 12 | 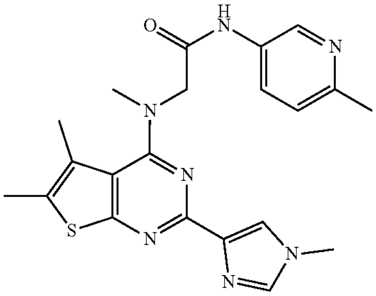 | 2-{[5,6-dimethyl-2-(1-methyl-1H-imidazol-4-yl)thieno[2,3-d]pyrimidin-4-yl](methyl)amino}-N-(6-methylpyridin-3-yl)acetamide | 422.2 |

TABLE 1-continued

| Compound No. | Structure | IUPAC Name | Mass Found (M + 1) |
|---|---|---|---|
| 13 | 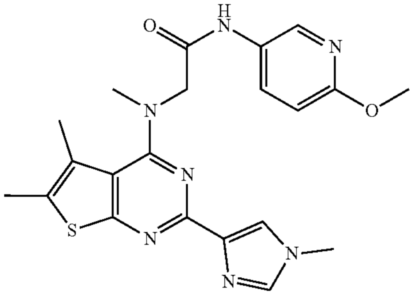 | 2-{[5,6-dimethyl-2-(1-methyl-1H-imidazol-4-yl)thieno[2,3-d]pyrimidin-4-yl](methyl)amino}-N-(6-methoxypyridin-3-yl)acetamide | 438.1 |
| 14 | 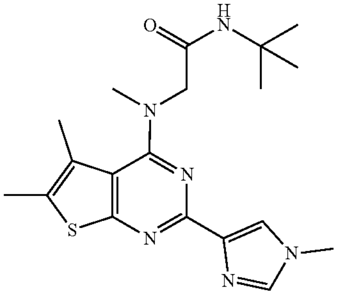 | N-tert-butyl-2-{[5,6-dimethyl-2-(1-methyl-1H-imidazol-4-yl)thieno[2,3-d]pyrimidin-4-yl](methyl)amino}acetamide | 387.2 |
| 15 | 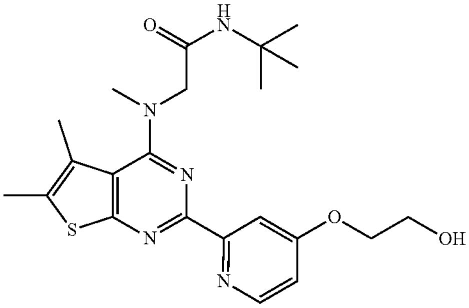 [SMILES: Cc1sc2nc(-c3cc(OCCO)ccn3)nc(N(C)CC(=O)NC(C)(C)C)c2c1C] | N-tert-butyl-2-({2-[4-(2-hydroxyethoxy)pyridin-2-yl]-5,6-dimethylthieno[2,3-d]pyrimidin-4-yl}(methyl)amino)acetamide | 444.2 |
| 16 | 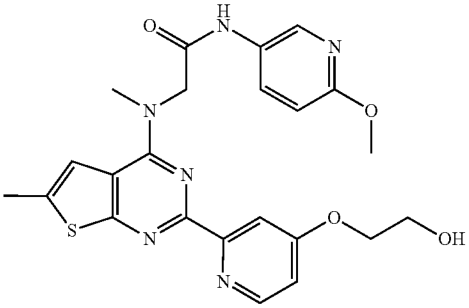 [SMILES: COc1ccc(NC(=O)CN(C)c2nc(-c3cc(OCCO)ccn3)nc3sc(C)cc23)cn1] | 2-({2-[4-(2-hydroxyethoxy)pyridin-2-yl]-6-methylthieno[2,3-d]pyrimidin-4-yl}(methyl)amino)-N-(6-methoxypyridin-3-yl)acetamide | 481.1 |
| 17 | 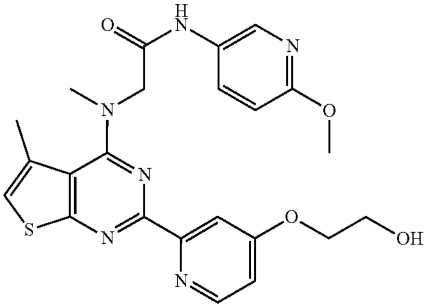 [SMILES: COc1ccc(NC(=O)CN(C)c2nc(-c3cc(OCCO)ccn3)nc3scc(C)c23)cn1] | 2-({2-[4-(2-hydroxyethoxy)pyridin-2-yl]-5-methylthieno[2,3-d]pyrimidin-4-yl}(methyl)amino)-N-(6-methoxypyridin-3-yl)acetamide | 481.2 |

TABLE 1-continued

| Compound No. | Structure | IUPAC Name | Mass Found (M + 1) |
|---|---|---|---|
| 18 | 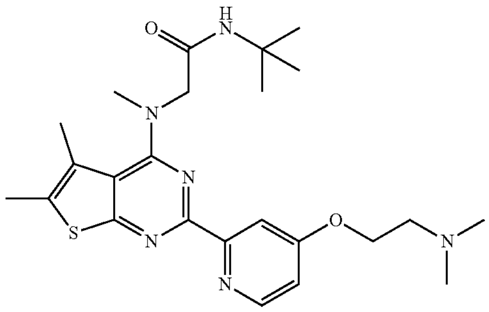 | N-tert-butyl-2-[(2-{4-[2-(dimethylamino)ethoxy]pyridin-2-yl}-5,6-dimethylthieno[2,3-d]pyrimidin-4-yl)(methyl)amino]acetamide | 471.3 |
| 19 | 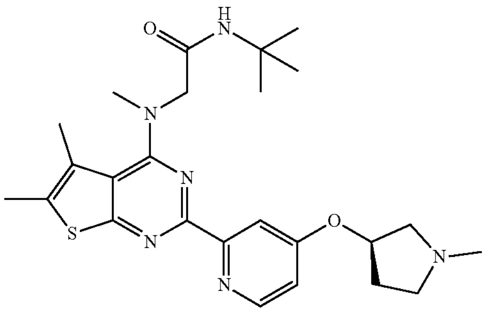 | N-tert-butyl-2-{[5,6-dimethyl-2-(4-{[(3R)-1-methylpyrrolidin-3-yl]oxy}pyridin-2-yl)thieno[2,3-d]pyrimidin-4-yl](methyl)amino}acetamide | 483.3 |
| 20 | 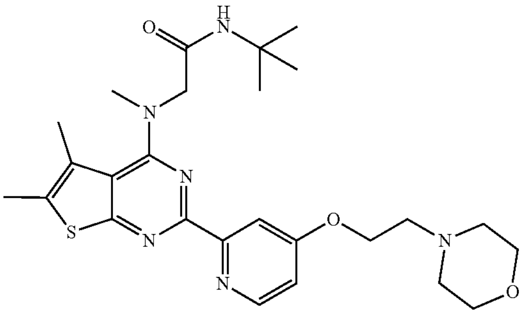 [SMILES: Cc1sc2nc(-c3cc(OCCN4CCOCC4)ccn3)nc(N(C)CC(=O)NC(C)(C)C)c2c1C] | N-tert-butyl-2-[(5,6-dimethyl-2-{4-[2-(morpholin-4-yl)ethoxy]pyridin-2-yl}thieno[2,3-d]pyrimidin-4-yl)(methyl)amino]acetamide | 513.3 |
| 21 | 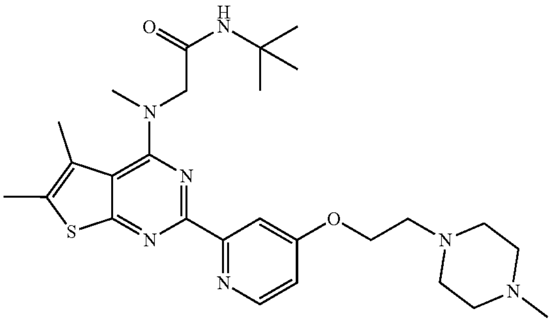 | N-tert-butyl-2-[(5,6-dimethyl-2-{4-[2-(4-methylpiperazin-1-yl)ethoxy]pyridin-2-yl}thieno[2,3-d]pyrimidin-4-yl)(methyl)amino]acetamide | 526.4 |

TABLE 1-continued

| Compound No. | Structure | IUPAC Name | Mass Found (M + 1) |
|---|---|---|---|
| 22 | 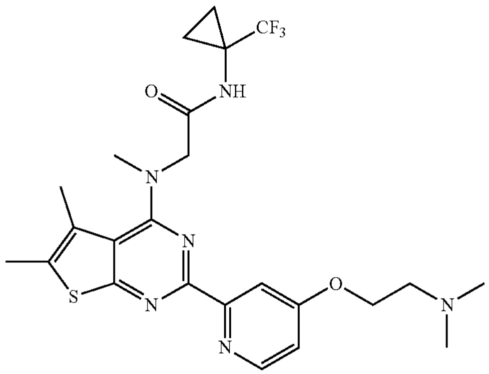 | 2-[(2-{4-[2-(dimethylamino)ethoxy]pyridin-2-yl}-5,6-dimethylthieno[2,3-d]pyrimidin-4-yl)(methyl)amino]-N-[1-(trifluoromethyl)cyclopropyl]acetamide | 523.3 |
| 23 | 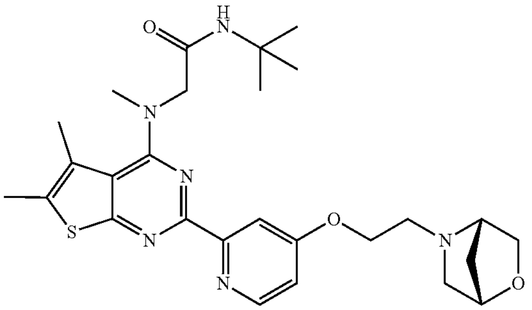 [SMILES: Cc1sc2nc(-c3cc(OCCN4C[C@@H]5C[C@H]4CO5)ccn3)nc(N(C)CC(=O)NC(C)(C)C)c2c1C] | N-tert-butyl-2-{[5,6-dimethyl-2-(4-{2-[(1S,4S)-2-oxa-5-azabicyclo[2.2.1]heptan-5-yl]ethoxy}pyridin-2-yl)thieno[2,3-d]pyrimidin-4-yl](methyl)amino}acetamide | 525.3 |
| 24 | 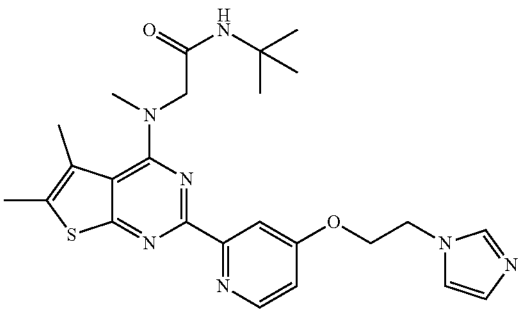 [SMILES: Cc1sc2nc(-c3cc(OCCn4ccnc4)ccn3)nc(N(C)CC(=O)NC(C)(C)C)c2c1C] | N-tert-butyl-2-[(2-{4-[2-(1H-imidazol-1-yl)ethoxy]pyridin-2-yl}-5,6-dimethylthieno[2,3-d]pyrimidin-4-yl)(methyl)amino]acetamide | 494.3 |

III. Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

IV. Methods of Treatment

In certain embodiments, the subject matter described herein is directed to a method of inhibiting iron transport mediated by ferroportin in a subject, comprising administering to a subject an effective amount of a compound of Formula I, or a pharmaceutically acceptable salt thereof.

In certain embodiments, the subject matter described herein is directed to a method of treating a subject afflicted with a disease related to or caused by reduced hepcidin levels, increased ferroportin levels, reduced sensitivity of ferroportin to hepcidin, increased iron levels, increased iron absorption, iron overload, increased erythropoiesis, stress erythropoiesis, or ineffective erythropoiesis, comprising administering to the subject an effective amount of a compound of Formula I.

In certain embodiments, the disease is related to or caused by reduced hepcidin levels, reduced sensitivity of ferroportin to hepcidin, a hemoglobinopathy, or iron overload.

In certain embodiments, the disease is related to or caused by reduced hepcidin levels or reduced sensitivity of ferroportin to hepcidin.

In certain embodiments, the disease is hemochromatosis.

In certain embodiments, the disease is related to or caused by a hemoglobinopathy.

In certain embodiments, the disease is thalassemia, hemoglobin E disease, hemoglobin H disease, or sickle cell disease.

In certain embodiments, the disease is sickle cell disease.

In certain embodiments, the sickle cell disease is sickle cell anemia.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The ferroportin inhibition activity of the compounds of Formula I and pharmaceutically acceptable salts thereof provide methods particularly suitable for the use in the inhibition of iron transport mediated by ferroportin. As such, the compounds of Formula I and pharmaceutically acceptable salts thereof are useful in the prophylaxis and/or treatment of a disease related to or caused by reduced hepcidin levels, increased ferroportin levels, reduced sensitivity of ferroportin to hepcidin, increased iron levels, increased iron absorption, iron overload, increased erythropoiesis, stress erythropoiesis, or ineffective erythropoiesis.

Further, the compounds of Formula I are suitable for the use in an adjunctive therapy by limiting the amount of iron available to pathogenic microorganisms, e.g. the siderophilic bacteria *Vibrio vulnificus* and *Yersinia enterocolitica*, and common pathogens (e.g. *Escherichia coli*), thereby preventing or treating infections, inflammation, sepsis, and septic shock caused by said pathogenic microorganisms.

In certain embodiments, the subject matter described herein is directed to a method of inhibiting iron transport mediated by ferroportin in a subject, comprising administering to the subject an effective amount of a compound of Formula I or a pharmaceutically acceptable salt thereof.

In certain embodiments, the subject matter described herein is directed to a method of treating a subject afflicted with a disease related to or caused by reduced hepcidin levels, increased ferroportin levels, reduced sensitivity of ferroportin to hepcidin, a hemoglobinopathy, increased iron levels, increased iron absorption, iron overload (e.g. due to blood transfusions), increased erythropoiesis, stress erythropoiesis, or ineffective erythropoiesis, comprising administering to the subject an effective amount of a compound of Formula I or a pharmaceutically acceptable salt thereof. In aspects of these embodiments, the treating comprises inhibiting iron transport mediated by ferroportin in the subject.

In certain embodiments, the subject matter described herein is directed to a method of treating a subject afflicted with a disease related to or caused by reduced hepcidin levels, reduced sensitivity of ferroportin to hepcidin, a hemoglobinopathy, or iron overload.

In certain embodiments, the subject matter described herein is directed to a method of treating a subject afflicted with a disease related to or caused by reduced hepcidin levels or reduced sensitivity of ferroportin to hepcidin. In a certain aspect of this embodiment, the disease is hemochromatosis.

In certain embodiments, the subject matter described herein is directed to a method of treating a subject afflicted with a disease related to or caused by a hemoglobinopathy. In a certain aspects of this embodiment, the disease is thalassemia, hemoglobin E disease, hemoglobin H disease, or sickle cell disease. In certain aspects of this embodiment, the disease is sickle cell disease. In certain aspect of this embodiment, the disease is sickle cell anemia.

In certain embodiments, the diseases being associated with, being related to, being caused by or leading to increased iron levels, increased iron absorption, iron overload (e.g., tissue iron overload) or ineffective erythropoiesis comprise thalassemia, hemoglobinopathy, such as hemoglobin E disease (HbE), hemoglobin H disease (HbH), haemochromatosis, hemolytic anemia, such as sickle cell anemia and congenital dyserythropoietic anemia. Additional diseases being associated with, being related to, being caused by or leading to increased iron levels, increased iron absorption, iron overload (e.g., tissue iron overload) include neurodegenerative diseases, such as for example Alzheimer's disease, Parkinson's disease, Huntington's disease, multiple sclerosis, Wilson's disease, amyotrophic lateral sclerosis (ALS), and Friedreich's Ataxia, wherein the compounds and methods are considered to be effective by limiting the deposition or increase of iron in tissue or cells; conditions associated with the formation of radicals, reactive oxygen species (ROS) and oxidative stress caused by excess iron or iron overload; cardiac, liver and endocrine damage caused by excess iron or iron overload; inflammation triggered by excess iron or iron overload; diseases associated with ineffective erythropoiesis, such as myelodysplastic syndromes (MDS, myelodysplasia), polycythemia vera, and congenital dyserythropoietic anemia; diseases, disorders and/or disease conditions that comprise iron overload caused by mutations in genes involved in sensing the systemic iron stores, such as hepcidin/hepcidin antimicrobial peptide (HAMP), hemochromatosis protein (HFE), hemojuvelin (HJV) and transferrin receptor 2 (TFR2), such as in particular diseases related to HFE and HJV gene mutations; diseases related to ferroportin mutations; chronic hemolysis associated diseases, sickle cell diseases (including sickle cell anemia (HbSS) as well as hemoglobin SC disease (HbSC), hemoglobin S beta-plus-thalassemia (HbS/β+), and hemoglobin S beta-zero-thalassemia (HbS/β0)), red cell membrane disorders, Glucose-6-phosphate dehydrogenase deficiency (G6PD deficiency), erythropoietic *porphyria*, Friedreich's Ataxia, as well as subgroups of iron overload such as transfusional iron overload, iron intoxication, pulmonary hemosiderosis, osteopenia, insulin resistance, African iron overload, Hallervordan Spatz disease, hyperferritinemia, ceruloplasmin deficiency, neonatal hemochromatosis and red blood cell disorders comprising thalassemia, including alpha thalassemia, beta thalassemia and delta thalassemia, thalassemia *intermedia*, sickle cell disease and myelodyplastic syndrome; liver diseases (e.g. hepatitis B virus infection, hepatitis C virus infection, alcoholic liver disease, autoimmune hepatitis), other conditions including ataxia, Friedreich's ataxia, age-related macular degeneration, age-related cataract, age-related retinal diseases and neurodegenerative disease, such as pantothenate kinase-associated neurodegeneration, restless leg syndrome and Huntington's disease. In certain embodiments, the disease is sickle cell anemia. The ferroportin inhibition activity, for instance by inducing internalization of ferroportin, of the compounds of Formula I and pharmaceutically acceptable salts thereof can be determined by the assays described herein as well as those described in WO2018/192973, incorporated herein by reference in its entirety.

The activity of the compounds of Formula I in the treatment of sickle cell anemia (sickle cell disease) can be determined by using a mouse model, such as e.g. described by Yulin Zhao et al. in "MEK1/2 inhibitors reverse acute vascular occlusion in mouse models of sickle cell disease"; The FASEB Journal Vol. 30, No. 3, pp 1171-1186, 2016. Said mouse model can be suitably adapted to determine the activity of the compounds of Formula I in the treatment of sickle cell anemia. In certain embodiments, the disease is caused by a lack of hepcidin or iron metabolism disorders, particularly iron overload states, such as thalassemia, sickle cell disease and hemochromatosis. In certain embodiments, the disease is related to or caused by reduced hepcidin levels, increased iron levels, increased iron absorption, iron overload, increased erythropoiesis, stress erythropoiesis, or ineffective erythropoiesis. In certain embodiments, the disease is selected from the group consisting of thalassemia, hemoglobinopathy, hemoglobin E disease, hemoglobin H disease, haemochromatosis, and hemolytic anemia.

In certain embodiments, the subject matter described herein is directed to a method of treating beta-thalassemia (b-thalassemia) in a subject, comprising administering to the subject an effective amount of a compound of Formula I or a pharmaceutically acceptable salt thereof. The compounds of Formula I as defined herein, act as ferroportin inhibitors and can be used for treating severe forms of b-thalassemia, such as transfusion-dependent b-thalassemia, including in particular b-thalassemia major and hemoglobin E b-thalassemia and the symptoms and pathological conditions associated therewith, such as in particular defective red blood cell production in the bone marrow, ineffective erythropoiesis, low hemoglobin levels/anemia, multiple organ dysfunction, iron overload, liver iron loading and cardiac iron overload, paleness, fatigue, jaundice, and splenomegaly.

In particular, a severe form of b-thalassemia is transfusion-dependent b-thalassemia (TDT), including in particular b-thalassemia major and severe forms of hemoglobin E b-thalassemia. Severe forms of b-thalassemia and hemoglobin E 13-thalassemia, require that patients suffering therefrom achieve regular blood transfusions/Red Blood Cell transfusions (RBC transfusions). Such severe forms of b-thalassemia are thus also summarized as transfUsion-dependent b-thalassemia (TDT). Thus the methods of treating severe forms of b-thalassemia, such as in particular transfusion-dependent b-thalassemia (TDT), include in particular b-thalassemia major and severe forms of hemoglobin E b-thalassemia by administering to a subject in need thereof one or more of the compounds of Formula I as described herein.

The subject may be: suffering from b-thalassemia or haemoglobin E b-thalassemla and requiring regular blood transfusion; suffering from b-thalassemia major and/or severe haemoglobin E b-thalassemia, more particularly to patients suffering from b-thalassemia major.

The methods of treating beta-thalassemia can result in: reduced NTBI levels in a subject; reduced LPI levels in a subject; reduced alpha globin aggregate levels in a subject; reduced ROS levels in RBCs of a subject; a decrease in liver iron concentration in the subject; a decrease in myocardial iron concentration in the subject; an improvement of at least one of the parameters Hct, MCV, MCH, ROW and reticulocyte numbers in the subject; in an erythroid response, which comprises a reduction in transfusion burden in the subject; a reduction of transfusion burden in the subject compared to the transfusion burden prior to treatment using the methods; achieving no longer requiring a transfusion in a transfusion-dependent b-thalassemia subject; reduced serum ferritin levels in the subject; a reduction of the symptoms associated with one or more transfusion-dependent b-thalassemia clinical complications. Nonlimiting examples of transfusion-dependent b-thalassemia symptoms include growth retardation, pallor, jaundice, poor musculature, genu valgum, hepatosplenomegaly, leg ulcers, development of masses from extramedullary hematopoiesis, skeletal changes resulting from expansion of the bone marrow, and clinical complications of chronic red blood cell transfusions, such as, for example hepatitis B virus infection, hepatitis C virus infection and human immunodeficiency virus infection, alloimmunization, and organ damage due to iron overload, such as, for example, liver damage, heart damage and endocrine gland damage. Although the compounds of the formula (I) are not expected to directly affect growth differentiation factor 11 (GDF11), decrease of skeletal deformities can also occur caused by reduced extramedullary erythropoiesis.

The following parameters can be determined to evaluate the efficacy of the compounds of the present invention in the new medical use: serum iron, NTBI levels, LPI (Labile Plasma Iron) levels, erythropoietin, TSAT (transferrin saturation), Hb (hemoglobin), Hct (haematocrit), MCV (Mean Cell Volume), MCH (Mean Cell Hemoglobin), RDW (Red Blood Cell Distribution Width) and reticulocyte numbers, complete blood counts, spleen and liver weight, erythropoiesis in spleen and bone marrow, spleen and liver iron content and alpha-globin aggregates in RBC membranes. The determination can be carried out using conventional methods of the art, in particular by those described below in more detail. The compounds (I) of the present invention are suitable to improve at least one of these parameters.

The methods can be prior to or accompanying blood transfusion to prevent or at least attenuate occurrence of transfusion-caused pathological conditions.

In certain embodiments, the subject matter described herein is directed to a method of preventing and treating kidney injuries in a subject, comprising administering to the subject an effective amount of a compound of Formula I or a pharmaceutically acceptable salt thereof. In certain aspects of these embodiments, the compound of Formula I can be co-administered with another pharmaceutically active compound. In certain aspects of these embodiments, the kidney injuries are those induced by catalytic free iron. In certain aspects of these embodiments, the kidney injuries are selected from renal ischemia-reperfusion injury (IRI), ischemic injury and acute kidney injuries. In a further aspect, kidney injuries are selected from acute kidney injury (AK!), renal ischemia-reperfusion injury (IRI), ischemic injury and AKI caused by ischemic injury, AKI following surgery or surgical intervention, such as in particular following cardiac surgery most often with procedures involving cardiopulmonary bypass, other major chest or abdominal surgery, and kidney injury associated with RBC transfusion.

The term "preventing" and the like includes the protection from ischemic renal injury, avoidance of occurrence of AKI or at least reducing the severity of AKI following ischemic injury, RBC transfusion or a surgery intervention e.g. by administering the compounds prior to or accompanying or shortly after an ischemic event, RBC transfusion or the surgery intervention to prevent or at least attenuate occurrence of kidney injuries induced by catalytic free iron.

Free catalytic iron or labile iron or NTBI is considered as a main cause of kidney injury, such as in particular AKI triggered by ischemia. The administration of the ferroportin inhibitor compounds of formula (I) as described herein can protect against the damaging effects of catalytic free iron. Without being bound to theory, the ferroportin inhibitors described herein can reduce or prevent the formation of catalytic free iron or NTBI by sequestering iron in macrophages of liver and spleen, therewith reducing its levels in plasma and reducing the risk of ROS formation. The compounds of Formula I described herein act as ferroportin inhibitors, and have the potential to sequester iron in macrophages, thereby interrupting the cycle of self-sustaining release of catalytic free iron. The compounds of the Formula I are suitable for the prevention and treatment of the kidney injuries described herein by limiting reactive oxygen species (ROS) to avoid kidney tissue injury. Further to catalytic free iron, NTBI and LPI (Labile Plasma Iron) can cause kidney injuries. NTBI encompasses all forms of serum iron that are not tightly associated with transferrin and is chemically and functionality heterogeneous. LPI represents a component of NTBI that is both redox active and chelatable, capable of permeating into organs and inducing tissue iron overload.

The following parameters can be determined to evaluate the efficacy of the compounds for treating kidney injuries: plasma creatinine, glomerular filtration rate (including estimated glomerular filtration rate eGFR), urine albumin excretion, urine neutrophil gelatinase-associated lipoacin (NGAL), NTBI, LPI, RBC hemolysis, blood urea nitrogen (BUN), plasma hemoglobin (Hb), total plasma iron, plasma hepcidin, renal neutrophil infiltration, serum IL-6, spleen, kidney and/or liver iron content, renal ferroportin, KIM-1 (Kidney Injury Mo!ecule-1) as an acute marker for kidney injury in blood and urine, and H-ferritin. Additionally or alternatively, the efficacy of the compounds of the present invention can be determined via the kidney tubular injury score, such as e.g. the CSA-NGAL score (Cardiac Surgery Associated NGAL Score) for detecting acute tubular damage as described in more detail below, the KDIGO score described in more detail below or the EGTI score comprising Endothelial, Glomerular, Tubular and Interstitial (EGTI) components to evaluate histology (described e.g., by: Khalid et al. "Kidney ischaemia reperfusion injury in the rat the EGTI scoring system as a valid and reliable tool for histological assessment" Journal of Histology & Histopathology, Vol. 3, 2016).

The methods of treating or preventing kidney injury can result in a decrease of serum creatinine (sCr) in the subject. The methods of treating or preventing kidney injury can result in a corrected (decreased) urine albumin excretion in the subject. The methods of treating or preventing kidney injury can result in a decrease of blood urea nitrogen (BUN) in the subject. The methods of treating or preventing kidney injury can result in a decrease of total plasma iron in the subject. The methods of treating or preventing kidney injury can result in a decrease of interleukin-6 (!L-6) levels in the subject. The methods of treating or preventing kidney injury can result in a decrease of KIM-1 levels in the subject. The methods of treating or preventing kidney injury can result in an increase in spleen and/or liver iron concentration in the subject. The methods of treating or preventing kidney injury can result in a decrease in kidney iron concentration in the subject. The methods of treating or preventing kidney injury can result in reduced NTBI levels. The methods of treating or preventing kidney injury can result in reduced LPI levels in the subject. The methods of treating or preventing kidney injury can result in an inhibition of tubular injury, such as tubular necrosis. The methods of treating or preventing kidney injury can result in an inhibition of apoptosis. The methods of treating or preventing kidney injury can result in a reduced IRI-induced renal neutrophil infiltration. The methods of treating or preventing kidney injury can result in reduced ROS levels in kidney tissue of the subject. The methods of treating or preventing kidney injury can result in corrected (increased) kidney H-ferritin levels in the subject. In particular, the methods of treating or preventing kidney injury can reduce the occurrence of AKI, renal ischemia-reperfusion injury and AKI caused by ischemic injury, AKI following surgery or surgical intervention, such as in particular following cardiac surgery most often with procedures involving cardiopulmonary bypass, other major chest or abdominal surgery, and kidney injury associated with RBC transfusion. The methods of treating or preventing kidney injury can comprise a) decrease, accelerated decrease or prevention of increase of serum creatinine; and/or b) increase or prevention of decrease of estimated glomerular filtration rate (eGFR); and/or c) decrease or prevention of increase of renal ferroportin; and/or d) increase or prevention of decrease of H-ferritin levels; and/or e) decrease or prevention of increase of renal neutrophil infiltration; and/or f) decrease or prevention of increase of serum IL-6 levels.

In certain embodiments, the methods of administering and treating described herein further comprise co-administration of one or more additional pharmaceutically active compounds or in combination with a blood transfusion.

In a combination therapy, the pharmaceutically active compounds can be administered at the same time, in the same formulation, or at different times. Such combination therapy comprises co-administration of a compound of Formula I or a pharmaceutically acceptable salt thereof with at least one additional pharmaceutically active compound. Combination therapy in a fixed dose combination therapy comprises co-administration of a compound of Formula I or a pharmaceutically acceptable salt thereof with at least one additional pharmaceutically active compound in a fixed-dose formulation. Combination therapy in a free dose combination therapy comprises co-administration of a compound of Formula I or a pharmaceutically acceptable salt thereof and at least one additional pharmaceutically active compound in free doses of the respective compounds, either by simultaneous administration of the individual compounds or by sequential use of the individual compounds over a period of time.

The additional pharmaceutically active compound includes in particular drugs for reducing iron overload (e.g., Tmprss6-ASO or siRNA) or iron chelators, in particular curcumin, SSP-004184, Deferitrin, deferasirox, deferoxamine and/or deferiprone, or antioxidants such as n-acetyl cysteine, anti-diabetics such as GLP-1 receptor agonists, antibiotics such as penicillin, vancomycin (Van) or tobramycin, antifungal drugs, anti-viral drugs such as interferon-a or ribavirin, drugs for the treatment of malaria, anticancer agents, drugs for the treatment of neurodegenerative diseases such as Alzheimer's disease and Parkinson's disease (e.g., dopamine agonists such as Levodopa), or immunosuppressants (cyclosporine A or cyclosporine A derivatives), iron supplements, vitamin supplements, red cell production stimulators (e.g., erythropoietin, Epo), anti-inflammatory agents, anti-thrombolytics, statins, vasopressors and inotropic compounds. A further object of the present invention relates to the use of the above combinations for the prophylaxis and/or treatment of diseases caused by a lack of hepcidin or iron metabolism disorders, such as particularly iron overload states such as in particular thalassemia, sickle cell disease and hemochromatosis and other disorders as described in the present application.

V. Methods of Preparing Compounds of Formula I and Pharmaceutically Acceptable Salts Thereof Compounds can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g., Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie,* 4, Aufl. ed. Springer-Verlag, Berlin, including supplements (also available via the Beilstein online database). DTT refers to dithiothreitol. DHAA refers to dehydroascorbic acid.

Synthetic chemistry transformations and protecting group methodologies (protection and deprotection) useful in synthesizing compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

The General Procedures and Examples provide exemplary methods for preparing compounds. Those skilled in the art will appreciate that other synthetic routes may be used to synthesize the compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

General Synthetic Schemes

General synthetic approaches to compounds 1a and 1b.

In certain embodiments, compounds 1a and 1b can be synthesized as shown in Scheme 1 and Scheme 2. According to Scheme 1, the core thiophenepyrimidine intermediate 2a was displaced by various substituted amine 3a via method A to give intermediate 4a, which was then reacted with various organometallic reagent 5a to provide final compound 1a. According to Scheme 2, The intermediate 6a was saponified to provide carboxylic intermediate 7a which was subsequently coupled with amine to provide final compound 1b.

Scheme 1 depicts a method for preparing exemplary compounds using Method A and Method B.

Scheme 1

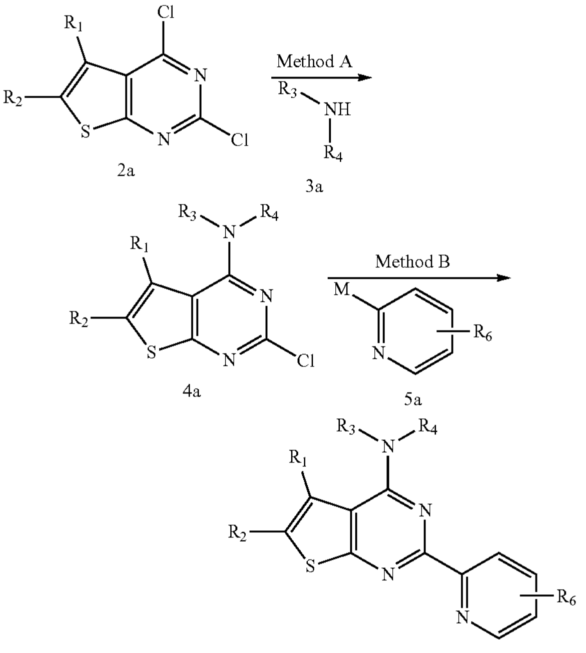

2a 3a 4a 5a 1a

Scheme 2 depicts a method for preparing exemplary compounds using Method A, Method B, Method C, and Method D.

Scheme 2

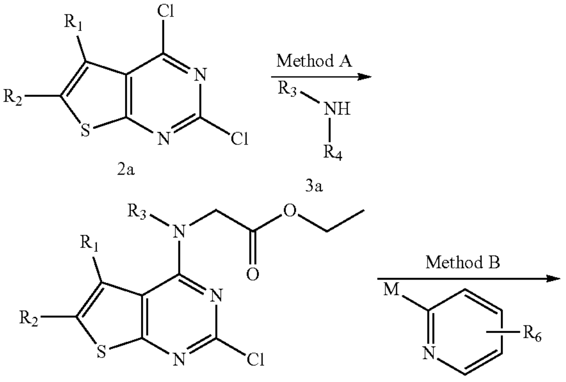

2a 3a 4a 5a

-continued

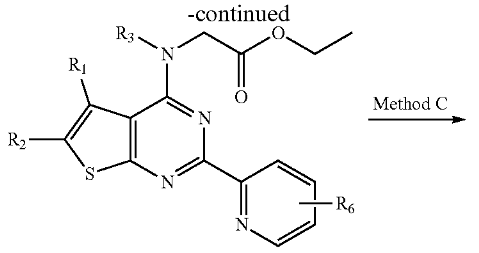

6a

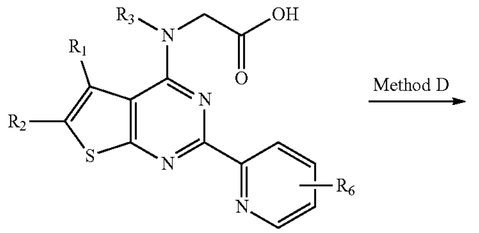

7a

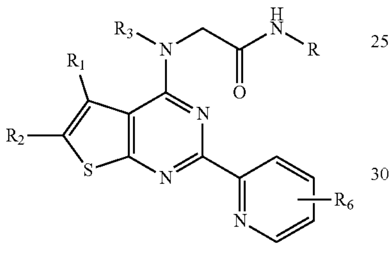

1b

Modifications and variations to Scheme 1 and Scheme 2 can be made based on the availability of starting materials and synthetic compatibility of reagents and starting materials or intermediates. For example, $R_1$ and $R_2$ could be hydrogen, halogen, simple alkyl or join to form a ring; $R_3$ could be hydrogen or alkyl; $R_4$ could be alkyl substituted by aminocarbonyl or alkoxy; or, $R_3$ and $R_4$ could be joined together to form a cyclic amine. For method B, another available heteroaromatic Suzuki or Stille reagent could be used to provide final compound 1a. For Method D, various substituted aniline, fused hetereoaromatic amine, alkylamine, or cycloalkyl amine could be used for the amide coupling reaction to provide final compound 1b.

The conditions and reagents for Methods A-D are provided in the below Examples. The following examples are offered by way of illustration and not by way of limitation.

1. SYNTHETIC EXAMPLES

Example 1.1

Method A: General Synthetic Method for Nucleophilic Coupling of Amine to Intermediate 4a To a suspension of intermediate 2a (1.00 eq.) in EtOH was added amine 3a (1.50 eq.), and the mixture was stirred at room temperature for 15 h. The reaction mixture was subjected to an aqueous workup and extracted with EtOAc. The organic layers were combined and concentrated, and dried under vacuum to provide intermediate 4a.

Example 1.2

Method B: General Synthetic Method for Metal Mediated Cross Coupling to Compound 1a and Compound 6a To a solution of intermediate 4a (1.00 eq.) and organometallic reagent 5a (1.50 eq.) in DMF was added tetrakis (triphenylphosphane) palladium (0.10 eq.). The reaction mixture was heated at 110° C. for 15 h, cooled, and diluted with AcCN and water, which was purified by preparative HPLC to give final compound 1a.

Example 1.3

Method C: General Synthetic Method for Saponification to Compound 7a

To a solution of intermediate 6a (181.79 mg; 0.51 mmol; 1.00 eq.) in THF was added lithiumol hydrate (2.00 eq.) in water. After being stirred for 2 h, the solution was diluted with water and acidified with 1N HCl to pH=3. The aqueous layer was extracted with EtOAc, and the remaining aqueous layer was lyophilized to compound 7a.

Example 1.4

Method D: General Synthetic Method for Amide Coupling Reaction to Compound 1b

To a solution of amine (1.00 eq.) and intermediate 7a (60.00 mg; 0.18 mmol; 1.00 eq.) in DMF (1.5 mL) was added HATU (69.47 mg; 0.18 mmol; 1.00 eq.) and triethylamine (0.05 mL; 0.37 mmol; 2.00 eq.). After being stirred for 30 min, the mixture was subjected to purification by preparative HPLC to give final compound 1b.

Example 1.5

Preparation of Common Reference Compound Int-1

Scheme 3 depicts a method for preparing reference compound Int-1

Scheme 3

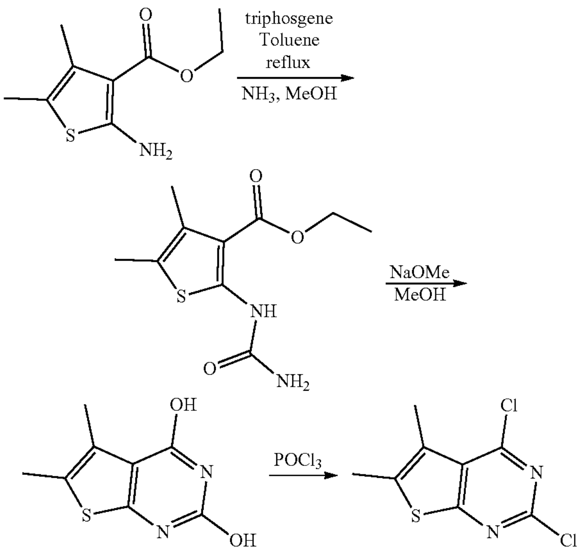

Int-1

Step 1

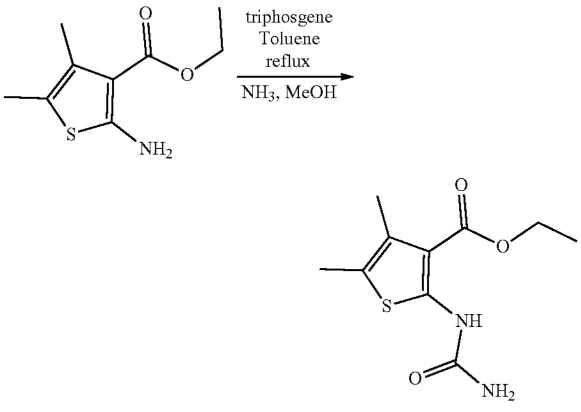

To a solution of ethyl 2-amino-4,5-dimethylthiophene-3-carboxylate (2.00 g; 10.04 mmol; 1.00 eq.) in toluene (100 mL) was added triphosgene (1.04 g; 3.51 mmol; 0.35 eq.). The solution was then heated at reflux for 3 h, cooled, and concentrated to give the crude product. To the crude product was added $NH_3$ in MeOH (7N, 24 mL). After being stirred overnight, the mixture was concentrated and the residue was subjected to column chromatography (hexanes/EtOAc=50:50) to give ethyl 4,5-dimethyl-2-(((trichloromethoxy)carbonyl)amino)thiophene-3-carboxylate (1.20 g, 49%).

Step 2

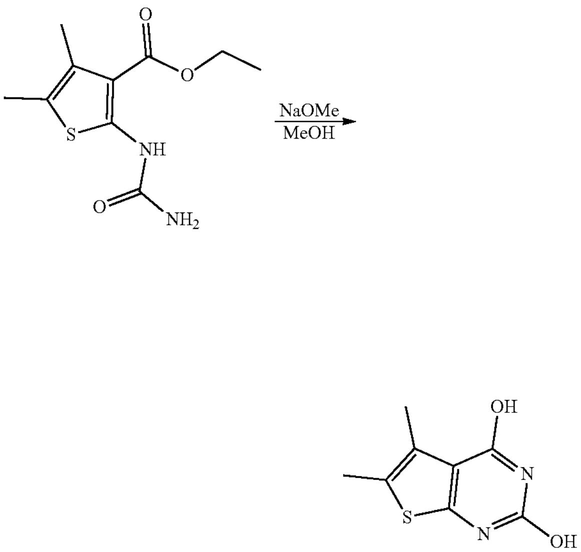

To a suspension of ethyl 4,5-dimethyl-2-(((trichloromethoxy)carbonyl)amino)thiophene-3-carboxylate (1.20 g; 4.95 mmol; 1.00 eq.) in MeOH (24 mL) was added sodium methoxide (2.15 mL; 4.60 mol/L; 9.91 mmol; 2.00 eq.). After stirring for 15 h at room temperature, the mixture was concentrated and the residue was diluted with water followed by 50% $H_2SO_4$ to pH=1. The resulting precipitate was collected by filtration and dried under vacuum to give ethyl 4,5-dimethyl-2-ureidothiophene-3-carboxylate (0.97 g, 100%).

Step 3

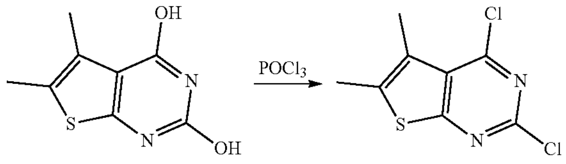

Int-1

To a solution of ethyl 4,5-dimethyl-2-ureidothiophene-3-carboxylate (0.97 g; 4.94 mmol; 1.00 eq.) in $POCl_3$ (20 mL) was added N,N-diethylaniline (0.29 mL; 2.97 mmol; 0.60 eq.). The solution was then heated at 120° C. for 15 h, and then cooled and concentrated and diluted with Sat. $NaHCO_3$ at 0° C. The resulting precipitates were collected by filtration and purified by column chromatography (Hexanes/EtOAc=1:1) to give 2,4-dichloro-5,6-dimethylthieno[2,3-d]pyrimidine (0.62 g, 54%). $^1H$ NMR (400 MHz, Chloroform-d) δ 2.58-2.53 (m, 3H), 2.51 (d, J=1.3 Hz, 3H). LCMS: (ES) $[M+1]^+$ m/z: 231.2, 235.2.

Example 1.6

Synthesis of N-(2-methoxyethyl)-N,5,6-trimethyl-2-(pyridin-2-yl)thieno[2,3-d]pyrimidin-4-amine (Compound 6)

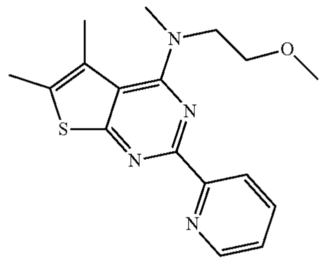

Scheme 4 depicts a method for preparing an exemplary compound.

Scheme 4

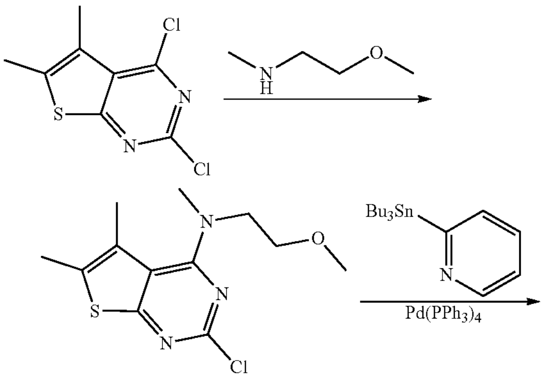

-continued

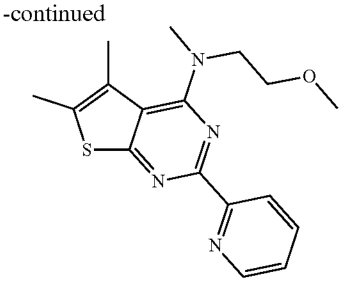

Step 1

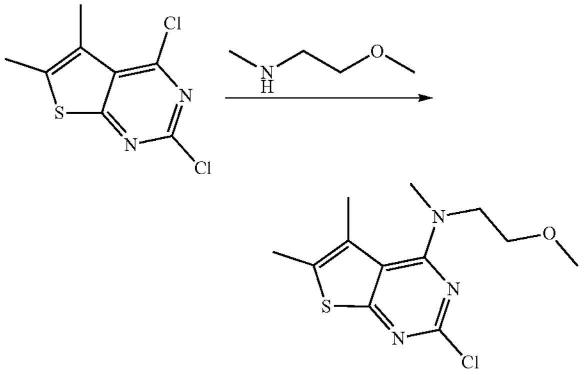

To a suspension of 2,4-dichloro-5,6-dimethylthieno[2,3-d]pyrimidine (75.00 mg; 0.32 mmol; 1.00 eq.) in EtOH (1.5 mL) was added N-(2-methoxyethyl)-N-methylamine (43.02 mg; 0.48 mmol; 1.50 eq.). The mixture was stirred at room temperature for 15 h, followed by the addition of 0.5 eq of N-(2-methoxyethyl)-N-methylamine (43.02 mg; 0.48 mmol; 1.50 eq.). The mixture was then stirred until HPLC indicated the reaction was finished. The mixture was then subjected to work up with EtOAc and Sat. $NaHCO_3$. The organic layers were combined and dried with $MgSO_4$, filtered, and concentrated to give 2-chloro-N-(2-methoxyethyl)-N,5,6-trimethylthieno[2,3-d]pyrimidin-4-amine (79 mg, 86%).

Step 2

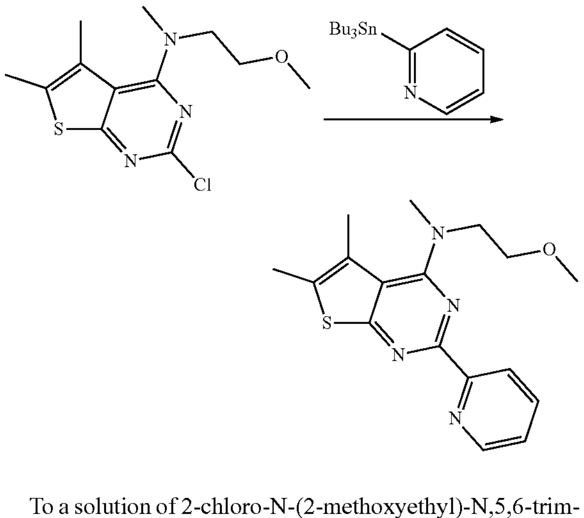

To a solution of 2-chloro-N-(2-methoxyethyl)-N,5,6-trimethylthieno[2,3-d]pyrimidin-4-amine (75.00 mg; 0.26 mmol; 1.00 eq.) and 2-(tributylstannyl)pyridine (144.92 mg; 0.39 mmol; 1.50 eq.) in DMF (1 mL) was added tetrakis (triphenylphosphane) palladium (30.33 mg; 0.03 mmol; 0.10 eq.). The reaction mixture was heated at 110° C. for 15 h. HPLC indicated that the reaction was complete, and the mixture was cooled and subjected to purification by preparative HPLC to give N-(2-methoxyethyl)-N,5,6-trimethyl-2-(pyridin-2-yl)thieno[2,3-d]pyrimidin-4-amine (7.5 mg, 31%). $^1H$ NMR (400 MHz, Chloroform-d) δ 8.55 (s, 1H), 7.90 (s, 1H), 7.41 (s, 1H), 7.26 (d, J=0.9 Hz, 1H), 3.86 (s, 2H), 3.73 (t, J=5.6 Hz, 2H), 3.33 (s, 3H), 3.21-3.16 (m, 3H), 2.46 (d, J=7.5 Hz, 6H). LCMS: (ES) $[M+1]^+$ m/z: 328.6.

Example 1.7

Synthesis of 1-(2-{[5,6-dimethyl-2-(pyridin-2-yl)thieno[2,3-d]pyrimidin-4-yl](methyl)amino}ethyl)pyrrolidin-2-one (Compound 5)

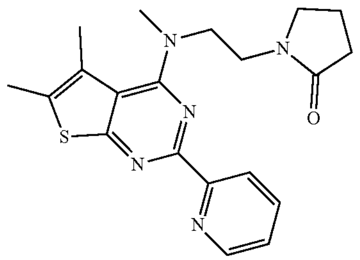 [SMILES: Cc1sc2nc(-c3ccccn3)nc(N(C)CCN3CCCC3=O)c2c1C]

Compound 5 was synthesized similar to 6 by replacing N-(2-methoxyethyl)-N-methylamine with 1-(2-(methylamino)ethyl)pyrrolidin-2-one. $^1H$ NMR (400 MHz, Methanol-d4) δ 8.67 (s, 1H), 8.53 (d, J=8.0 Hz, 1H), 7.96 (t, J=7.8 Hz, 1H), 7.48 (s, 1H), 4.85 (s, 2H), 3.85 (s, 2H), 3.59 (s, 2H), 3.19 (s, 4H), 2.46 (d, J=13.4 Hz, 6H), 2.06 (t, J=7.5 Hz, 2H), 1.72-1.63 (m, 2H). LCMS: [M+1]+m/z: 383.0.

Example 1.8

Synthesis of 2-{[5,6-dimethyl-2-(pyridin-2-yl)thieno[2,3-d]pyrimidin-4-yl](methyl)amino}-N-(4-methoxyphenyl)acetamide (Compound 2)

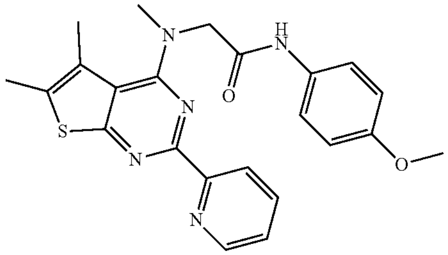

Scheme 5 depicts a method for preparing an exemplary compound.

Scheme 5

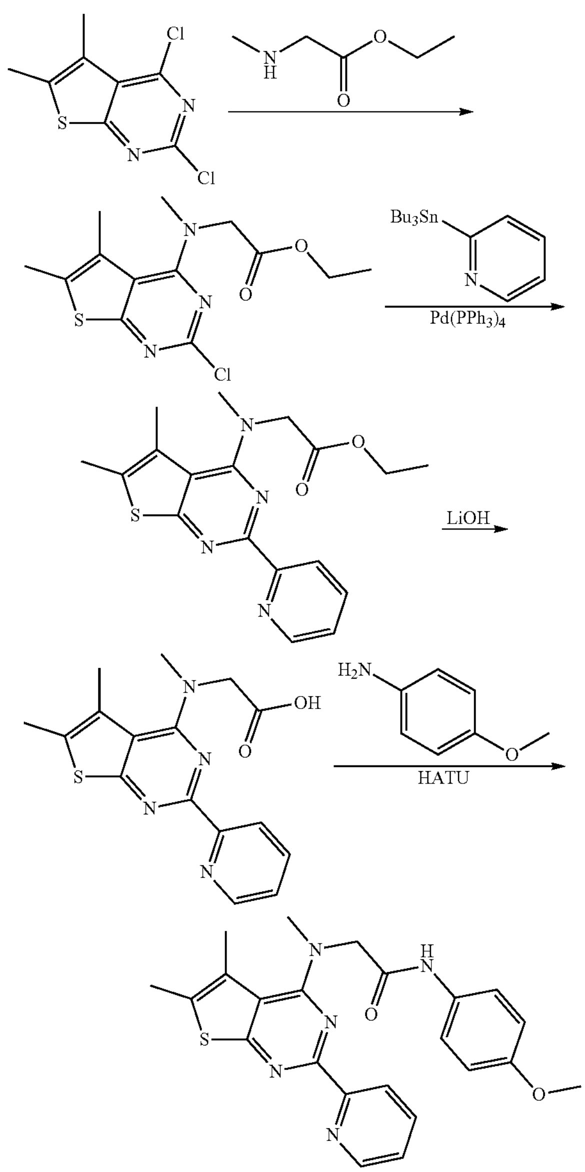

Step 1

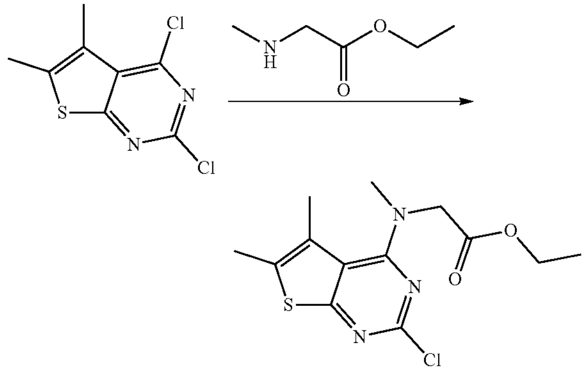

To a suspension of 2,4-dichloro-5,6-dimethylthieno[2,3-d]pyrimidine (150.00 mg; 0.64 mmol; 1.00 eq.) in EtOH (2 mL) was added ethyl methylglycinate HCl salt (170.70 mg; 1.13 mmol; 1.75 eq.), followed by triethylamine (0.31 mL; 2.25 mmol; 3.50 eq.). The mixture was stirred at room temperature for 15 h and concentrated to give a crude residue. The crude residue was diluted with water. The resulting precipitates were collected by filtration and dried under vacuum to give ethyl N-(2-chloro-5,6-dimethylthieno[2,3-d]pyrimidin-4-yl)-N-methylglycinate (181.8 mg, 90%).

Step 2

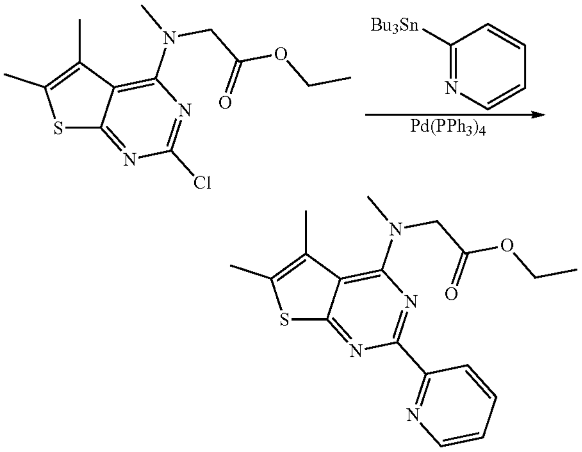

To a solution of ethyl N-(2-chloro-5,6-dimethylthieno[2,3-d]pyrimidin-4-yl)-N-methylglycinate (160.00 mg; 0.51 mmol; 1.00 eq.) and 2-(tributylstannyl)pyridine (319.10 mg; 0.87 mmol; 1.70 eq.) in DMF (1.5 mL) was added tetrakis(triphenylphosphane) palladium (58.92 mg; 0.05 mmol; 0.10 eq.). After being degassed and heated at 105° C. for 4 h, the mixture was cooled and subjected to an aqueous workup, and the crude residue was purified by column chromatography to give ethyl N-(5,6-dimethyl-2-(pyridin-2-yl)thieno[2,3-d]pyrimidin-4-yl)-N-methylglycinate (340 mg, 187%, contains some byproduct).

Step 3

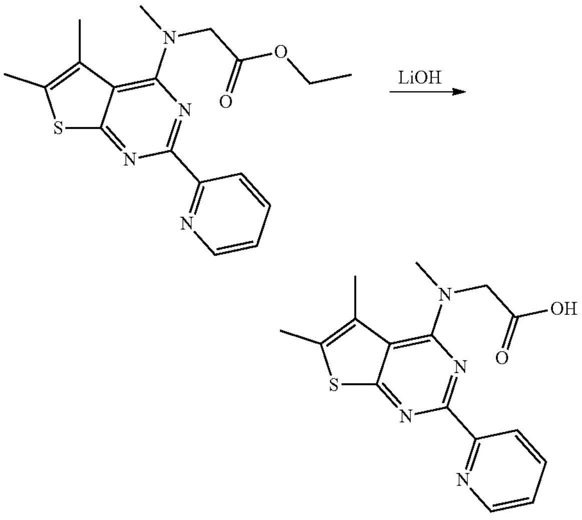

To a solution of ethyl N-(5,6-dimethyl-2-(pyridin-2-yl) thieno[2,3-d]pyrimidin-4-yl)-N-methylglycinate (181.79 mg; 0.51 mmol; 1.00 eq.) in THF (2 mL) was added lithiumol hydrate (42.80 mg; 1.02 mmol; 2.00 eq.) in water (1 mL). After being stirred for 2 h, the solution was diluted with water and extracted with EtOAc. The aqueous layer contained the desired product; hence, the aqueous layer was lyophilized to give N-(2-chloro-5,6-dimethylthieno[2,3-d] pyrimidin-4-yl)-N-methylglycine (120 mg, 77%). LCMS: $[M+1]^+$ m/z: 328.6.

Step 4

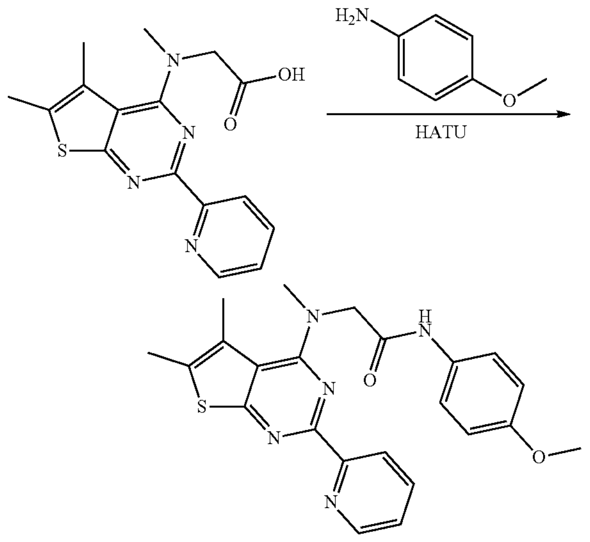

To a solution of 4-methoxyaniline (22.50 mg; 0.18 mmol; 1.00 eq.) and N-(2-chloro-5,6-dimethylthieno[2,3-d]pyrimidin-4-yl)-N-methylglycine (60.00 mg; 0.18 mmol; 1.00 eq.) in DMF (1.5 mL) was added HATU (69.47 mg; 0.18 mmol; 1.00 eq.) and triethylamine (0.05 mL; 0.37 mmol; 2.00 eq.). After being stirred for 30 min, the mixture was subjected to purification by preparative HPLC to give 2-{[5,6-dimethyl-2-(pyridin-2-yl)thieno[2,3-d]pyrimidin-4-yl](methyl) amino}-N-(4-methoxyphenyl)acetamide (22.4, 28%). $^1$H NMR (400 MHz, Methanol-$d_4$) δ 8.67-8.61 (m, 1H), 8.47 (d, J=8.0 Hz, 1H), 7.80 (t, J=7.8 Hz, 1H), 7.50-7.40 (m, 3H), 6.89-6.82 (m, 2H), 4.36 (s, 2H), 3.75 (s, 3H), 3.34 (s, 3H), 2.52 (d, J=10.9 Hz, 6H). LCMS: $[M+1]^+$ m/z: 434.0.

Example 1.9

Synthesis of 2-{[5,6-dimethyl-2-(pyridin-2-yl)thieno [2,3-d]pyrimidin-4-yl](methyl)amino}-N-phenylacetamide (Compound 4)

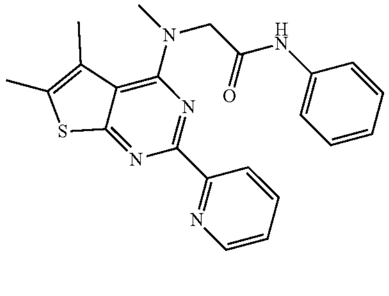 [SMILES: Cc1sc2nc(-c3ccccn3)nc(N(C)CC(=O)Nc3ccccc3)c2c1C]

Compound 4 was synthesized similar to Compound 2 by replacing 4-methoxyaniline with aniline. $^1$H NMR (400 MHz, Methanol-$d_4$) δ 8.62 (d, J=4.9 Hz, 1H), 8.43 (d, J=8.0 Hz, 1H), 7.70 (td, J=7.8, 1.7 Hz, 1H), 7.58-7.51 (m, 2H), 7.45-7.37 (m, 1H), 7.29 (t, J=7.8 Hz, 2H), 7.08 (t, J=7.4 Hz, 1H), 4.38 (s, 2H), 3.35 (s, 3H), 2.52 (d, J=12.6 Hz, 6H). LCMS: $[M+1]^+$ m/z: 404.2.

Example 1.10

Synthesis of 2-{[5,6-dimethyl-2-(pyridin-2-yl)thieno [2,3-d]pyrimidin-4-yl](methyl)amino}-N-(pyridin-3-yl)acetamide (Compound 3)

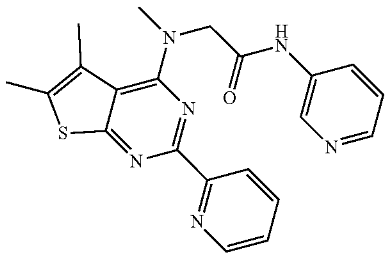 [SMILES: Cc1sc2nc(-c3ccccn3)nc(N(C)CC(=O)Nc3cccnc3)c2c1C]

Compound 3 was synthesized similar to Compound 2 by replacing 4-methoxyaniline with 3-aminopyridine. $^1$H NMR (400 MHz, Methanol-d4) δ 8.72 (d, J=2.5 Hz, 1H), 8.62 (d, J=4.9 Hz, 1H), 8.45-8.38 (m, 1H), 8.25 (dd, J=4.5, 1.8 Hz, 1H), 8.16-8.07 (m, 1H), 7.76 (t, J=7.7 Hz, 1H), 7.40 (ddd, J=19.4, 7.9, 4.9 Hz, 2H), 4.42 (s, 2H), 3.36 (s, 3H), 2.53 (d, J=12.1 Hz, 6H). LCMS: [M+1]+m/z: 405.1 Example 1.11

Synthesis of 2-{[5,6-dimethyl-2-(pyridin-2-yl)thieno [2,3-d]pyrimidin-4-yl](methyl)amino}-N,N-dimethylacetamide (Compound 1)

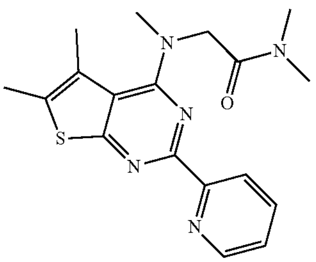

Compound 1 was synthesized similar to Compound 2 by replacing 4-methoxyaniline with Dimethylamine. $^1$H NMR (400 MHz, Methanol-$d_4$) δ 8.66 (d, J=4.4 Hz, 1H), 8.36 (dt, J=8.0, 1.2 Hz, 1H), 7.95 (td, J=7.8, 1.8 Hz, 1H), 7.51-7.43 (m, 1H), 4.85 (s, 1H), 4.48 (s, 2H), 3.27 (d, J=1.8 Hz, 3H), 3.21 (s, OH), 3.20 (s, 3H), 2.98 (s, 3H), 2.49 (s, 6H). LCMS: $[M+1]^+$ m/z: 356.3.

Example 1.12

Synthesis of 2-{[2-(4-methoxypyridin-2-yl)thieno[2,3-d]pyrimidin-4-yl](methyl)amino}-N-(6-methoxy-pyridin-3-yl)acetamide (Compound 7)

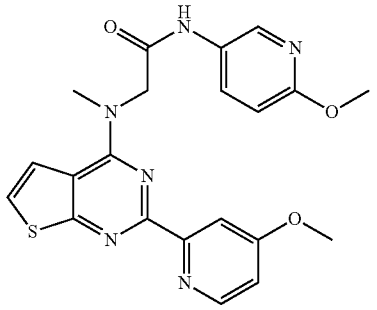 [SMILES: COc1ccnc(-c2nc(N(C)CC(=O)Nc3ccc(OC)nc3)c3ccsc3n2)c1]

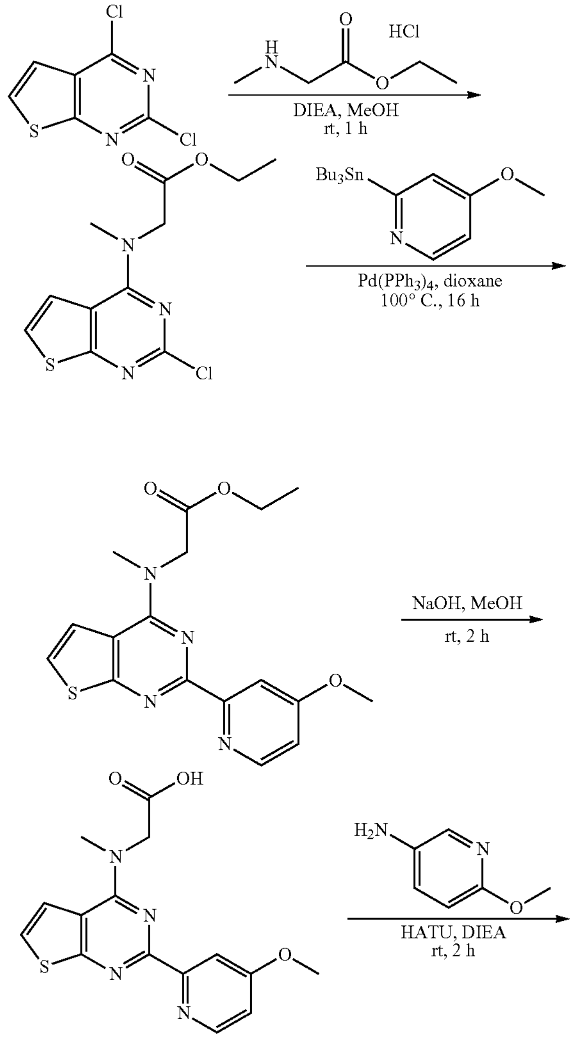

-continued

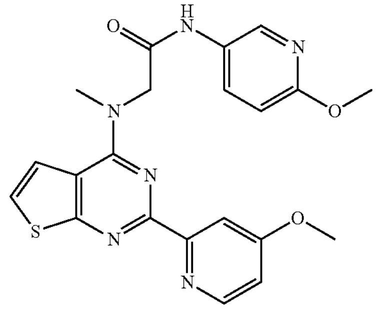

Step 1.

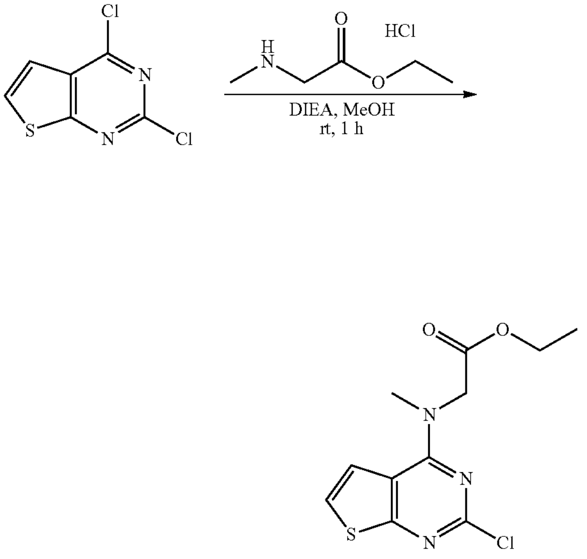

Into a 50-mL vial were placed 2,4-dichlorothieno[2,3-d]pyrimidine (1.00 g, 4.87 mmol, 1.00 equiv), MeOH(10 mL), ethyl 2-(methylamino)acetate hydrochloride (898 mg, 5.85 mmol, 1.20 equiv) and DIEA (1.26 g, 9.75 mmol, 2.00 equiv). The resulting solution was stirred for 1 hour at room temperature. The resulting mixture was concentrated and diluted with 50 mL of $H_2O$. The resulting solution was extracted with 3×50 mL of dichloromethane and dried over anhydrous sodium sulfate. After filtration, the filtrate was concentrated. This resulted in 950 mg (68.17%) of ethyl N-(2-chlorothieno[2,3-d]pyrimidin-4-yl)-N-methylglycinate as a light yellow solid. LCMS (ES) $[M+1]^+$ m/z 286.

Step 2

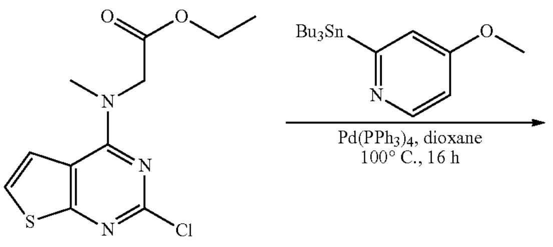

-continued

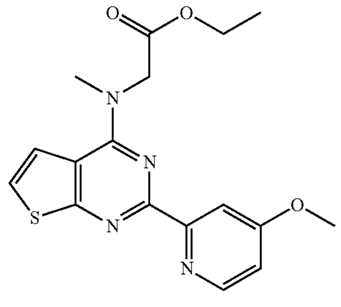

Into a 40-mL vial purged and maintained with an inert atmosphere of nitrogen were placed a mixture of ethyl N-(2-chlorothieno[2,3-d]pyrimidin-4-yl)-N-methylglycinate (900 mg, 3.15 mmol, 1.00 equiv), dioxane (20.0 mL), 4-methoxy-2-(tributylstannyl)pyridine (1.38 g, 3.46 mmol, 1.10 equiv) and $Pd(PPh_3)_4$(363 mg, 0.315 mmol, 0.10 equiv). The resulting solution was stirred for 16 hours at 100° C. The resulting mixture was concentrated and the residue was applied onto a silica gel column with dichloromethane/methanol (10/1). This resulted in 720 mg (63.78%) of ethyl N-(2-(4-methoxypyridin-2-yl)thieno[2,3-d]pyrimidin-4-yl)-N-methylglycinate as brown oil. LCMS (ES) $[M+1]^+$ m/z 359.

Step 3

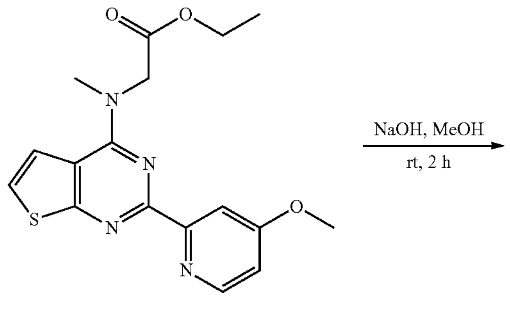

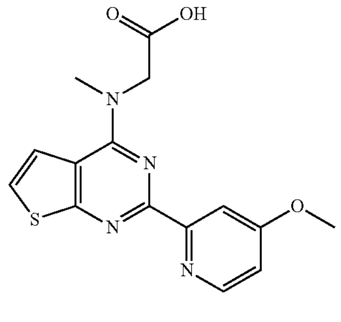

Into a 20-mL vial were placed a mixture of ethyl N-(2-(4-methoxypyridin-2-yl)thieno[2,3-d]pyrimidin-4-yl)-N-methylglycinate (300 mg, 0.837 mmol, 1.00 equiv), MeOH/$H_2O$ (10/2 mL), and NaOH (66.9 mg, 1.67 mmol, 2.00 equiv). The resulting solution was stirred for 2 hours at room temperature. The resulting mixture was concentrated and diluted with $H_2O$. The pH value of the solution was adjusted to 6 with HCl (2 mol/L). The solids were collected by filtration and dried. This resulted in 210 mg (75.95%) of N-(2-(4-methoxypyridin-2-yl)thieno[2,3-d]pyrimidin-4-yl)-N-methylglycine as a light yellow solid. LCMS (ES) $[M+1]^+$ m/z 331.

Step 4

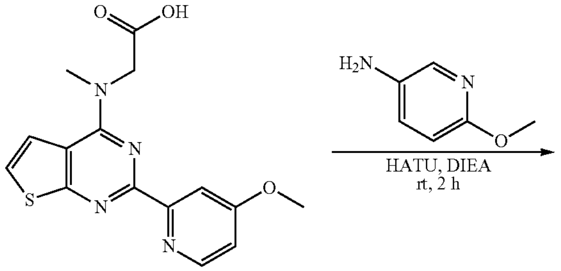

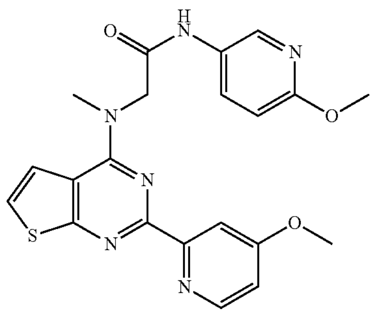

Into a 8-mL vial were placed a mixture of N-(2-(4-methoxypyridin-2-yl)thieno[2,3-d]pyrimidin-4-yl)-N-methylglycine (200 mg, 0.605 mmol, 1.00 equiv), DMF (2.00 mL), 5-amino-2-methoxypyridine (75.1 mg, 0.605 mmol, 1.00 equiv), HATU (276 mg, 0.726 mmol, 1.20 equiv), and DIEA (156 mg, 1.21 mmol, 2.00 equiv). The resulting solution was stirred for 1 hour at room temperature. The crude product was purified by Prep-HPLC with the following conditions: SunFire Prep C18 OBD Column, 19×150 mm, Sum; mobile phase, phase A: $H_2O$ (0.1% formic acid); phase B: $CH_3CN$ (5% $CH_3CN$ up to 35% $CH_3CN$ in 15 min). This resulted in 127.7 mg (48.33%) of 2-{[2-(4-methoxypyridin-2-yl)thieno[2,3-d]pyrimidin-4-yl](methyl)amino}-N-(6-methoxypyridin-3-yl)acetamide as a light yellow solid. LCMS (ES) $[M+1]^+$ m/z 437. $^1H$ NMR (300 MHz, DMSO-$d_6$, ppm): δ 10.30 (s, 1H), 8.52 (d, J=5.7 Hz, 1H), 8.34 (d, J=2.7 Hz, 1H), 7.93 (d, J=2.6 Hz, 1H), 7.87 (dd, J=8.9, 2.7 Hz, 1H), 7.79 (d, J=6.2 Hz, 1H), 7.71 (d, J=6.2 Hz, 1H), 7.11 (dd, J=5.7, 2.6 Hz, 1H), 6.78 (d, J=8.9 Hz, 1H), 4.64 (s, 2H), 3.84 (s, 3H), 3.78 (s, 3H), 3.61 (s, 3H).

Example 1.13
Synthesis of 2-({2-[4-(2-hydroxyethoxy)pyridin-2-yl]-5,6-dimethylthieno[2,3-d]pyrimidin-4-yl}(methyl)amino)-N-(3-methoxyphenyl)acetamide (Compound 8)
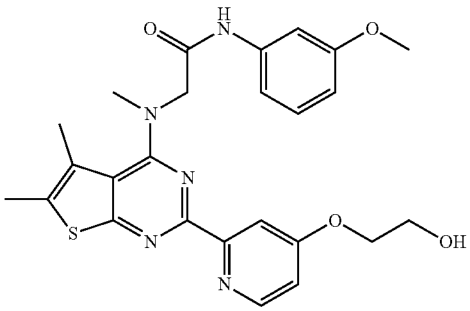 [SMILES: COc1cccc(NC(=O)CN(C)c2nc(-c3cc(OCCO)ccn3)nc3sc(C)c(C)c23)c1]
Scheme 1.13
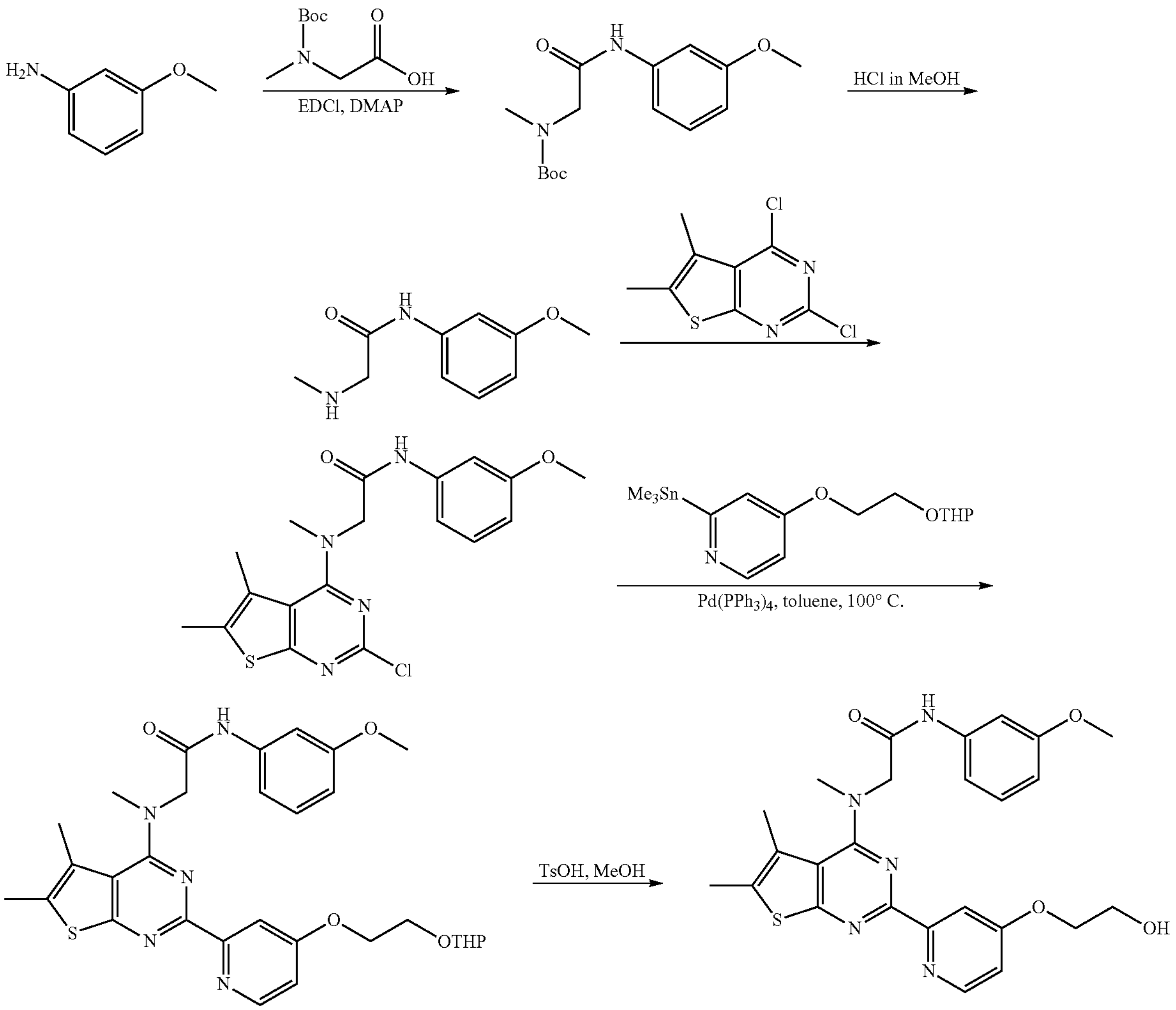

Step 1

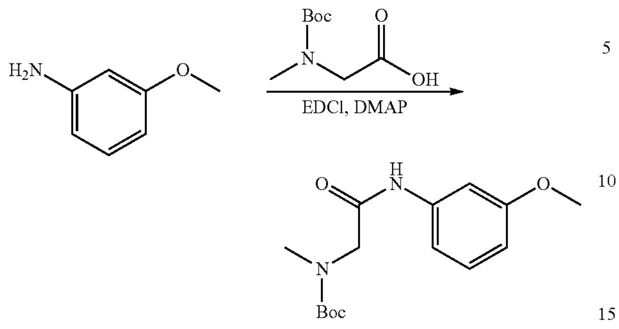

To a stirred solution of [(tert-butoxycarbonyl)(methyl) amino]acetic acid (1.00 g, 5.285 mmol, 1.00 equiv), DIEA (1.37 g, 10.570 mmol, 2 equiv) and m-anisidine (0.72 g, 5.846 mmol, 1.11 equiv) in DMF (10.00 mL, 129.218 mmol, 24.45 equiv) was added HATU (2.41 g, 6.342 mmol, 1.2 equiv) in portions at 0° C. under nitrogen atmosphere. The resulting mixture was stirred for 3 h at room temperature under nitrogen atmosphere and was quenched with water. The resulting mixture was extracted with EtOAc (1×100 mL), the combined organic layers were washed with brine (1×100 mL) and dried over anhydrous $Na_2SO_4$. After filtration, the filtrate was concentrated under reduced pressure. The residue was purified by silica gel column chromatography, eluted with PE/EtOAc (1:1) to afford tert-butyl N-[[(3-methoxyphenyl)carbamoyl]methyl]-N-methylcarbamate (1.2 g, 77.14%) as a yellow solid. LCMS (ES) $[M+1]^+$ m/z: 295

Step 2

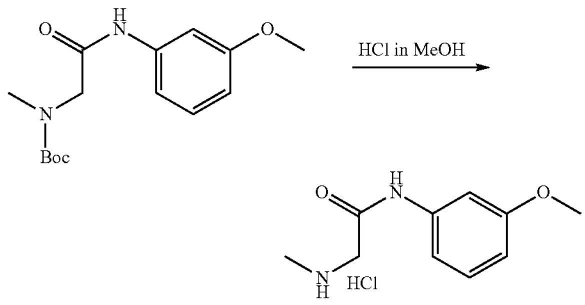

A solution of tert-butyl N-[[(3-methoxyphenyl)carbamoyl]methyl]-N-methylcarbamate (1.50 g, 5.096 mmol, 1.00 equiv) in HCl(g) in MeOH (15.00 mL, 262.762 mmol, 51.56 equiv) was stirred for 2 h at room temperature under air atmosphere. The resulting mixture was concentrated under reduced pressure to afford N-(3-methoxyphenyl)-2-(methylamino)acetamide hydrochloride (1.2 g, 100%) as a white solid. LCMS (ES) $[M-HCl+1]^+$ m/z: 195.

Step 3

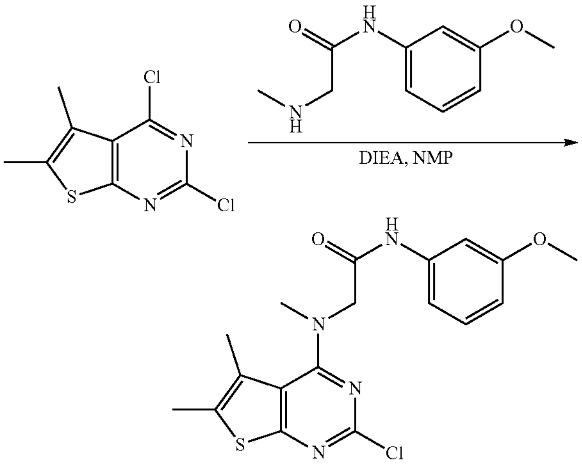

A solution of 2,4-dichloro-5,6-dimethylthieno[2,3-d]pyrimidine (1.00 g, 4.290 mmol, 1.00 equiv), DIEA (1.11 g, 8.580 mmol, 2 equiv) and N-(3-methoxyphenyl)-2-(methylamino)acetamide hydrochloride (1.090 g, 4.72 mmol, 1.20 equiv) in NMP (10 mL) was stirred for 2 h at 60° C. under air atmosphere. The mixture was allowed to cool down to room temperature. The resulting mixture was extracted with EtOAc (1×50 mL). The combined organic layers were washed with water (1×50 mL) and dried over anhydrous $Na_2SO_4$. After filtration, the filtrate was concentrated under reduced pressure. The residue was purified by silica gel column chromatography, eluted with PE/EtOAc (1:1) to afford 2-([2-chloro-5,6-dimethylthieno[2,3-d]pyrimidin-4-yl](methyl)amino)-N-(3-methoxyphenyl)acetamide (1.2 g, 71.56%) as a white solid. LCMS (ES) $[M+1]^+$ m/z: 391.

Step 4

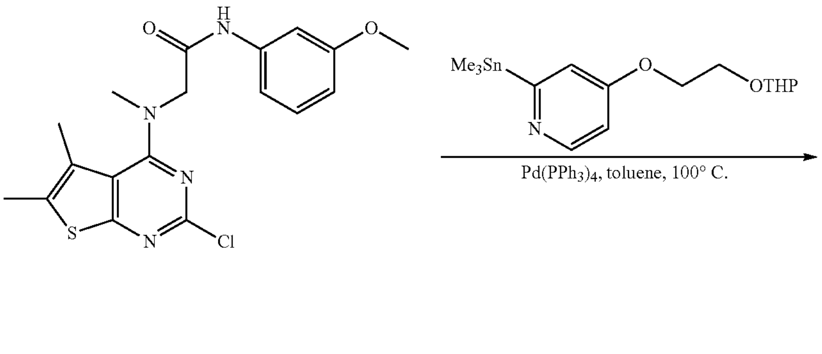

-continued

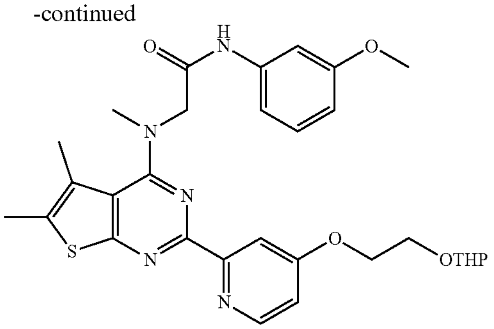

A solution of 2-chloro-4-[2-(oxan-2-yloxy)ethoxy]pyridine (500.00 mg, 1.940 mmol, 1.00 equiv), $Sn_2Me_6$ (699.22 mg, 2.134 mmol, 1.10 equiv) and Pd(dppf)$Cl_2$—$CH_2Cl_2$ (158.05 mg, 0.194 mmol, 0.1 equiv) in toluene (20 mL) was stirred for 4 h at 100° C. under nitrogen atmosphere. The mixture was allowed to cool down to room temperature. To the above mixture was added 2-([2-chloro-5,6-dimethylthieno[2,3-d]pyrimidin-4-yl](methyl)amino)-N-(3-methoxyphenyl)acetamide (530.87 mg, 1.358 mmol, 0.7 equiv) and $Pd(PPh_3)_4$(224.20 mg, 0.194 mmol, 0.1 equiv), and the resulting mixture was stirred for additional 16 h at 100° C. The resulting mixture was concentrated under reduced pressure. The residue was purified by silica gel column chromatography, eluted with PE/THF (1:7) to afford 2-[(5,6-dimethyl-2-[4-[2-(oxan-2-yloxy)ethoxy]pyridin-2-yl]thieno[2,3-d]pyrimidin-4-yl)(methyl)amino]-N-(3-methoxyphenyl)acetamide (500 mg, 44.61%) as a yellow oil. LCMS (ES) $[M+1]^+$ m/z: 578.

Step 5

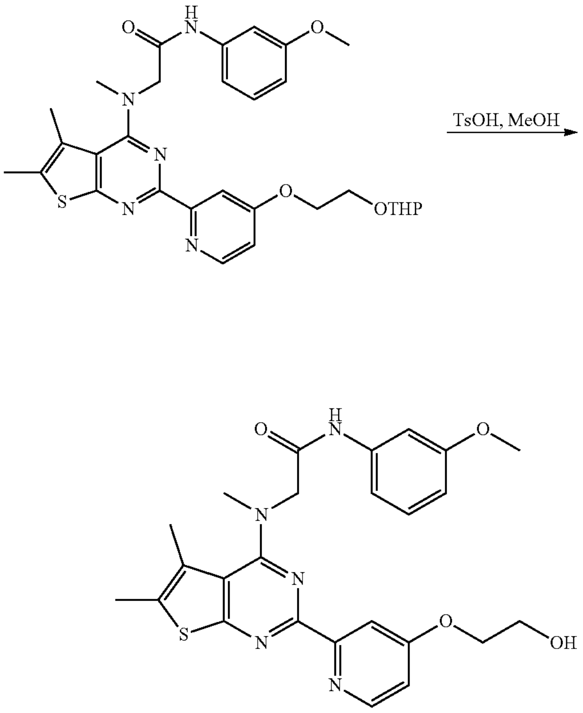

A solution of 2-[(5,6-dimethyl-2-[4-[2-(oxan-2-yloxy)ethoxy]pyridin-2-yl]thieno[2,3-d]pyrimidin-4-yl)(methyl)amino]-N-(3-methoxyphenyl)acetamide (500.00 mg, 0.866 mmol, 1.00 equiv) and p-toluenesulfonic acid (29.81 mg, 0.173 mmol, 0.20 equiv) in MeOH (5.00 mL, 123.495 mmol, 142.69 equiv) was stirred for 2 h at room temperature under air atmosphere. The mixture was basified to pH 7 with saturated $NaHCO_3$(aq.). The crude product was purified by prep-HPLC to afford 2-({2-[4-(2-hydroxyethoxy)pyridin-2-yl]-5,6-dimethylthieno[2,3-d]pyrimidin-4-yl}(methyl)amino)-N-(3-methoxyphenyl)acetamide (86 mg, 20.13%) as a white solid. LCMS (ES) $[M+1]^+$ m/z: 494. $^1$H NMR (300 MHz, DMSO-$d_6$) δ 10.28 (s, 1H), 8.47 (d, J=5.6 Hz, 1H), 7.89 (d, J=2.5 Hz, 1H), 7.28 (t, J=2.2 Hz, 1H), 7.23-7.09 (m, 2H), 7.02 (dd, J=5.7, 2.6 Hz, 1H), 6.77-6.48 (m, 1H), 4.88 (s, 1H), 4.35 (s, 2H), 4.03 (t, J=4.8 Hz, 2H), 3.69 (s, 3H), 3.68-3.23 (m, 2H), 2.48 (s, 3H), 2.47 (s, 3H).

Example 1.14

Synthesis of N-(3-fluorophenyl)-2-({2-[4-(2-hydroxyethoxy)pyridin-2-yl]-5,6-dimethylthieno[2,3-d]pyrimidin-4-yl}(methyl)amino)acetamide (Compound 9)

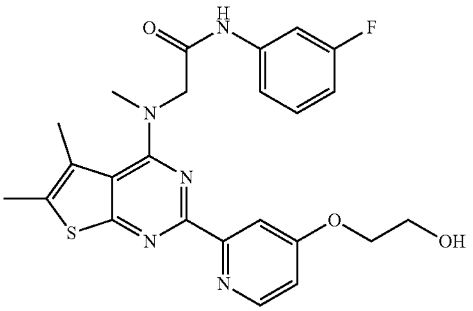 [SMILES: Cc1sc2nc(-c3cc(OCCO)ccn3)nc(N(C)CC(=O)Nc3cccc(F)c3)c2c1C]

Compound 9 was synthesized similar to Compound 8 by replacing m-anisidine with 3-fluoroaniline. LCMS (ES) $[M+1]^+$ m/z: 482. $^1$H NMR (300 MHz, DMSO-$d_6$) δ 10.52 (s, 1H), 8.46 (d, J=5.6 Hz, 1H), 7.87 (d, J=2.5 Hz, 1H), 7.73-7.44 (m, 1H), 7.36-7.28 (m, 2H), 7.02 (dd, J=5.7, 2.6 Hz, 1H), 6.93-6.81 (m, 1H), 4.89 (t, J=5.4 Hz, 1H), 4.36 (s, 2H), 4.03 (t, J=4.8 Hz, 2H), 3.67 (q, J=5.0 Hz, 2H), 3.24 (s, 3H), 2.48 (s, 3H), 2.47 (s, 3H).

Example 1.15

Synthesis of 2-({2-[4-(2-hydroxyethoxy)pyridin-2-yl]-5,6-dimethylthieno[2,3-d]pyrimidin-4-yl}(methyl)amino)-N-(6-methylpyridin-3-yl)acetamide (Compound 10)

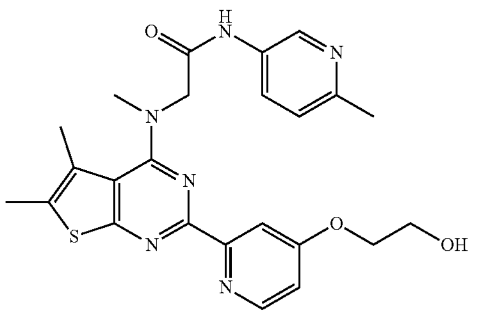 [SMILES: Cc1ccc(NC(=O)CN(C)c2nc(-c3cc(OCCO)ccn3)nc3sc(C)c(C)c23)cn1]

Scheme 1.15

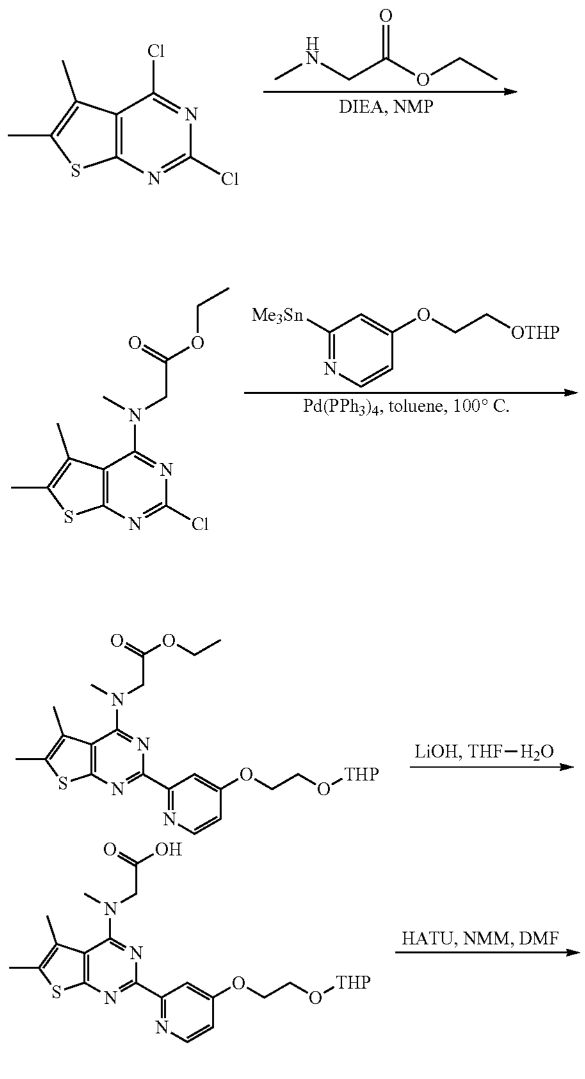

-continued

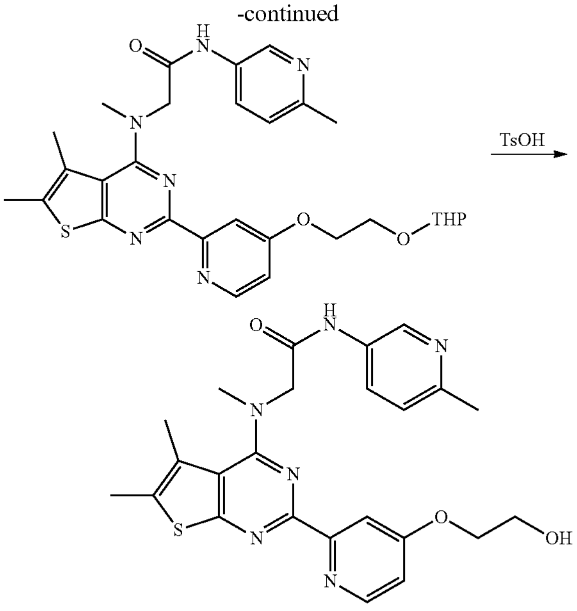

Step 1

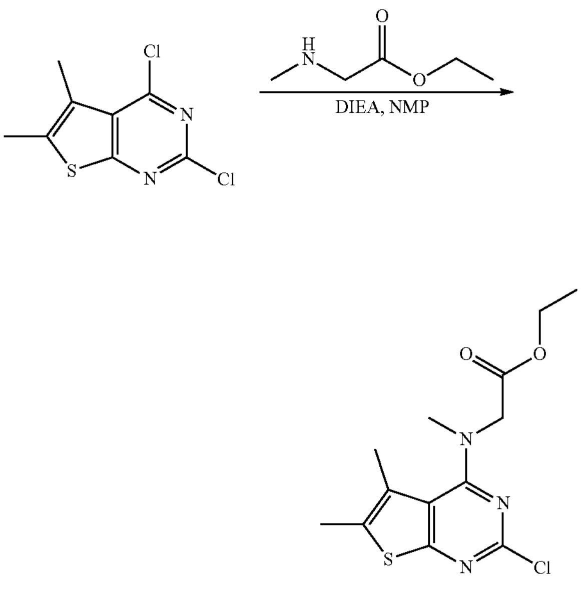

A solution of 2,4-dichloro-5,6-dimethylthieno[2,3-d]pyrimidine (4.00 g, 17.159 mmol, 1.00 equiv), DIEA (6.65 g, 51.478 mmol, 3 equiv) and ethyl methylglycinate (2.41 g, 20.591 mmol, 1.2 equiv) in NMP (40.00 mL, 414.804 mmol, 24.17 equiv) was stirred for 2 h at 60° C. under air atmosphere. The mixture was allowed to cool down to room temperature and quenched with water (100 mL) at room temperature. The resulting mixture was extracted with EtOAc (2×80 mL). The combined organic layers were washed with water (1×100 mL) and dried over anhydrous $Na_2SO_4$. After filtration, the filtrate was concentrated under reduced pressure. The residue was purified by silica gel column chromatography, eluted with PE/EtOAc (1:1) to afford ethyl 2-([2-chloro-5,6-dimethylthieno[2,3-d]pyrimidin-4-yl](methyl)amino)acetate (3.6 g, 66.86%) as a yellow solid. LCMS (ES) $[M+1]^+$ m/z:314

Step 2

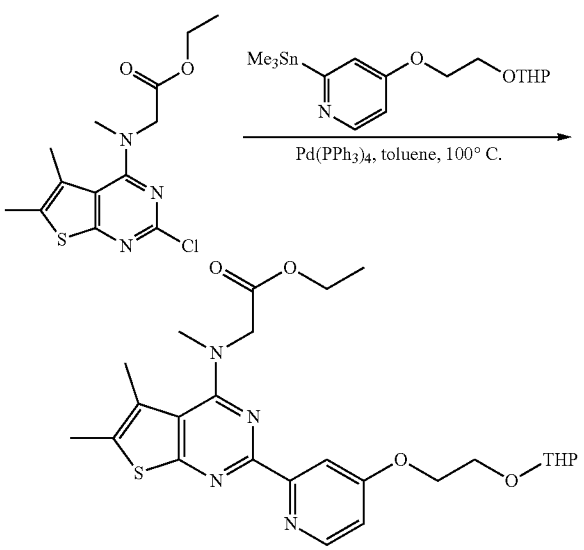

A solution of 2-chloro-4-[2-(oxan-2-yloxy)ethoxy]pyridine (1.00 g, 3.880 mmol, 1.00 equiv), $Sn_2Me_6$ (1.40 g, 4.273 mmol, 1.10 equiv) and Pd(dppf)$Cl_2$ (0.28 g, 0.388 mmol, 0.10 equiv) in toluene (40.00 mL) was stirred for 4 h at 100° C. under nitrogen atmosphere. The mixture was allowed to cool down to room temperature. To the above mixture was added ethyl 2-([2-chloro-5,6-dimethylthieno[2,3-d]pyrimidin-4-yl](methyl)amino)acetate (0.85 g, 2.709 mmol, 0.70 equiv) and Pd($PPh_3$)$_4$(0.45 g, 0.388 mmol, 0.10 equiv) in portions at room temperature. The resulting mixture was stirred for additional 16 h at 100° C. The resulting mixture was concentrated under reduced pressure. The residue was purified by silica gel column chromatography, eluted with PE/THF (4:1) to afford ethyl 2-[(5,6-dimethyl-2-[4-[2-(oxan-2-yloxy)ethoxy]pyridin-2-yl]thieno[2,3-d]pyrimidin-4-yl)(methyl)amino]acetate (1.1 g, 56.63%) as a yellow solid. LCMS (ES) $[M+1]^+$ m/z: 501

Step 3

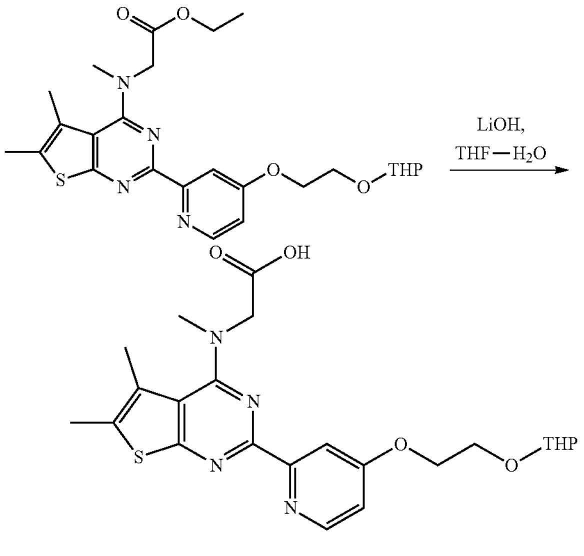

A solution of ethyl 2-[(5,6-dimethyl-2-[4-[2-(oxan-2-yloxy)ethoxy]pyridin-2-yl]thieno[2,3-d]pyrimidin-4-yl)(methyl)amino]acetate (1.00 g, 1.998 mmol, 1.00 equiv) in THE (10 mL) and LiOH (0.10 g, 3.995 mmol, 2 equiv) in $H_2O$ (5.00 mL) was stirred for 2 h at room temperature under air atmosphere. The residue was purified by reverse flash chromatography with the following conditions: column, C18 silica gel; mobile phase, $CH_3CN$ in water, 0% to 50% gradient in 12 min; detector, UV 254 nm to afford [(5,6-dimethyl-2-[4-[2-(oxan-2-yloxy)ethoxy]pyridin-2-yl]thieno[2,3-d]pyrimidin-4-yl)(methyl)amino]acetic acid (410 mg, 43.43%) as a white solid. LCMS (ES) $[M+1]^+$ m/z: 473

Step 4

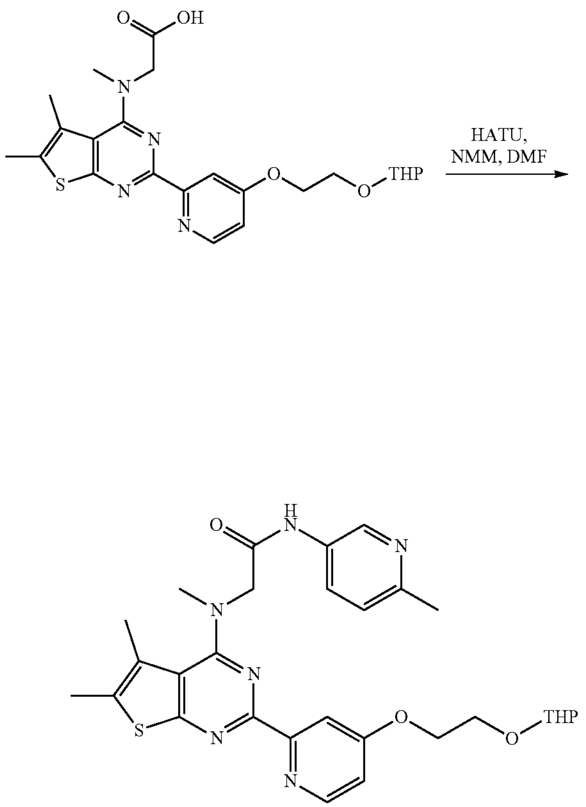

To a stirred solution of [(5,6-dimethyl-2-[4-[2-(oxan-2-yloxy)ethoxy]pyridin-2-yl]thieno[2,3-d]pyrimidin-4-yl)(methyl)amino]acetic acid (180.00 mg, 0.381 mmol, 1.00 equiv), NMM (77.05 mg, 0.762 mmol, 2 equiv) and 6-methylpyridin-3-amine (49.43 mg, 0.457 mmol, 1.2 equiv) in DMF (2.00 mL) was added HATU (173.80 mg, 0.457 mmol, 1.20 equiv) in portions at 0° C. under nitrogen atmosphere. The resulting mixture was stirred for 2 h at room temperature under nitrogen atmosphere. The reaction was quenched with water at room temperature. The resulting mixture was extracted with EtOAc (2×50 mL). The combined organic layers were washed with water (1×100 mL) and dried over anhydrous $Na_2SO_4$. After filtration, the filtrate was concentrated under reduced pressure. The residue was purified by silica gel column chromatography, eluted with PE/THF (5:1) to afford 2-[(5,6-dimethyl-2-[4-[2-(oxan-2-yloxy)ethoxy]pyridin-2-yl]thieno[2,3-d]pyrimidin-4-yl)(methyl)amino]-N-(6-methylpyridin-3-yl)acetamide (150 mg, 69.99%) as a yellow solid. LCMS (ES) $[M+1]^+$ m/z: 563

Step 5

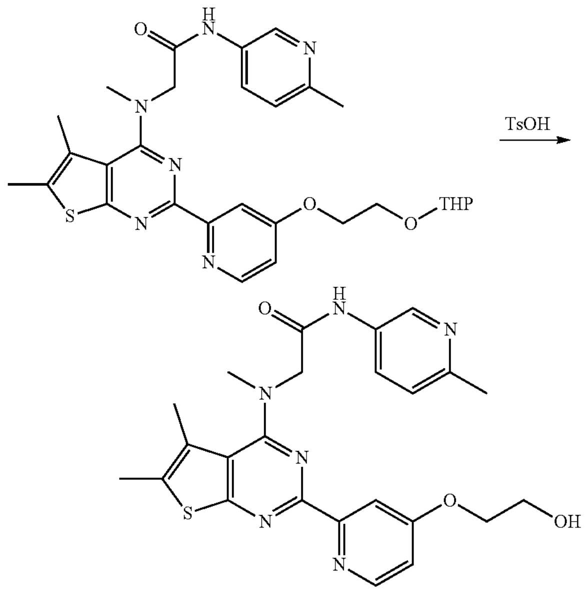

A solution of 2-[(5,6-dimethyl-2-[4-[2-(oxan-2-yloxy)ethoxy]pyridin-2-yl]thieno[2,3-d]pyrimidin-4-yl)(methyl)amino]-N-(6-methylpyridin-3-yl)acetamide (150.00 mg, 0.267 mmol, 1.00 equiv) and p-toluenesulfonic acid (9.18 mg, 0.053 mmol, 0.2 equiv) in MeOH (2.00 mL) was stirred for 2 h at room temperature under air atmosphere. The mixture was basified to pH 7 with saturated $NaHCO_3$(aq.). The crude product was purified by prep-HPLC to afford 2-({2-[4-(2-hydroxyethoxy)pyridin-2-yl]-5,6-dimethylthieno[2,3-d]pyrimidin-4-yl}(methyl)amino)-N-(6-methylpyridin-3-yl)acetamide (74.8 mg, 58.63%) as a white solid. LCMS (ES) $[M+1]^+$ m/z: 479. $^1$H NMR (300 MHz, DMSO-$d_6$) δ 10.47 (s, 1H), 8.60 (d, J=2.5 Hz, 1H), 8.46 (d, J=5.6 Hz, 1H), 8.07-7.81 (m, 2H), 7.18 (d, J=8.4 Hz, 1H), 7.03 (dd, J=5.6, 2.5 Hz, 1H), 5.03 (s, 1H), 4.35 (s, 2H), 4.04 (t, J=4.8 Hz, 2H), 3.69 (s, 2H), 3.29 (s, 3H), 2.48 (s, 3H), 2.47 (s, 3H), 2.40 (s, 3H).

Example 1.16

Synthesis of 2-([2-[4-(2-hydroxyethoxy)pyridin-2-yl]-5,6-dimethylthieno[2,3-d]pyrimidin-4-yl](methyl)amino)-N-(6-methoxypyridin-3-yl)acetamide (Compound 11)

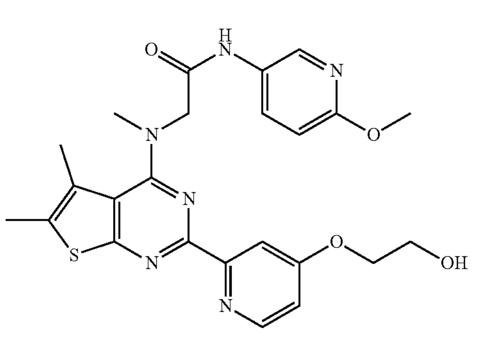 [SMILES: COc1ccc(NC(=O)CN(C)c2nc(-c3cc(OCCO)ccn3)nc3sc(C)c(C)c23)cn1]

Compound 11 was synthesized similar to Compound 10 by replacing 6-methylpyridin-3-amine with 6-methoxypyridin-3-amine. LCMS (ES) $[M+1]^+$ m/z: 495. $^1$H NMR (300 MHz, DMSO-$d_6$) δ 10.38 (s, 1H), 8.46 (d, J=5.6 Hz, 1H), 8.34 (d, J=2.6 Hz, 1H), 7.96-7.81 (m, 2H), 7.04 (dd, J=5.6, 2.5 Hz, 1H), 6.78 (d, J=8.9 Hz, 1H), 4.92 (s, 1H), 4.33 (s, 2H), 4.05 (t, J=4.8 Hz, 2H), 3.80 (s, 3H), 3.71 (t, J=4.8 Hz, 2H), 3.24 (s, 3H), 2.48 (s, 3H), 2.47 (s, 3H).

Example 1.17

Synthesis of 2-{[5,6-dimethyl-2-(1-methyl-1H-imidazol-4-yl)thieno[2,3-d]pyrimidin-4-yl](methyl)amino}-N-(6-methylpyridin-3-yl)acetamide (Compound 12)

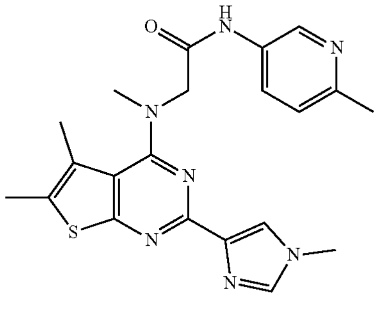

Compound 12 was synthesized similar to Compound 10 by replacing 2-trimethylstannyl-4-[2-(oxan-2-yloxy)ethoxy]pyridine with 1-methyl-4-(tributylstannyl)imidazole. LCMS (ES, m z): $[M+1]^+$:422. $^1$H NMR (300 MHz, DMSO-$d_6$) δ 10.45 (s, 1H), 8.65 (d, J=2.4 Hz, 1H), 8.15 (s, HCOOH), 7.95 (dd, J=8.7, 2.4 Hz, 1H), 7.76 (s, 2H), 7.19 (d, J=8.4 Hz, 1H), 4.26 (s, 2H), 3.62 (s, 3H), 3.20 (s, 3H), 2.43 (s, 3H), 2.42 (s, 3H), 2.41 (s, 3H).

Example 1.18

Synthesis of 2-{[5,6-dimethyl-2-(1-methyl-1H-imidazol-4-yl)thieno[2,3-d]pyrimidin-4-yl](methyl)amino}-N-(6-methoxypyridin-3-yl)acetamide (Compound 13)

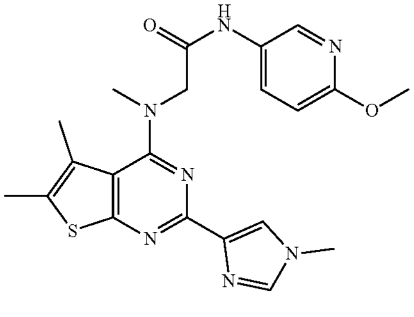

Compound 13 was synthesized similar to Compound 10 by replacing 2-trimethylstannyl-4-[2-(oxan-2-yloxy)ethoxy]pyridine with 1-methyl-4-(tributylstannyl)imidazole and replacing 6-methylpyridin-3-amine with 6-methoxypyridin-3-amine. LCMS (ES, m z): $[M+H]^+$: 438. $^1$H NMR (300 MHz, DMSO-$d_6$) δ 10.36 (s, 1H), 8.39 (d, J=2.4 Hz, 1H), 7.94 (dd, J=8.7, 2.7 Hz, 1H), 7.77 (d, J=1.5 Hz, 1H), 7.74 (d, J=1.2 Hz, 1H), 6.80 (d, J=9.0 Hz, 1H), 4.24 (s, 2H), 3.81 (s, 3H), 3.63 (s, 3H), 3.19 (s, 3H), 2.43 (s, 3H), 2.42 (s, 3H).

Example 1.19

Synthesis of N-tert-butyl-2-{[5,6-dimethyl-2-(1-methyl-1H-imidazol-4-yl)thieno[2,3-d]pyrimidin-4-yl](methyl)amino}acetamide (Compound 14)

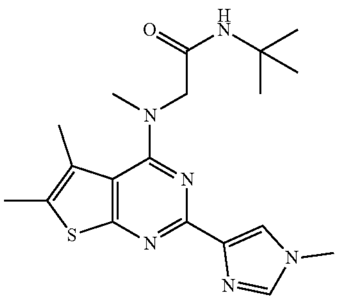

Compound 14 was synthesized similar to Compound 10 by replacing 2-trimethylstannyl-4-[2-(oxan-2-yloxy)ethoxy]pyridine with 1-methyl-4-(tributylstannyl)imidazole and replacing 6-methylpyridin-3-amine with tert-butylamine. LCMS (ES, m z): $[M+H]^+$: 387. $^1$H-NMR (300 MHz, DMSO-$d_6$) δ 7.91 (d, J=1.4 Hz, 1H), 7.87 (s, 1H), 7.69 (s, 1H), 3.99 (s, 2H), 3.75 (s, 3H), 3.07 (s, 3H), 2.42 (s, 3H), 2.38 (s, 3H), 1.25 (s, 9H).

Example 1.20

Synthesis of N-tert-butyl-2-({2-[4-(2-hydroxyethoxy)pyridin-2-yl]-5,6-dimethylthieno[2,3-d]pyrimidin-4-yl}(methyl)amino)acetamide (Compound 15)

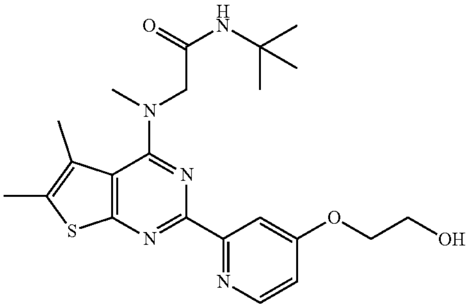 [SMILES: Cc1sc2nc(-c3cc(OCCO)ccn3)nc(N(C)CC(=O)NC(C)(C)C)c2c1C]

Compound 15 was synthesized similar to Compound 10 by replacing 6-methylpyridin-3-amine with tert-butylamine. LCMS (ES) $[M+1]^+$ m/z: 444. $^1$H NMR (300 MHz, DMSO-$d_6$) δ 8.51 (d, J=5.6 Hz, 1H), 7.95 (d, J=2.5 Hz, 1H), 7.74 (s, 1H), 7.08 (dd, J=5.6, 2.6 Hz, 1H), 4.19 (s, 1H), 4.18 (t, J=4.9 Hz, 2H), 4.05 (s, 2H), 3.78 (t, J=4.9 Hz, 2H), 3.14 (s, 3H), 2.48 (s, 3H), 2.47 (s, 3H), 1.23 (s, 9H).

Example 1.21

Synthesis of 2-({2-[4-(2-hydroxyethoxy)pyridin-2-yl]-6-methylthieno[2,3-d]pyrimidin-4-yl}(methyl)amino)-N-(6-methoxypyridin-3-yl)acetamide (Compound 16)

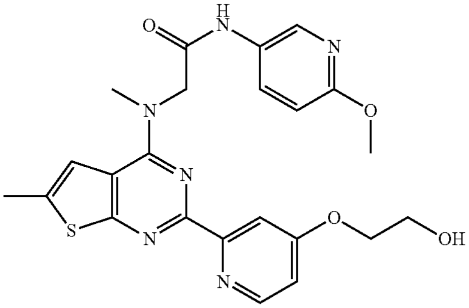 [SMILES: COc1ccc(NC(=O)CN(C)c2nc(-c3cc(OCCO)ccn3)nc3sc(C)cc23)cn1]

Compound 16 was synthesized similar to Compound 8 by replacing 2,4-dichloro-5,6-dimethylthieno[2,3-d]pyrimidine with 2,4-dichloro-6-methylthieno[2,3-d]pyrimidine and by replacing m-anisidine with 6-methoxypyridin-3-amine. LCMS (ES+): $[M+H]^+$=481.1. $^1$H NMR (400 MHz, DMSO-d6) δ 10.39 (s, 1H), 8.47 (d, J=5.6 Hz, 1H), 8.34 (d, J=2.6 Hz, 1H), 7.92-7.85 (m, 2H), 7.43 (d, J=1.4 Hz, 1H), 7.05 (dd, J=5.6, 2.6 Hz, 1H), 6.77 (d, J=8.8 Hz, 1H), 4.93 (t, J=5.4 Hz, 1H), 4.36 (s, 2H), 4.05 (t, J=4.8 Hz, 2H), 3.80 (s, 3H), 3.69 (q, J=5.0 Hz, 2H), 3.31 (s, 3H), 2.59 (d, J=1.2 Hz, 3H).

Example 1.22

Synthesis of 2-({2-[4-(2-hydroxyethoxy)pyridin-2-yl]-5-methylthieno[2,3-d]pyrimidin-4-yl}(methyl)amino)-N-(6-methoxypyridin-3-yl)acetamide (Compound 17)

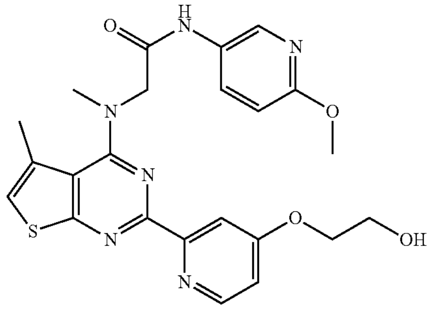 [SMILES: COc1ccc(NC(=O)CN(C)c2nc(-c3cc(OCCO)ccn3)nc3scc(C)c23)cn1]

Compound 15 was synthesized similar to Compound 8 by replacing 2,4-dichloro-5,6-dimethylthieno[2,3-d]pyrimidine with 2,4-dichloro-5-methylthieno[2,3-d]pyrimidine and by replacing m-anisidine with 6-methoxypyridin-3-amine. LCMS (ES+): $[M+H]^+$=481.2. $^1$H NMR (400 MHz, DMSO-d6) δ 10.31 (s, 1H), 8.47 (d, J=5.7 Hz, 1H), 8.35 (s, 1H), 7.93-7.82 (m, 2H), 7.49 (s, 1H), 7.05 (d, J=5.7 Hz, 1H), 6.78 (d, J=8.9 Hz, 1H), 4.93 (s, 1H), 4.59 (s, 2H), 4.06 (t, J=4.8 Hz, 2H), 3.79 (s, 3H), 3.69 (s, 2H), 3.58 (s, 3H), 2.58 (s, 3H).

Example 1.23

Synthesis of N-tert-butyl-2-[(2-{4-[2-(dimethylamino)ethoxy]pyridin-2-yl}-5,6-dimethylthieno[2,3-d]pyrimidin-4-yl)(methyl)amino]acetamide (Compound 18)

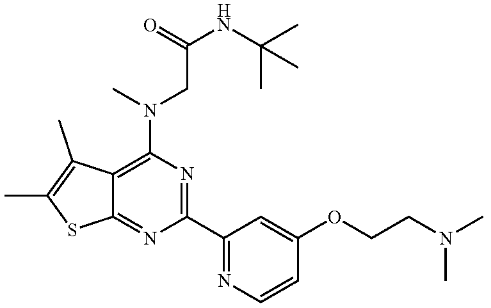

Scheme 1.23

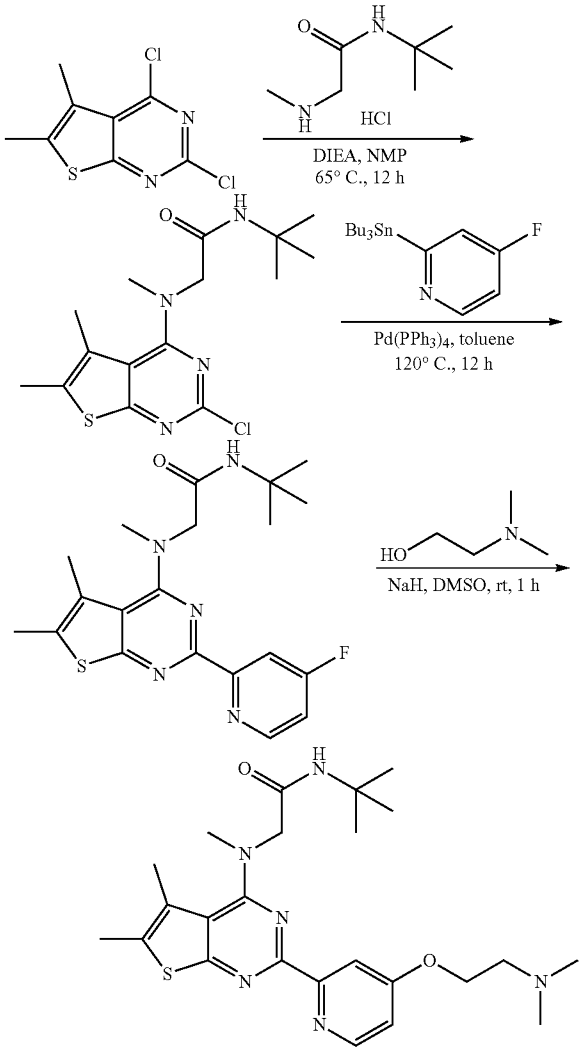

Step 1

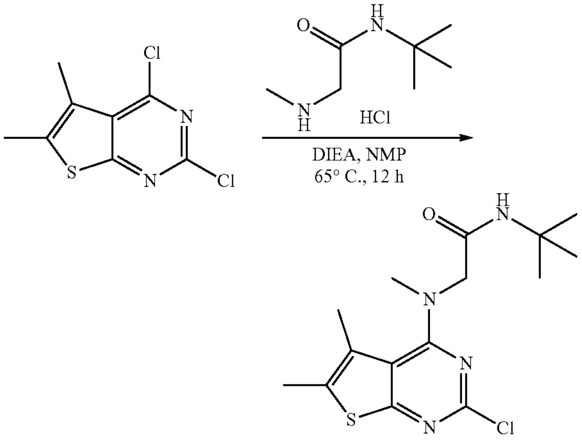

Into a 50 mL round-bottom flask were added 2,4-dichloro-5,6-dimethylthieno[2,3-d]pyrimidine (857 mg, 3.68 mmol, 1.00 equiv), NMP (10.0 mL), DIEA (1.43 g, 11.06 mmol, 3.00 equiv) and N-tert-butyl-2-(methylamino)acetamide hydrochloride (864 mg, 4.78 mmol, 1.30 equiv) at room temperature. The resulting mixture was stirred for 12 h at 65° C. The reaction was quenched with water (20 mL), extracted with EtOAc (30 mL*2). The combined organic phases were washed with brine (20 mL*2), dried over anhydrous sodium sulfate. After filtration, the filtrate was concentrated under reduced pressure. The residue was purified by silica gel column chromatography, eluted with PE/EA (1:1) to afford N-(tert-butyl)-2-((2-chloro-5,6-dimethylthieno[2,3-d]pyrimidin-4-yl)(methyl)amino)acetamide (1.1 g, 88%) as a yellow oil. LCMS (ES) $[M+1]^+$ m/z: 341.

Step 2

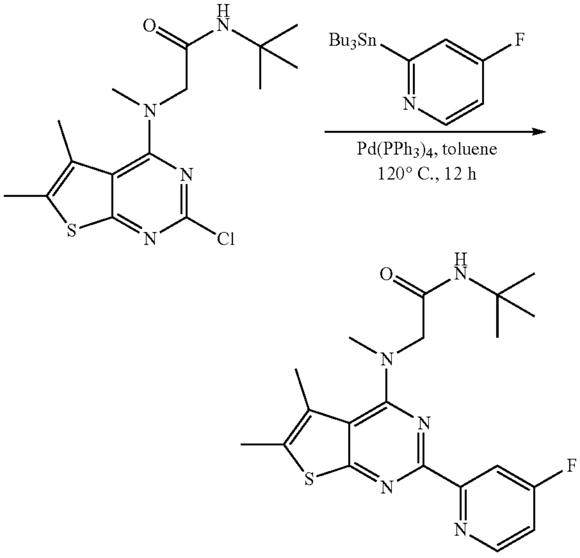

Into a 40 mL vial were added N-(tert-butyl)-2-((2-chloro-5,6-dimethylthieno[2,3-d]pyrimidin-4-yl)(methyl)amino) acetamide (1.1 g, 3.23 mmol, 1.00 equiv), toluene (20.0 mL), $Pd(PPh_3)_4$(0.75 g, 0.65 mmol, 0.20 equiv) and 4-fluoro-2-(tributylstannyl)pyridine (1.87 g, 4.84 mmol, 1.50 equiv) at room temperature. The resulting mixture was stirred for 12 h at 120° C. under nitrogen atmosphere. The reaction mixture was cooled to room temperature and concentrated under reduced pressure. The residue was purified by silica gel column chromatography, eluted with $CH_2Cl_2$/MeOH (10:1) to afford N-(tert-butyl)-2-((2-(4-fluoropyridin-2-yl)-5,6-dimethylthieno[2,3-d]pyrimidin-4-yl)(methyl)amino)acetamide (700 mg, 54%) as a yellow solid. LCMS (ES) $[M+1]^+$ m/z: 402.

Step 3

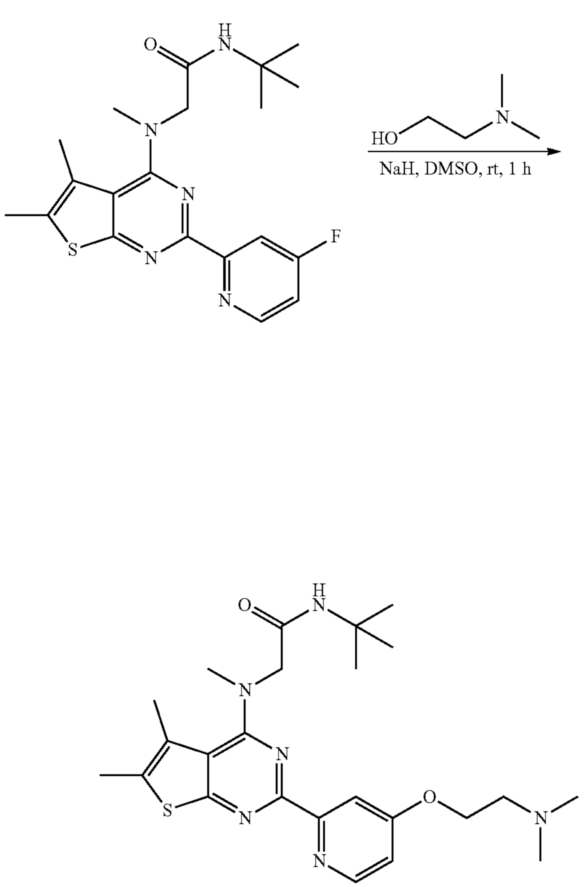

Into a 20 mL vial were added dimethylaminoethanol (89 mg, 1.00 mmol, 2.00 equiv), DMSO (5 mL), NaH (60% in mineral oil) (40 mg, 1.00 mmol, 2.00 equiv). The resulting mixture was stirred for 30 min at room temperature. To the above mixture was added N-(tert-butyl)-2-((2-(4-fluoropyridin-2-yl)-5,6-dimethylthieno[2,3-d]pyrimidin-4-yl)(methyl)amino)acetamide (200 mg, 0.50 mmol, 1.00 equiv) in portions at room temperature. The resulting mixture was stirred for additional 1 h at room temperature. The reaction was quenched with water (0.5 mL) and purified by Prep-HPLC with the following conditions: XBridge Shield RP18 OBD Column, 19*150 mm, 5 μm, mobile phase, water (0.05% $NH_3H_2O$) and $CH_3CN$ (16% up to 33% in 8 min). This resulted in N-(tert-butyl)-2-((2-(4-(2-(dimethylamino)ethoxy)pyridin-2-yl)-5,6-dimethylthieno[2,3-d]pyrimidin-4-yl)(methyl)amino)acetamide(112.9 mg, 48%) as a white solid. LCMS (ES) $[M+1]^+$ m/z: 471. $^1H$ NMR (300 MHz, DMSO-$d_6$) δ 8.51 (d, J=5.6 Hz, 1H), 7.94 (d, J=2.5 Hz, 1H), 7.75 (s, 1H), 7.09 (dd, J=5.6, 2.6 Hz, 1H), 4.22 (t, J=5.7 Hz, 2H), 4.04 (s, 2H), 3.15 (s, 3H), 2.67 (t, J=5.7 Hz, 2H), 2.48-2.44 (m, 3H), 2.43-2.40 (m, 3H), 2.23 (s, 6H), 1.24 (s, 9H).

Example 1.24

Synthesis of N-tert-butyl-2-{[5,6-dimethyl-2-(4-{[(3R)-1-methylpyrrolidin-3-yl]oxy}pyridin-2-yl)thieno[2,3-d]pyrimidin-4-yl](methyl)amino}acetamide (Compound 19)

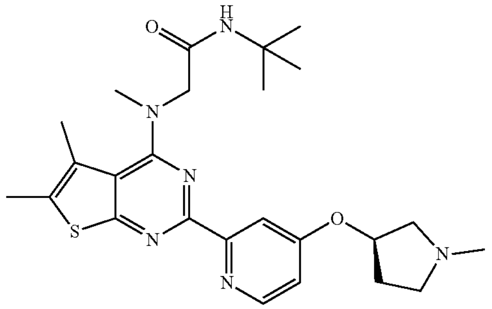

Compound 19 was synthesized similar to Compound 18 by replacing dimethylaminoethanol with (3R)-1-methylpyrrolidin-3-ol. LCMS (ES) $[M+1]^+$ m/z: 483. $^1H$ NMR (300 MHz, DMSO-$d_6$) δ 8.50 (d, J=5.6 Hz, 1H), 7.91 (d, J=2.5 Hz, 1H), 7.77 (s, 1H), 7.02 (dd, J=5.7, 2.6 Hz, 1H), 5.08 (s, 1H), 4.03 (s, 2H), 3.16 (s, 3H), 2.86 (dd, J=10.5, 5.9 Hz, 1H), 2.74-2.60 (m, 2H), 2.48-2.46 (m, 3H), 2.44-2.41 (m, 3H), 2.39 (dd, J=5.6, 2.9 Hz, 2H), 2.28 (s, 3H), 1.90-1.76 (m, 1H), 1.24 (s, 9H).

Example 1.25

Synthesis of N-tert-butyl-2-[(5,6-dimethyl-2-{4-[2-(morpholin-4-yl)ethoxy]pyridin-2-yl}thieno[2,3-d]pyrimidin-4-yl)(methyl)amino]acetamide (Compound 20)

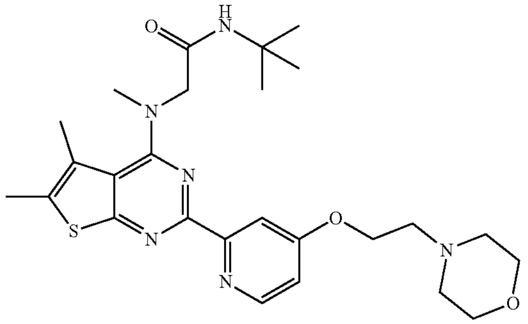 [SMILES: Cc1sc2nc(-c3cc(OCCN4CCOCC4)ccn3)nc(N(C)CC(=O)NC(C)(C)C)c2c1C]

Compound 20 was synthesized similar to Compound 18 by replacing dimethylaminoethanol with 4-morpholineethanol. LCMS (ES) $[M+1]^+$ m/z: 513. $^1H$ NMR (300 MHz, DMSO-$d_6$) δ 8.51 (d, J=5.6 Hz, 1H), 7.94 (d, J=2.5 Hz, 1H), 7.75 (s, 1H), 7.09 (dd, J=5.6, 2.6 Hz, 1H), 4.27 (t, J=5.6 Hz, 2H), 4.04 (s, 2H), 3.64-3.55 (m, 4H), 3.15 (s, 3H), 2.74 (t, J=5.6 Hz, 2H), 2.51-2.39 (m, 10H), 1.24 (s, 9H).

Example 1.26

Synthesis of N-tert-butyl-2-[(5,6-dimethyl-2-{4-[2-(4-methylpiperazin-1-yl)ethoxy]pyridin-2-yl}thieno[2,3-d]pyrimidin-4-yl)(methyl)amino]acetamide (Compound 21)

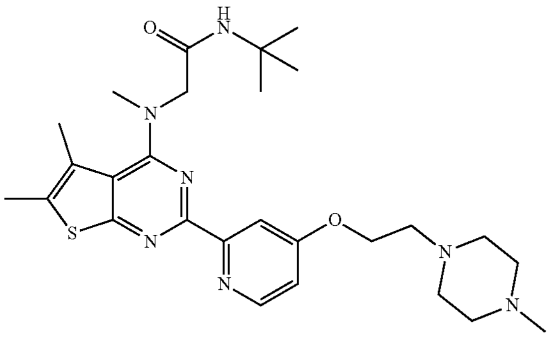

Scheme 1.26

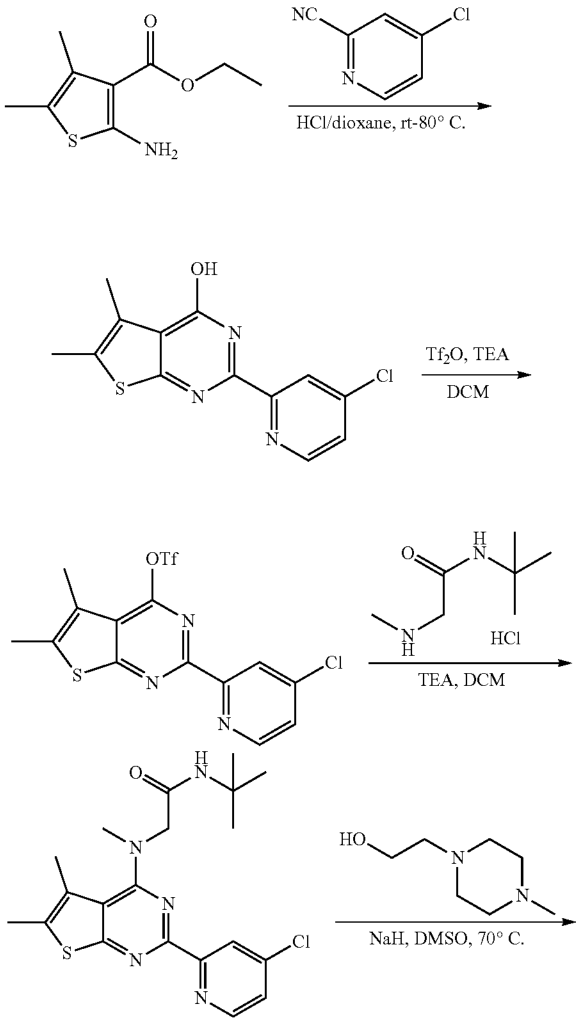

-continued

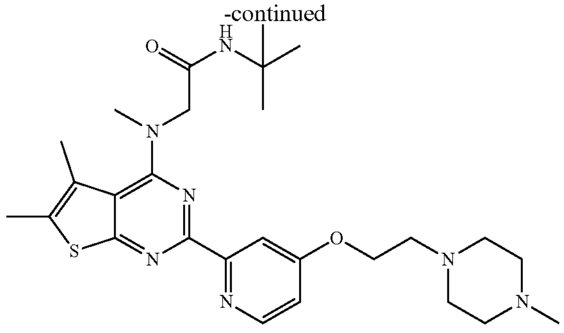

Step 1

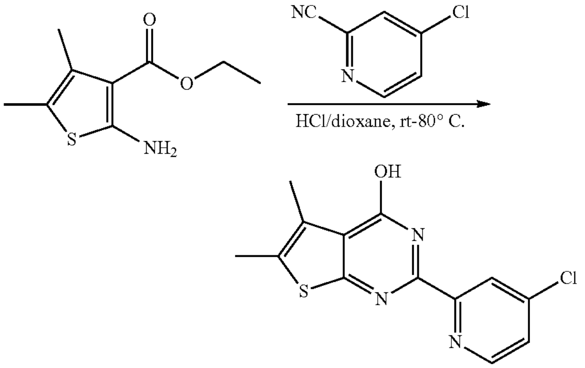

Into a 1000 mL round-bottom flask, was placed ethyl 2-amino-4,5-dimethylthiophene-3-carboxylate (15.00 g, 75.40 mmol, 1.00 equiv) and HCl/dioxane (400.00 mL). This was followed by the addition of 4-chloropicolinonitrile (10.40 g, 75.40 mmol, 1.00 equiv). The resulting solution was stirred for 12 h at 80° C. The reaction was filtered, and the residue was dissolved in water. The pH of the solution was adjusted with $K_2CO_3$ to 8-9, extracted with dichloromethane/methanol (10/1) (3×100 mL) and dried over anhydrous sodium sulfate. After filtration, the filtrate was concentrated under reduced pressure. This gave 2-(4-chloropyridin-2-yl)-5,6-dimethylthieno[2,3-d]pyrimidin-4-ol (5.9 g, 29%) as light yellow solid. LCMS: (ES) $[M+1]^+$ m/z: 292.

Step 2

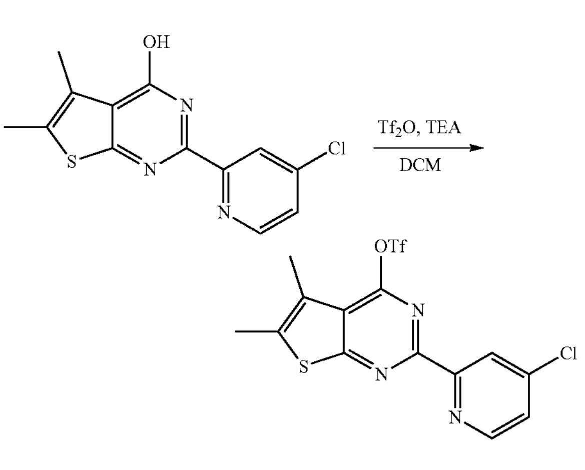

Into a 250 mL round-bottom flask were placed 2-(4-chloropyridin-2-yl)-5,6-dimethylthieno[2,3-d]pyrimidin-4-ol (5.00 g, 17.20 mmol, 1.00 equiv), DCM (60.00 mL) and TEA (7.20 mL, 51.60 mmol, 3.00 equiv). This was followed by the addition of trifluoromethanesulfonic anhydride (4.90 ml, 34.40 mmol, 2.00 equiv) at 0° C. The resulting solution was stirred for 2 h at room temperature. The reaction was extracted with DCM (3×100 mL), dried over anhydrous sodium sulfate and concentrated under reduced pressure. The residue was purified by silica gel column with petroleum ether/tetrahydrofuran (1:1). This gave 2-(4-chloropyridin-2-yl)-5,6-dimethylthieno[2,3-d]pyrimidin-4-yl trifluoromethanesulfonate (5.9 g, 82%) as yellow solid. LCMS: (ES) $[M+1]^+$ m/z: 424.

Step 3

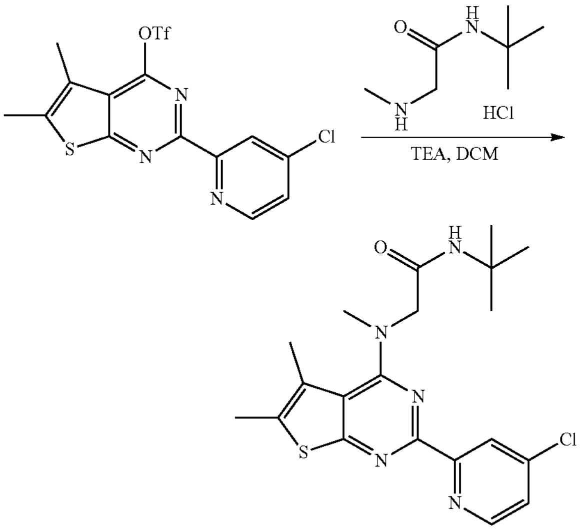

Into a 250 mL round-bottom flask were placed 2-(4-chloropyridin-2-yl)-5,6-dimethylthieno[2,3-d]pyrimidin-4-yl trifluoromethanesulfonate (5.90 g, 14.00 mmol, 1.00 equiv) and DCM (70.00 mL). This was followed by the addition of TEA (5.90 mL, 41.90 mmol, 3.00 equiv) and N-(tert-butyl)-2-(methylamino)acetamide hydrochloride (3.50 g, 19.60 mmol, 1.40 equiv). The resulting solution was stirred for 12 h at room temperature. The reaction was extracted with DCM (100 mL×3) and dried over anhydrous sodium sulfate. After filtration, the filtrate was concentrated under reduced pressure. The residue was purified by silica gel column with petroleum ether/tetrahydrofuran (88:12). This gave N-(tert-butyl)-2-((2-(4-chloropyridin-2-yl)-5,6-dimethylthieno[2,3-d]pyrimidin-4-yl)(methyl)amino)acetamide (3.9 g, 68%) as light yellow solid. LCMS: (ES) $[M+1]^+$ m/z: 418.

Step 4

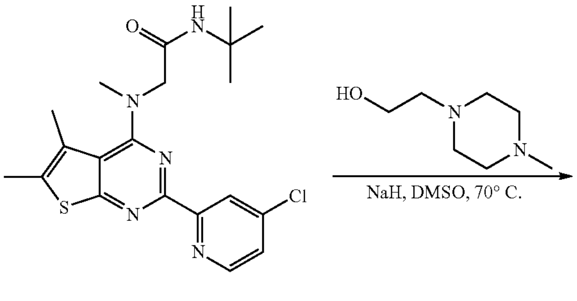

-continued

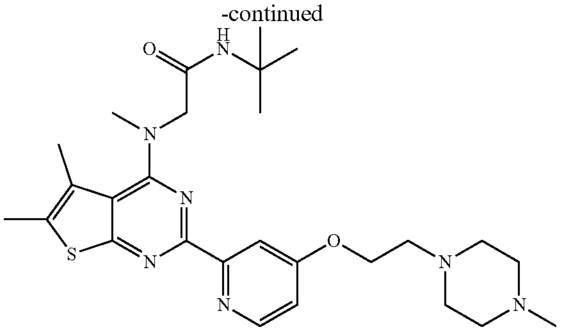

Into a 40 mL vial were placed NaH (58.00 mg, 1.44 mmol, 3.00 equiv) and DMSO (6.00 mL). To a stirred solution was added 2-(4-methylpiperazin-1-yl)ethan-1-ol (1.40 g, 9.60 mmol, 20.00 equiv) dropwise while cooling in an ice bath. The resulting mixture was stirred for 0.5 h at room temperature and added N-(tert-butyl)-2-((2-(4-chloropyridin-2-yl)-5,6-dimethylthieno[2,3-d]pyrimidin-4-yl)(methyl)amino)acetamide (200.00 mg, 0.48 mmol, 1.00 equiv). The resulting solution was stirred for 2 h at 70° C. and cooled down to room temperature. The reaction was quenched by the addition of water/ice (10 mL) at room temperature. The resulting mixture was extracted with EtOAc (3×20 mL). The combined organic layers were dried over anhydrous $Na_2SO_4$. After filtration, the filtrate was concentrated under reduced pressure. The crude product (0.5 g) was purified by prep-HPLC with the following conditions: column, Sunfire Prep C18 OBD Column, 50×250 mm, 5 m; mobile phase A, Water (0.1% formic acid) and B, $CH_3CN$ (5% Phase B up to 35% in 15 min); Detector, 220 nm. This gave N-tert-butyl-2-[(5,6-dimethyl-2-{4-[2-(4-methylpiperazin-1-yl)ethoxy]pyridin-2-yl}thieno[2,3-d]pyrimidin-4-yl)(methyl)amino]acetamide (58.9 mg, 24%) as off white solid. LCMS (ES, m/z): $[M+H]^+$: 526. $^1H$ NMR (300 MHz, Chloroform-d) δ8.65 (d, J=5.6 Hz, 1H), 8.09 (d, J=2.5 Hz, 1H), 7.10 (s, 1H), 6.92 (dd, J=5.7, 2.5 Hz, 1H), 4.33 (t, J=5.6 Hz, 2H), 4.19 (s, 2H), 3.17 (s, 3H), 2.95 (t, J=5.6 Hz, 2H), 2.73-2.61 (m, 8H), 2.51 (s, 3H), 2.50 (s, 3H), 2.38 (s, 3H), 1.25 (s, 9H).

Example 1.27

Synthesis of 2-[(2-{4-[2-(dimethylamino)ethoxy]pyridin-2-yl}-5,6-dimethylthieno[2,3-d]pyrimidin-4-yl)(methyl)amino]-N-[1-(trifluoromethyl)cyclopropyl]acetamide (Compound 22)

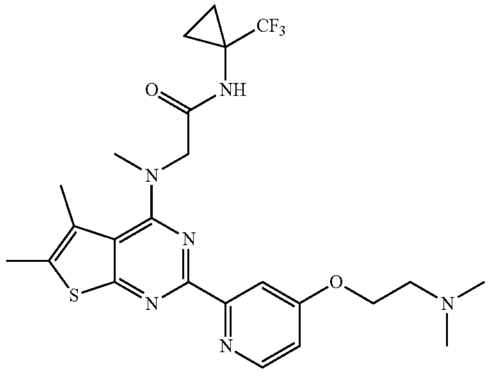

Compound 22 was synthesized similar to Compound 21 by replacing N-(tert-butyl)-2-(methylamino)acetamide hydrochloride with 2-(methylamino)-N-[1-(trifluoromethyl) cyclopropyl]acetamide hydrochloride and replacing 2-(4-methylpiperazin-1-yl)ethan-1-ol with 2-(dimethylamino) ethan-1-ol. LCMS (ES, m z): $[M+H]^+$: 523. $^1H$ NMR (DMSO-$d_6$) 9.21 (s, 1H), 8.51 (d, J=5.7 Hz, 1H), 7.83 (d, J=2.7 Hz, 1H), 7.10 (dd, J=5.7 Hz, 1H), 4.23 (t, J=5.7 Hz, 2H), 4.11 (s, 2H), 3.15 (s, 3H), 2.68 (t, J=5.7 Hz, 2H), 2.47 (s, 3H), 2.42 (s, 3H), 2.24 (s, 6H), 1.20-1.15 (m, 2H), 1.03-1.08 (m, 2H).

Example 1.28

Synthesis of N-tert-butyl-2-{[5,6-dimethyl-2-(4-{2-[(1S,4S)-2-oxa-5-azabicyclo[2.2.1]heptan-5-yl] ethoxy}pyridin-2-yl)thieno[2,3-d]pyrimidin-4-yl] (methyl)amino}acetamide (Compound 23)

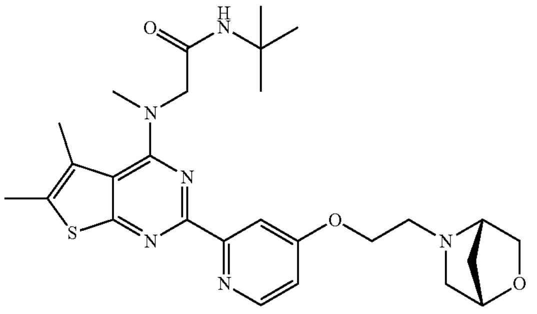 [SMILES: Cc1sc2nc(-c3cc(OCCN4C[C@@H]5C[C@H]4CO5)ccn3)nc(N(C)CC(=O)NC(C)(C)C)c2c1C]

Scheme 1.28

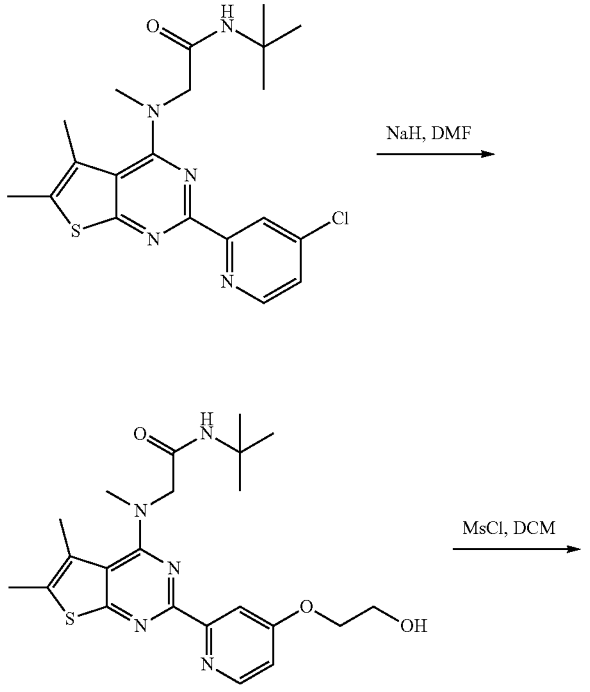

-continued

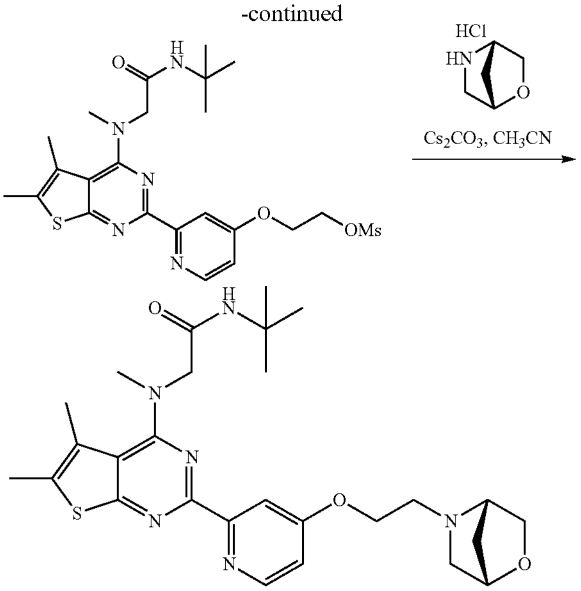

Step 1

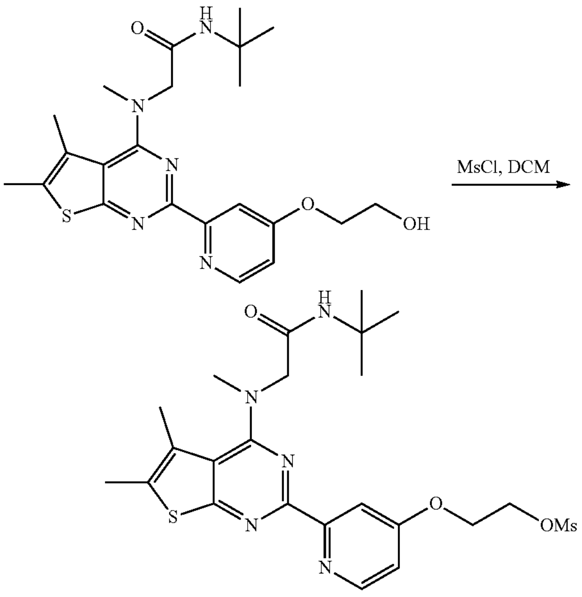

Into a 40 mL vial were added N-tert-butyl-2-({2-[4-(2-hydroxyethoxy)pyridin-2-yl]-5,6-dimethylthieno[2,3-d]pyrimidin-4-yl}(methyl)amino)acetamide (600.00 mg, 1.35 mmol, 1.00 equiv) DCM (20.00 mL) and $Et_3N$ (273.75 mg, 2.71 mmol, 2.00 equiv) at room temperature. 2-Mesitylenesulfonyl chloride (232.42 mg, 2.03 mmol, 1.50 equiv) was added dropwise at 0° C. The resulting mixture was stirred for 2 h at room temperature. The reaction was quenched by the addition of water/ice (10 mL) and extracted with $CH_2Cl_2$ (3×20 mL). The combined organic layers were dried over anhydrous $Na_2SO_4$. After filtration, the filtrate was concentrated under reduced pressure. This gave 2-{[2-(4-{[(tert-butylcarbamoyl)methyl](methyl)amino}-5,6-dimethylthieno[2,3-d]pyrimidin-2-yl)pyridin-4-yl]oxy}ethyl methanesulfonate (600 mg, 85.03%) as yellow solid. LCMS (ES) $[M+1]^+$ m/z: 522.

Step 2

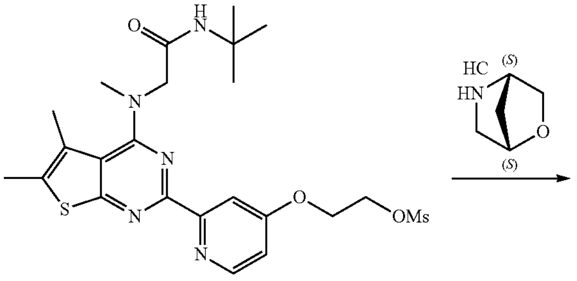

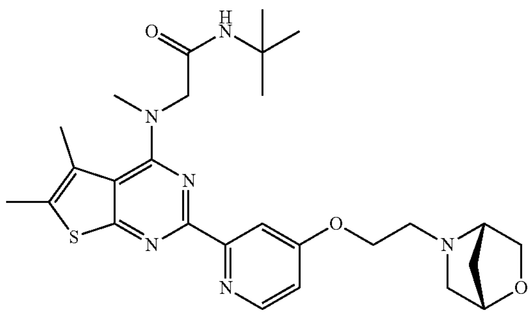

Into a 40 mL vial were added 2-{[2-(4-{[(tert-butylcarbamoyl)methyl](methyl)amino}-5,6-dimethylthieno[2,3-d]pyrimidin-2-yl)pyridin-4-yl]oxy}ethyl methanesulfonate (350.00 mg, 0.67 mmol, 1.00 equiv), (1S,4S)-2-oxa-5-azabicyclo[2.2.1]heptane hydrochloride (109.17 mg, 0.81 mmol, 1.20 equiv), $CH_3CN$ (20.00 mL), $Cs_2CO_3$ (655.82 mg, 2.01 mmol, 3.00 equiv) and KI (11.14 mg, 0.07 mmol, 0.10 equiv) at room temperature. The resulting mixture was stirred overnight at 70° C. The mixture was cooled to room temperature, filtered, the filter cake was washed with MeCN (3×10 mL). The filtrate was concentrated under reduced pressure. The resulting crude product (500 mg) was purified by prep-HPLC with the following conditions: column, XBridge Shield RP18 OBD Column, 19×150 mm, 5p m; mobile phase, Water (10 mmol/L formic acid) and Acetonitrile (15% acetonitrile up to 50% in 9 min); detector, 254 nm. This gave N-tert-butyl-2-{[5,6-dimethyl-2-(4-{2-[(1S,4S)-2-oxa-5-azabicyclo[2.2.1]heptan-5-yl]ethoxy}pyridin-2-yl)thieno[2,3-d]pyrimidin-4-yl](methyl)amino}acetamide (202.8 mg, 57.61%) as light yellow solid. LCMS (ES, m z): $[M+H]^+$: 525. $^1$H-NMR (300 MHz, DMSO-$d_6$, ppm) δ 8.51 (d, J=5.6 Hz, 1H), 7.94 (d, J=2.5 Hz, 1H), 7.75 (s, 1H), 7.08 (dd, J=5.6, 2.6 Hz, 1H), 4.35 (t, J=2.1 Hz, 1H), 4.19 (t, J=5.8 Hz, 2H), 4.04 (s, 2H), 3.86 (d, J=7.5 Hz, 1H), 3.57 (s, 1H), 3.53 (dd, J=7.6, 1.8 Hz, 1H), 3.15 (s, 3H), 3.06-2.94 (m, 1H), 2.98-2.85 (m, 2H), 2.53 (d, J=2.8 Hz, 1H), 2.46 (s, 3H), 2.42 (s, 3H), 1.74 (dd, J=9.5, 2.2 Hz, 1H), 1.59 (dt, J=9.8, 1.6 Hz, 1H), 1.24 (s, 9H).

Example 1.29

Synthesis of N-tert-butyl-2-[(2-{4-[2-(1H-imidazol-1-yl)ethoxy]pyridin-2-yl}-5,6-dimethylthieno[2,3-d]pyrimidin-4-yl)(methyl)amino]acetamide (Compound 24)

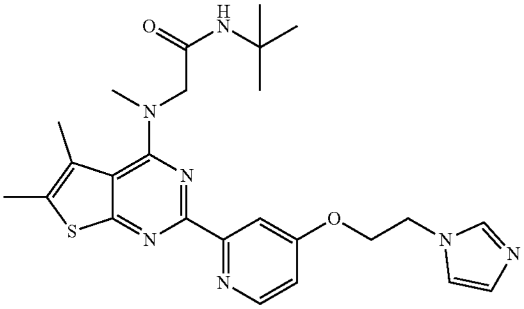 [SMILES: Cc1sc2nc(-c3cc(OCCn4ccnc4)ccn3)nc(N(C)CC(=O)NC(C)(C)C)c2c1C]

Compound 24 was synthesized similar to Compound 21 by replacing 2-(4-methylpiperazin-1-yl)ethan-1-ol with 2-(1H-imidazol-1-yl)ethan-1-ol. LCMS (ES, m z): $[M+H]^+$: 494. $^1$H-NMR (300 MHz, DMSO-$d_6$) δ 9.25 (t, J=1.5 Hz, 1H), 8.79 (d, J=6.6 Hz, 1H), 8.21 (d, J=2.7 Hz, 1H), 7.91 (t, J=1.7 Hz, 1H), 7.76-7.74 (m, 2H), 7.60-7.58 (m, 1H), 4.87 (d, J=4.9 Hz, 2H), 4.76 (d, J=4.6 Hz, 2H), 4.15 (s, 2H), 3.21 (s, 3H), 2.43 (s, 3H), 2.28 (s, 3H), 1.20 (s, 9H).

2. BIOLOGICAL EXAMPLES

Example 2.1

Biological In-Vitro Ferroportin Internalization Assay

The protocol for this assay is generally as described in WO2018/128828, incorporated herein by reference in its entirety. Functional internalization of ferroportin protein was measured using a stably-transfected CHO cell line expressing the human ferroportin tagged to a luciferase reporter. Cells were plated for 24 h in the presence of ferric ammonium citrate (FAC). Ferroportin protein expression was induced with doxycycline for 24 h. The next day, the compounds were added. Test compounds were dissolved in DMSO. Cells were incubated with the test compounds for 6 h, and subsequently luciferase activity was measured using the Nano-Glo Luciferase Assay System and Glomax (Promega, Madison, WI).

The average $pEC_{50}$ was determined for the test compounds. The data is provided in Table 2 below.

TABLE 2

| Compd No. from Table 1 | $pEC_{50}$ |
|---|---|
| 1 | 6.9 |
| 2 | 7.2 |
| 3 | 7.1 |
| 4 | 7 |
| 5 | 6.1 |
| 6 | 6.9 |
| 7 | 6.6 |
| 8 | 7.8 |
| 9 | 7.7 |
| 10 | 7.6 |

TABLE 2-continued

| Compd No. from Table 1 | $pEC_{50}$ |
|---|---|
| 11 | 7.5 |
| 12 | 7.1 |
| 13 | 7.1 |
| 14 | 7 |
| 15 | 7.8 |
| 16 | 7.6 |
| 17 | 7.7 |
| 18 | 7.8 |
| 19 | 7.6 |
| 20 | 8 |
| 21 | 7.8 |
| 22 | 7.5 |
| 23 | 8.2 |
| 24 | 8 |

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound of Formula (I):

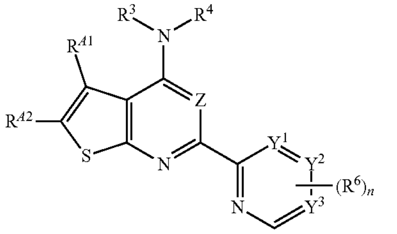

(I)

or a pharmaceutically acceptable salt thereof, wherein, $R^{A1}$ and $R^{A2}$ are each independently selected from the group consisting of hydrogen, $C_1$-$C_3$ alkyl, halogen, and 5- or 6-membered heteroaryl;

Z is N or CH;

$R^6$, in each instance, is selected from the group consisting of halogen, hydroxy, $C_1$-$C_3$ alkoxy, hydroxy-$C_1$-$C_{10}$ alkoxy, —O—($C_1$-$C_6$ alkyl)$_y$-$R^{bb}$, $C_1$-$C_3$ alkyl, and $C_3$-$C_6$ cycloalkyl;

$R^{bb}$ is 4- to 7-membered monocyclic or bridged heterocyclyl, 5- or 6-membered monocyclic heteroaryl or —$NR^GR^H$; wherein, said heterocyclyl and heteroaryl is optionally substituted with one or two substituents, each independently selected from the group consisting of hydroxy, halogen, halo-$C_1$-$C_3$ alkyl, $C_1$-$C_3$ alkoxy, and $C_1$-$C_3$ alkyl, and $R^G$ and $R^H$ are each independently hydrogen or $C_1$-$C_3$ alkyl;

y is 0 or 1;

n is 0, 1, 2, or 3;

$Y^1$ is absent or present, $Y^1$, if present, and $Y^2$, and $Y^3$ are each independently selected from the group consisting of N, CH, and C (when $R^6$ is attached thereto);

$R^3$ is selected from the group consisting of hydrogen, $C_1$-$C_3$ alkyl, and hydroxy-$C_1$-$C_3$ alkyl;

$R^4$ is selected from the group consisting of

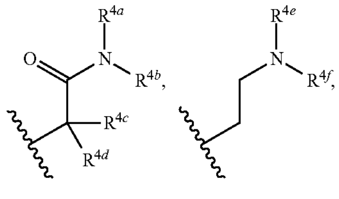

, and

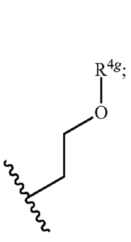

wherein, $R^{4a}$ is hydrogen or $C_1$-$C_6$ alkyl;

$R^{4b}$ is selected from the group consisting of hydrogen, $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl; or $R^{4a}$ and $R^{4b}$ taken together with the atom to which each is attached form a 5- to 7-membered heterocyclyl;

$R^{4c}$ is selected from the group consisting of hydrogen, $C_1$-$C_3$ alkyl, $C_3$-$C_6$ cycloalkyl, and hydroxy-$C_1$-$C_3$ alkyl;

$R^{4d}$ is hydrogen or $C_1$-$C_3$ alkyl; or $R^{4c}$ and $R^{4d}$ taken together with the atom to which each is attached form a $C_3$-$C_6$ cycloalkyl or 5- to 7-membered heterocyclyl;

$R^{4e}$ is selected from the group consisting of hydrogen, $C_1$-$C_3$ alkyl, $C_5$-$C_{10}$ cycloalkyl, 5- to 7-membered heterocyclyl, and $C_6$-$C_{10}$ aryl;

$R^{4f}$ is hydrogen or $C_1$-$C_3$ alkyl; or $R^{4e}$ and $R^{4f}$ taken together with the atom to which each is attached form a 5- to 7-membered heterocyclyl;

$R^{4g}$ is selected from the group consisting of $C_1$-$C_6$ alkyl, $C_5$-$C_{10}$ cycloalkyl, 5- to 7-membered heterocyclyl, $C_6$-$C_{10}$ aryl, and 5- to 10-membered heteroaryl;

wherein the cycloalkyl, heterocyclyl, aryl, or heteroaryl of $R^{4b}$, $R^{4c}$, $R^{4e}$, and $R^{4g}$ is optionally substituted with one or two substituents, each independently selected from the group consisting of halogen, $C_1$-$C_6$ alkyl, halo $C_1$-$C_6$ alkyl, hydroxy, and $C_1$-$C_3$ alkoxy; and, wherein the compound of Formula (I) is not:

N-(2-methoxyethyl)-5,6-dimethyl-2-(pyridin-2-yl)thieno[2,3-d]pyrimidin-4-amine;

or a salt thereof.

2. The compound of claim 1, wherein Z is N.

3. The compound of claim 1, wherein $R^3$ is $C_1$-$C_3$ alkyl.

4. The compound of claim 1, wherein $R^3$ is methyl.

5. The compound of claim 1, wherein $Y^1$, $Y^2$, and $Y^3$ are each CH.

6. The compound of claim 1, wherein n is 0.

7. The compound of claim 1, wherein $R^{A1}$ and $R^{A2}$ are each independently $C_1$-$C_3$ alkyl.

8. The compound of claim 1, wherein $R^{A1}$ and $R^{A2}$ are each methyl.

9. The compound of claim 1, wherein $R^4$ is

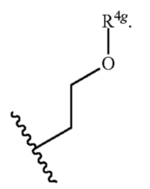

10. The compound of claim 9, wherein $R^{4g}$ is $C_1$-$C_3$ alkyl.

11. The compound of claim 9, wherein $R^{4g}$ is methyl.

12. The compound of claim 1, wherein $R^4$ is

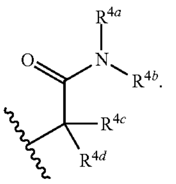

13. The compound of claim 12, wherein $R^{4a}$ is hydrogen or $C_1$-$C_3$ alkyl.

14. The compound of claim 12, wherein $R^{4a}$ is hydrogen.

15. The compound of claim 12, wherein $R^{4a}$ is methyl.

16. The compound of claim 1, wherein $R^{4b}$ is $C_1$-$C_3$ alkyl.

17. The compound of claim 1, wherein $R^{4b}$ is methyl.

18. The compound of claim 1, wherein $R^{4b}$ is phenyl or 5- or 6-membered heteroaryl, optionally substituted with one or two substituents each independently selected from the group consisting of $C_1$-$C_6$ alkyl, hydroxy, and $C_1$-$C_3$ alkoxy.

19. The compound of claim 18, wherein $R^{4b}$ is phenyl, optionally substituted with $C_1$-$C_3$ alkoxy.

20. The compound of claim 18, wherein $R^{4b}$ is phenyl, substituted once with methoxy.

21. The compound of claim 18, wherein $R^{4b}$ is 5- or 6-membered heteroaryl.

22. The compound of claim 21, wherein $R^{4b}$ is pyridinyl.

23. The compound of claim 1, wherein $R^{4c}$ and $R^{4d}$ are each hydrogen.

24. The compound of claim 1, wherein $R^4$ is

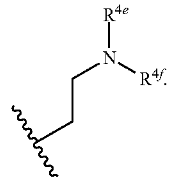

25. The compound of claim 24, wherein $R^{4e}$ and $R^{4f}$ taken together with the atom to which each is attached form a 5- to 7-membered heterocyclyl, optionally substituted with one or two substituents each independently selected from the group consisting of $C_1$-$C_6$ alkyl, hydroxy, and $C_1$-$C_3$ alkoxy.

26. The compound of claim 24, wherein $R^{4e}$ and $R^{4f}$ taken together with the atom to which each is attached form a pyrrolidonyl.

27. The compound of claim 12, wherein $R^6$ is $—O—CH_2CH_2—OH$.

28. The compound of claim 27, wherein $R^{4a}$, $R^{4c}$, and $R^{4d}$ are each hydrogen; and, $R^{4b}$ is selected from the group consisting of pyridinyl, phenyl, cyclopropyl and $C_1$-$C_6$ alkyl, wherein, the pyridinyl, phenyl or cyclopropyl of $R^{4b}$ is optionally substituted with one or two substitutents selected from the group consisting of fluoro, methyl, $—CF_3$ and methoxy.

29. The compound of claim 12, wherein $R^6$ is $—O—CH_2CH_2—R^{bb}$.

30. The compound of claim 28, wherein $R^{bb}$ is selected from the group consisting of $—N(CH_3)_2$, morpholinyl, piperazinyl, tetrahydropyrrolyl, imidazolyl, and

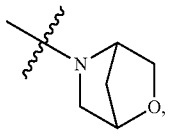

wherein, the morpholinyl, piperazinyl, imidazolyl or tetrahydropyrrolyl of $R^{bb}$ is optionally substituted with one or two substitutents selected from the group consisting of halogen, $C_1$-$C_6$ alkyl, halo $C_1$-$C_6$ alkyl and $C_1$-$C_6$ alkoxy.

31. The compound of claim 30, wherein $R^{4a}$, $R^{4c}$, and $R^{4d}$ are each hydrogen; and, $R^{4b}$ is selected from the group consisting of pyridinyl, phenyl, cyclopropyl and $C_1$-$C_6$ alkyl, wherein, the pyridinyl, phenyl or cyclopropyl of $R^{4b}$ is optionally substituted with one or two substitutents selected from the group consisting of fluoro, methyl, $—CF_3$ and methoxy.

32. The compound of claim 28, wherein $Y^1$ is absent.
33. The compound of claim 32, having the Formula Ia:
Ia
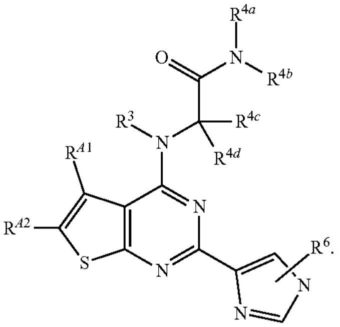
34. The compound of claim 1, or a pharmaceutically acceptable salt thereof, wherein said compound of Formula (I) is selected from the group consisting of:
| Compound No. | Structure |
| --- | --- |
| 1 | 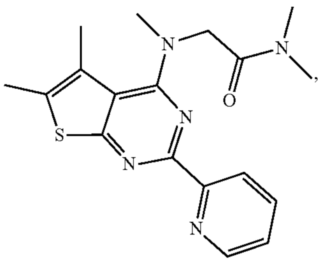 |
| 2 | 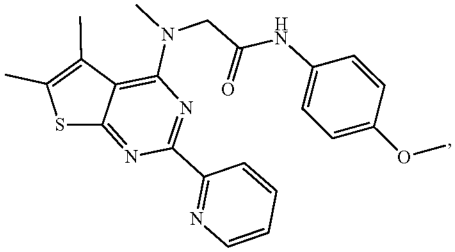 |
| 3 | 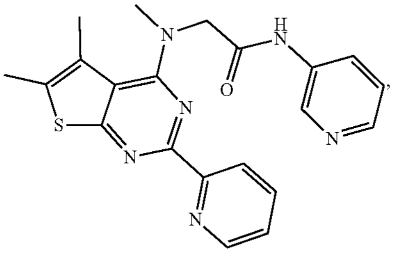 [SMILES: Cc1sc2nc(-c3ccccn3)nc(N(C)CC(=O)Nc3cccnc3)c2c1C] |
-continued
| Compound No. | Structure |
| --- | --- |
| 4 | 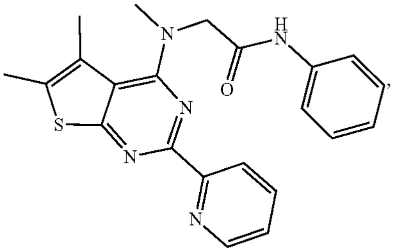 [SMILES: Cc1sc2nc(-c3ccccn3)nc(N(C)CC(=O)Nc3ccccc3)c2c1C] |
| 5 | 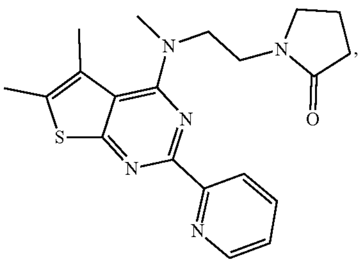 [SMILES: Cc1sc2nc(-c3ccccn3)nc(N(C)CCN3CCCC3=O)c2c1C] |
| 6 | 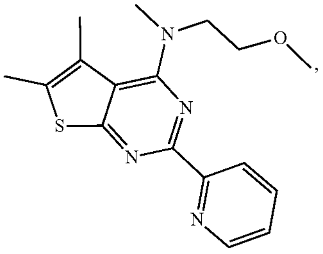 |
| 7 | 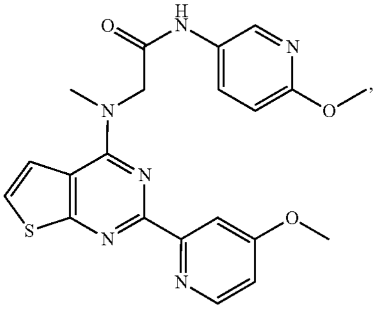 [SMILES: COc1ccnc(-c2nc(N(C)CC(=O)Nc3ccc(OC)nc3)c3ccsc3n2)c1] |
| 8 | 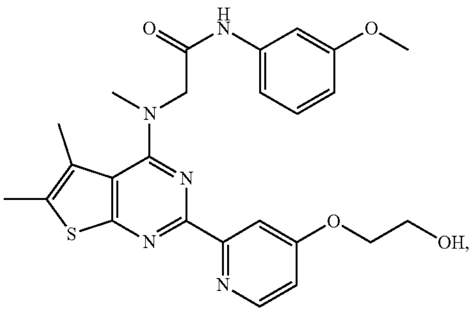 [SMILES: COc1cccc(NC(=O)CN(C)c2nc(-c3cc(OCCO)ccn3)nc3sc(C)c(C)c23)c1] |

-continued
| Compound No. | Structure |
|---|---|
| 9 | 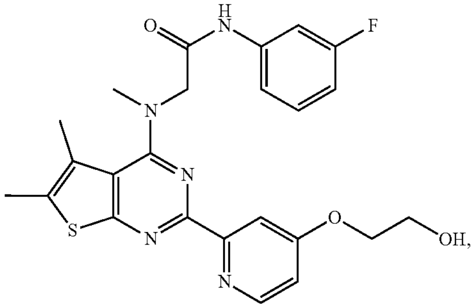 [SMILES: Cc1sc2nc(-c3cc(OCCO)ccn3)nc(N(C)CC(=O)Nc3cccc(F)c3)c2c1C], |
| 10 | 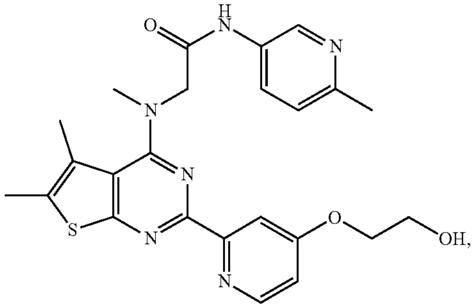 [SMILES: Cc1ccc(NC(=O)CN(C)c2nc(-c3cc(OCCO)ccn3)nc3sc(C)c(C)c23)cn1], |
| 11 | 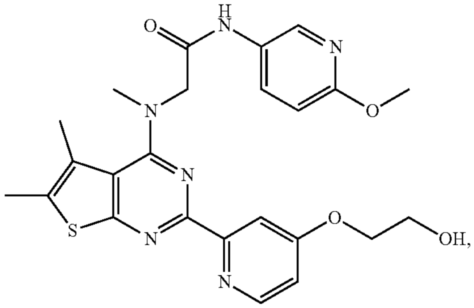 [SMILES: COc1ccc(NC(=O)CN(C)c2nc(-c3cc(OCCO)ccn3)nc3sc(C)c(C)c23)cn1], |
| 12 | 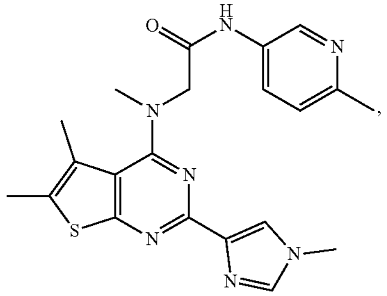, |
| 13 | 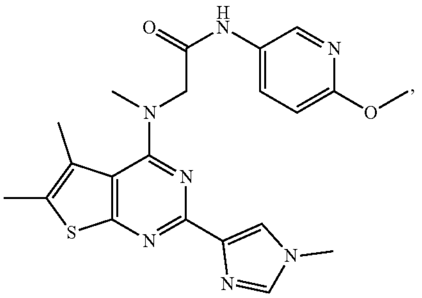, |
-continued
| Compound No. | Structure |
|---|---|
| 14 | 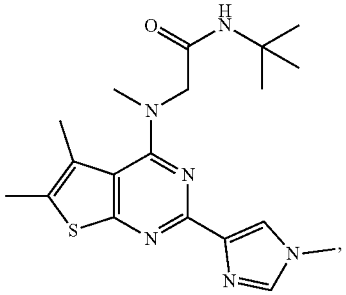, |
| 15 | 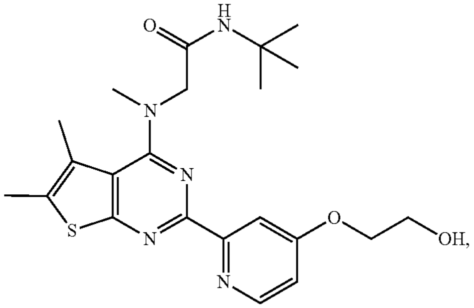 [SMILES: Cc1sc2nc(-c3cc(OCCO)ccn3)nc(N(C)CC(=O)NC(C)(C)C)c2c1C], |
| 16 | 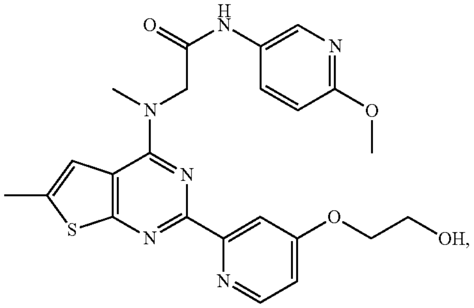 [SMILES: COc1ccc(NC(=O)CN(C)c2nc(-c3cc(OCCO)ccn3)nc3sc(C)cc23)cn1], |
| 17 | 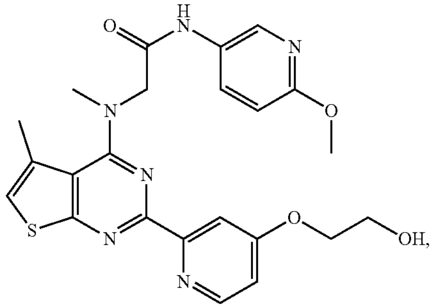 [SMILES: COc1ccc(NC(=O)CN(C)c2nc(-c3cc(OCCO)ccn3)nc3scc(C)c23)cn1], |
| 18 | 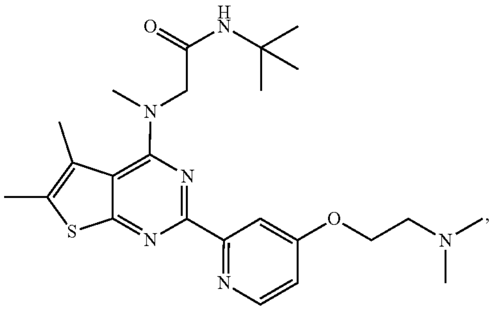, |

-continued

| Compound No. | Structure |
|---|---|
| 19 | 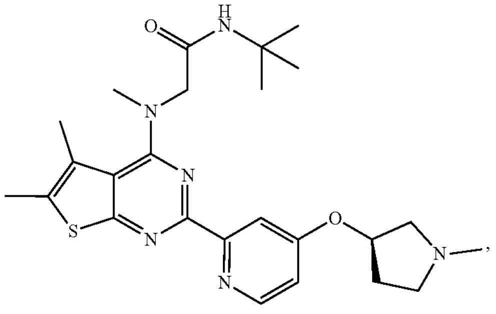 |
| 20 | 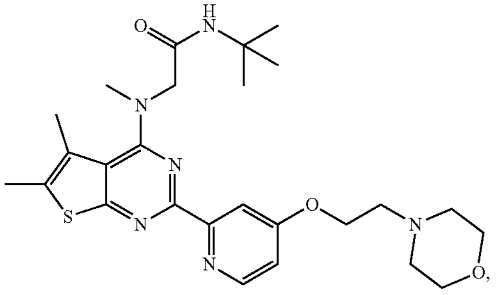 [SMILES: Cc1sc2nc(-c3cc(OCCN4CCOCC4)ccn3)nc(N(C)CC(=O)NC(C)(C)C)c2c1C] |
| 21 | 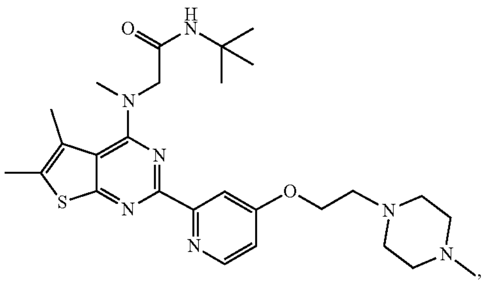 |

-continued

| Compound No. | Structure |
|---|---|
| 22 | 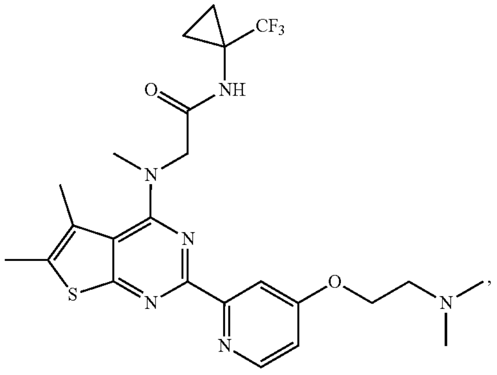 |
| 23 | 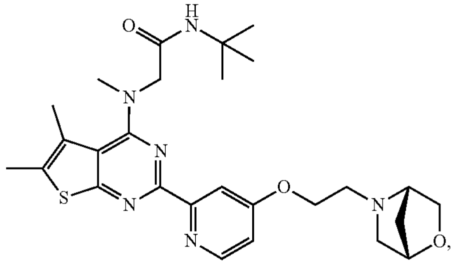 and |
| 24 | 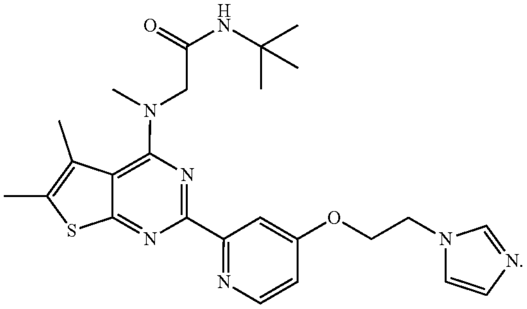 [SMILES: Cc1sc2nc(-c3cc(OCCn4ccnc4)ccn3)nc(N(C)CC(=O)NC(C)(C)C)c2c1C] |

35. A pharmaceutical composition comprising a compound according to claim 1, or a pharmaceutically acceptable salt thereof, and a pharmaceutically acceptable excipient.

36. A method of inhibiting iron transport mediated by ferroportin in a subject, comprising administering to the subject an effective amount of a compound of claim 1.

37. The compound of claim 31, wherein $Y^1$ is absent.

38. A method of inhibiting iron transport mediated by ferroportin in a subject, comprising administering to the subject the pharmaceutical composition of claim 35.

* * * * *